(12) United States Patent
Huggins et al.

(10) Patent No.: US 9,163,018 B2
(45) Date of Patent: Oct. 20, 2015

(54) METHOD OF TREATMENT OF AGE-RELATED MACULAR DEGENERATION (AMD)

(71) Applicant: Prana Biotechnology Limited, Victoria (AU)

(72) Inventors: Penelope Jane Huggins, Victoria (AU); Gaik Being Kok, Victoria (AU)

(73) Assignee: PRANA BIOTECHNOLOGY INC., Parkville, Victoria (AU)

( * ) Notice: Subject to any disclaimer, the term of this patent is extended or adjusted under 35 U.S.C. 154(b) by 0 days.

(21) Appl. No.: 14/087,689

(22) Filed: Nov. 22, 2013

(65) Prior Publication Data

US 2014/0088122 A1   Mar. 27, 2014

Related U.S. Application Data

(63) Continuation of application No. 12/952,425, filed on Nov. 23, 2010, now abandoned, which is a continuation of application No. 12/297,165, filed as application No. PCT/AU2007/000490 on Apr. 13, 2007, now abandoned.

(60) Provisional application No. 60/792,278, filed on Apr. 14, 2006.

(51) Int. Cl.

| C07D 471/04 | (2006.01) |
|---|---|
| A61K 31/517 | (2006.01) |
| A61K 31/4375 | (2006.01) |
| A61K 31/4412 | (2006.01) |
| A61K 31/47 | (2006.01) |
| A61K 31/4709 | (2006.01) |
| A61K 31/4725 | (2006.01) |

(52) U.S. Cl.
CPC .......... *C07D 471/04* (2013.01); *A61K 31/4375* (2013.01); *A61K 31/4412* (2013.01); *A61K 31/47* (2013.01); *A61K 31/4709* (2013.01); *A61K 31/4725* (2013.01); *A61K 31/517* (2013.01)

(58) Field of Classification Search
CPC .................................................... C07D 471/04
See application file for complete search history.

(56) References Cited

U.S. PATENT DOCUMENTS

| 4,291,036 | A | 9/1981 | Knoll et al. |
|---|---|---|---|
| 5,902,810 | A | 5/1999 | Pfleiderer et al. |
| 6,001,852 | A | 12/1999 | Gerolymatos |
| 6,337,332 | B1 | 1/2002 | Carpino |
| 6,369,058 | B1 | 4/2002 | Hussain et al. |
| 2002/0025944 | A1 | 2/2002 | Bush et al. |
| 2006/0183909 | A1 | 8/2006 | Schmitt et al. |
| 2008/0119470 | A1 | 5/2008 | Kok et al. |

FOREIGN PATENT DOCUMENTS

| EP | 0290819 B1 | 11/1988 |
|---|---|---|
| EP | 1477482 | 9/2003 |
| GB | 713767 | 8/1954 |
| WO | 94/21246 A1 | 9/1994 |
| WO | 9424379 A1 | 10/1994 |
| WO | 9512417 A1 | 5/1995 |
| WO | 9524379 | 9/1995 |
| WO | 9622990 A1 | 8/1996 |
| WO | 9806403 | 2/1998 |
| WO | 9833802 | 8/1998 |
| WO | 9847969 A1 | 10/1998 |
| WO | 9901441 | 1/1999 |
| WO | 0024707 A1 | 5/2000 |
| WO | 0116114 | 3/2001 |
| WO | 0248117 | 6/2002 |
| WO | 0250065 A2 | 6/2002 |
| WO | 02/055081 A2 | 7/2002 |
| WO | 02085908 A1 | 10/2002 |
| WO | 03010146 A1 | 2/2003 |
| WO | 03016309 A1 | 2/2003 |
| WO | 03076418 | 9/2003 |
| WO | 2004/007461 A1 | 1/2004 |
| WO | 2004031161 A1 | 4/2004 |
| WO | 2004/087160 A1 | 10/2004 |
| WO | 2004113277 A2 | 12/2004 |
| WO | 2005/095360 A1 | 10/2005 |
| WO | 2006083533 | 8/2006 |
| WO | 2006/117660 A2 | 11/2006 |

OTHER PUBLICATIONS

Hermecz et al., Nitrogen-bridgehead compounds; 40. Cyclization in phosphoryl chloride-polyphosphoric acid mixture, Synthesis (1984), (2), 152-8.
Supplementary European Search Report dated Jan. 14, 2011 for Application No. EP 07 71 8737.
Chemical Abstract 45:47030 (& Yakugaku Zasshi (1945), 65, 69) See Chem Abs RN410543-30-5.
Chemical Abstract 111:194704 (& Tetrahedron Letters (1989, 30 (12), 1529-39).
Chemical Abstract 24:53157 (& Journal of the American Chemical Society, 1930, 52, 3974.7).
Chemical Abstract 48:46261 (& Journal of the Chemical Society, Abstracts, 1952, 5985-5993).
Lengyel Imre et al "High concentration of zinc in sub-retinal pigment epithelial deposits" Experimental Eye Research col. 84(4): 772-80 Epub Jan. 9, 2007.
Koshimuro K. et al. "The Role of 6R-tetrahydrobiopterin in the nervous system", Progress in Neurobiology 61 (2000), 415-438.

(Continued)

*Primary Examiner* — Brian McDowell
(74) *Attorney, Agent, or Firm* — Scully, Scott, Murphy & Presser P.C.

(57) ABSTRACT

The present invention relates generally to the field of treatment and prophylaxis of retinal degenerative diseases. More particularly, the present invention contemplates a method for preventing, reducing the risk of development of, or otherwise treating or ameliorating the symptoms of, age-related macular degeneration (AMD) or related retinal conditions in mammals and in particular humans. The present invention further provides therapeutic compositions enabling dose-dependent or dose-specific administration of agents useful in the treatment and prophylaxis of age-related macular degeneration or related retinal degenerative conditions.

7 Claims, No Drawings

(56) References Cited

OTHER PUBLICATIONS

Constantino et al. "Modeling of Poly(ADP-ribose) polymerase (PARP) inhibitors. Docking of ligands and Quantitative Structure-Activity Relationship Analysis", J. Med. Chem., 44:23, 3786-3794 (2001).
Banker et al., Modern Pharmaceuticals (1996) p. 596-7.
Borisy et al., Proceedings of the National Academy of Science of the United States of America, (2003) 100(13) 7977-7982.
Malesani et al., Atti-Istituto Veneto di Scienze, Lettere ed Arti, Classe di Scienze Matematiche e Naturali (1973), vol. Date 1972, 131, 9-16 together with English language abstract.
Vippagunta et al., Advanced Drug Delivery Reviews 48 (2001) 3-26.
Lauenstein et al., Biochimica et Biophysica Acta (1956), 21, 587-8.
Iyer et al., Journal of Scientific & Industrial Research (1956), 15C, 1-7.
Iyer et al., J. Sci Ind. Res., 20C, 1961, 175-177.
Iyer et al., J. Sci. Industr. Res., vol. 17C, 1958, 193-196.
Nowak et al., Journal Arzneimittal-Forschung (1996), 16(3), 407-11.
Dörwald, F. Zaragoza. Side Reactions in Organic Synthesis: A Guide to Successful Synthesis Design, Weinheim: Wiley-VCH Cerlag GmbH & Co. KGaA, 2005, Preface.
Wolff, Manfred E., Ed. Burger's Medical Chemistry and Drug Discovery—Fifth Edition, New York: John Wiley & Sons, 1996, vol. 1, pp. 975-976.
International Search Report dated Jun. 9, 2007 for International Application No. PCT/AU2007/000490.

METHOD OF TREATMENT OF AGE-RELATED MACULAR DEGENERATION (AMD)

CROSS REFERENCE TO RELATED APPLICATIONS

The present application is a Continuation of U.S. Ser. No. 12/952,425 filed Nov. 23, 2010, which is a continuation of U.S. Ser. No. 12/297,165, filed Feb. 16, 2010, now abandoned, which is a 371 of international appln. no. PCT/AU2007/000490, filed Apr. 13, 2007; which claims priority from provisional application No. 60/792,278, filed Apr. 14, 2006.

BACKGROUND OF THE INVENTION

1. Field of the Invention

The present invention relates generally to the field of treatment and prophylaxis of retinal degenerative diseases. More particularly, the present invention contemplates a method for preventing, reducing the risk of development of, or otherwise treating or ameliorating the symptoms of, age-related macular degeneration (AMD) or related retinal conditions in mammals and in particular humans. The present invention further provides therapeutic compositions enabling dose-dependent or dose-specific administration of agents useful in the treatment and prophylaxis of age-related macular degeneration or related retinal degenerative conditions.

2. Description of the Prior Art

Reference to any prior art in this specification is not, and should not be taken as, an acknowledgment or any form of suggestion that that prior art forms part of the common general knowledge in any country.

Bibliographic details of references in the subject specification are also listed at the end of the specification.

Macular degeneration is a clinical term that is used to describe a family of diseases that are all characterized by a progressive loss of central vision associated with abnormalities of Bruch's membrane, the choroid, the neural retina and/or the retinal pigment epithelium. These disorders include very common conditions that affect older subjects—such as AMD as well as rarer, earlier-onset dystrophies that in some cases can be detected in the first decade of life. Other maculopathies include North Carolina macular dystrophy, Sorsby's fundus dystrophy, Stargardt's disease, pattern dystrophy, Best disease and Malattia leventinese.

AMD is the leading cause of permanent vision loss for individuals over age 65, currently affecting approximately 15 million Americans. AMD affects light-sensitive photoreceptor cells and pigmented epithelial cells in the macula, the center of the retina of the eye. While it may not cause total blindness, the disease destroys central vision, making reading, watching electronic monitor screens and driving impossible. It has no documented cure, has never demonstrated spontaneous remission and effective treatments are very limited.

The retina is a complicated network of nerve cells that changes light into nerve impulses that travel to the brain where they are interpreted as visual images. The central part of the retina, called the macula, is responsible for vision that is needed for reading and other detailed work. Damage to the macula results in poor vision. The most common disease process that affects the macula is AMD. In patients with AMD, retinal photoreceptor and pigment epithelial cells in the macula die over the course of several years. The cell death and gradual visual loss usually do not begin until age 60 or older, hence the name age-related macular degeneration.

There are two types of AMD: dry macular degeneration and wet macular degeneration. Dry macular degeneration, although more common, typically results in a less severe, more gradual loss of vision. Patients who are affected by dry AMD have gradual loss of central vision due to the death of photoreceptor cells and their close associates, retinal pigmented epithelial (RPE) cells, with deposition of a complex waxy amyloid mixture, termed 'drusen'. Photoreceptors, the cells in the retina that actually 'see' light, are essential for vision. Macrophagic RPE cells are necessary for photoreceptor survival, function and renewal.

Patients with wet macular degeneration develop new blood vessels under the retina. As the photoreceptor and RPE cells slowly degenerate, there is a tendency for blood vessels to grow from their normal location in the choroid into an abnormal location beneath the retina. This abnormal new blood vessel growth is called choroidal neovascularization (CNV). The abnormal blood vessels leak and bleed, causing hemorrhage, swelling, scar tissue, and severe loss of central vision. Only 10% of patients with AMD have the wet type, but it is responsible for 90% of all blindness resulting from AMD.

The RPE cells in the eye act as macrophages, which phagocytize and recycle components of the membranous outer segments of photoreceptors. If the mitochondria within the RPE cells are damaged, the photoreceptor recycling is inhibited, with resultant accumulation of drusen. Drusen causes a lateral stretching of the RPE monolayer and physical displacement of the RPE from its immediate vascular supply, the choriocapillaris. This displacement creates a physical barrier that may impede normal metabolite and waste diffusion between the choriocapillaris and the retina.

Depending on the location, laser treatment can sometimes be given to destroy the abnormal blood vessels formed in wet AMD. Only 15% of the cases of wet AMD are eligible to have laser treatment because the blood vessels can not be located too close to the center part of the macula. The laser is a beam of light that is absorbed by the pigment of blood, drugs and RPE cells, which converts to heat energy that cauterizes the abnormal blood vessels. Frequently the neovascularization returns, since the stimulus has not been removed, resulting in severe loss of vision. In fact, most of the patients with AMD, who have very poor vision, have lost it due to sequelae of neovascularization. Current medical opinion states that there is no treatment available that permanently prevents the cell death or abnormal blood vessel growth that occurs in AMD.

To date, there are no known specific measures to prevent the occurrence of AMD. For patients already diagnosed with AMD in one or both eyes, current main treatments include light targeting (phototherapy) and/or a vitamin and mineral supplement, each of which is of debatable value. Phototherapy involves targeting light to the macular area containing the lesion of nascent defective blood vessels to inhibit or impair their function. One type of phototherapy is photodynamic therapy (PDT). In PDT, a photosensitive agent is administered into the vessels of a patient, then the agent is activated at the target site of the lesion of new vessels (the macula) by directing low energy light from a laser specifically to this area. The activated agent generates free radicals and other activated chemical species which destabilize and destroy the new vessels.

PDT has been reported to be of some benefit to patients having AMD. For example, one study, (*Arch. Ophthalmol.* 117:1329-1345, 1999) evaluated PDT in four hundred and two eyes from patients diagnosed with AMD in at least one eye. Treatment outcome was assessed by comparing the patient's ability to accurately read a conventional vision chart (one having about five letters per line) pre-treatment and post-treatment. At twelve months post-PDT, 61% of the eyes (246/402) lost fewer than 15 letters (that is, the patient lost less than about three lines on a standard visual chart), while 46% of the eyes (96/207) from patients undergoing treatment with a placebo lost fewer than 15 letters (p<0.001). At twenty-four months post-PDT, the visual acuity and contrast sensitivity was sustained in patients receiving PDT. A significantly greater percentage of these patients (58%) lost fewer than 15 letters, compared to patients undergoing treatment with a placebo (38%). However, only 16% of the patients receiving PDT had improved vision, compared to 7% of the patients receiving a placebo.

Another type of phototherapy is photocoagulation therapy. In photocoagulation therapy, high energy light from a laser is directed specifically to the target site of the new vessels. The heat generated from the high energy laser coagulates the fluid in and around the new vessels. Laser photocoagulation is not a form of PDT; it is a separate treatment approach. It uses lateral transfer of heat, applied with a cautery-like method, to coagulate fluid within and surrounding the vessel, while PDT uses an activated photosensitive agent to generate active chemicals which damage or destroy the new vessels containing the agent.

While either PDT or laser photocoagulation therapy is separately used to treat patients with AMD, neither is without drawbacks. A problem with PDT is that its effects are transient; patients receiving PDT must be retreated about every three months. Furthermore, the patients require at least five retreatments within the first two years merely to stabilize their condition, and before any therapeutic effect occurs. These cumulative treatments damage the retina, further reducing the patient's visual acuity.

One drawback of laser photocoagulation is that it is non-selective, and does not target only the new blood vessels. It must therefore be administered so that only the lesions are targeted, and the unaffected surrounding tissues are undamaged. However, in about half of the patients with AMD, the new vessels are located in the subfoveal area, which is difficult or impossible to target with laser coagulation without damaging the sensory retina. Another drawback is that photocoagulation treatment is not permanent and recurrence rates for new vessel production are high, reaching 39-76%, usually within the first two years. However, repeated treatments can actually induce the growth of new vessels and membranes (subretinal neovascular membranes and recurrent choroidal neovascularizations) at the site of the treatment. Repeated treatments may also irreversibly damage unaffected areas of the retina, including the neurosensory retinal and RPE. Thus, the treatment itself may result in the patient having further reduced vision over a period of time. Specifically, some patients undergoing photocoagulation therapy develop scotoma, which is an area of depressed vision within the visual field, surrounded by an area of less depressed or of normal vision.

There is a need, therefore, to develop alternative methods to treat AMD or related conditions.

SUMMARY OF THE INVENTION

The present invention is predicated in part on the recent determination that proteinaceous deposits on the limiting membrane of the retina, referred to as "drusen", also comprise zinc and copper and hence are proposed to be similar to an amyloid type plaque. Hence, the present invention contemplates the use of a metal protein attenuating compound (MPAC) to reduce the levels of or otherwise remove excess metal from drusen thereby restoring normal metal homeostasis in the retina. The present invention is particularly useful for treating or preventing or otherwise reducing the risk of development of age-related macular degeneration (AMD); however, the subject invention extends to the treatment of any retinal degenerative disorder associated with amyloid type aggregates, complexes, deposits or plaques or any condition associated with drusen which comprise excess metal.

The method of the present invention is useful irrespective of any inhibition of a matrix metalloproteinase and/or a dose-specific amount of MPAC may be employed. A single agent may be administered or a combination of two or more agents.

The present agents comprise at least two fused 6-membered rings with at least a nitrogen atom at position 1 and a hydroxy or mercapto group at position 8. Useful compounds are defined by Formulae I through XXVII which are described in detail below.

Examples of suitable compounds include those in Table 8 such as PB-1033, PB-1076, PB-1085, PB-1120, PB-1127, PB-1135, PB-1149, PB-1151, PB-1160 and PB-1168 or a pharmaceutically acceptable salt or derivative or functional equivalent thereof.

Hence, one aspect of the present invention contemplates a method for the treatment or prophylaxis of a retinal degenerative condition or disorder in a subject, said method, comprising administering to said subject an effective amount of an MPAC or formulation comprising an MPAC for a time and under conditions effective to alter metal levels in retinal drusen or surrounding tissue.

The present invention also provides a method for the treatment or prophylaxis of a retinal degenerative condition or disorder in a subject, said method comprising administering to said subject an effective amount of an MPAC or formulation comprising an MPAC for a time and under conditions effective to reduce metal levels in retinal drusen or surrounding tissue.

In particular, the present invention provides a method for treating a subject with age-related macular degeneration (AMD) said method comprising administering to said subject an amount of PB-1033 or a pharmaceutically acceptable salt, derivative or functional equivalent thereof effective to reduce metal in retinal drusen to a level which ameliorates symptoms of AMD.

The phrases "alter metal levels" and "reduce metal" is used in its broadest sense and refers to a change in the distribution of a metal in retinal drusen or surrounding tissue as well as a change in the amount or activity of metal in drusen or surrounding tissue. The phrases also refer to a reduction in the amount or activity of metal in retinal drusen or surrounding tissue as well as a reduction in the amount or activity of metal in particular areas i.e. the distribution of metal in retinal drusen or surrounding tissue.

The selection of an MPAC is generally but not exclusively irrespective of its ability to inhibit a metalloproteinase. A defined or specific dosage amount may also be administered.

Accordingly, another aspect of the present invention provides a method for the treatment or prophylaxis of a retinal degenerative condition or disorder in a subject, said method comprising administering to said subject an effective amount of an MPAC or formulation comprising an MPAC for a time and under conditions effective to reduce metal levels in retinal drusen or surrounding tissue, irrespective of any effect on a matrix metalloproteinase.

Reference to "irrespective" means that one or more metalloproteinases may be inhibited or no metalloproteinases are inhibited.

Still another aspect of the present invention defines a specific dosage range to optimally restore metal homeostasis in the retina.

Hence, this aspect of the present invention is directed to a method for the treatment or prophylaxis of a retinal degenerative condition or disorder in a subject, said method comprising administering to said subject an effective amount of an MPAC or formulation comprising an MPAC for a time and under conditions effective to reduce metal levels in retinal drusen or surrounding tissue wherein the effective amount is a specific dose range to optimally restore metal homeostasis in the retina.

Another aspect of the present invention contemplates a method for reducing levels of a metal from retinal drusen in a subject to thereby ameliorate symptoms of age-related macular degeneration (AMD) said method comprising administering to said subject an effective amount of PB-1033 or a pharmaceutically acceptable salt, derivative or functional equivalent thereof.

The present invention also provides for the use of an MPAC in the manufacture of a medicament for the treatment of a retinal degenerative disorder in a subject.

In particular, the present invention contemplates the use of PB-1033 or a pharmaceutically acceptable salt, derivative or functional equivalent thereof in the manufacture of a medicament for the treatment of age-related macular degeneration (AMD) in a subject.

Combination therapy also forms part of the present invention in which two or more MPACs are administered or an MPAC and another active such as a metal chelator, cytokine, genetic molecule anti-microbial or anti-viral agent, an anti-oxidant, an antibiotic and/or an anesthetic.

The preferred subject is a human although the present invention has application in the veterinary, horse racing and animal husbandry industries.

The present invention further provides formulations for treating, preventing or reducing the risk of developing a retinal degenerative condition or disorder comprising an MPAC as herein described.

Whilst PB-1033 is a particularly useful MPAC, the present invention extends to any MPAC encompassed by the compounds of Formulae I through XXVII such as but not limited to those in Table 8 including PB-1076, PB-1085, PB-1120, PB-1127, PB-1135, PB-1149, PB-1151, PB-1160 and PB-1168 or a pharmaceutically salt or derivative or functional equivalent thereof.

Abbreviations used herein are defined in Table 1.

TABLE 1

ABBREVIATIONS

| ABBREVIATION | DESCRIPTION |
| --- | --- |
| AMD | Age-related macular degeneration |
| BBB | Blood brain barrier |
| CNV | Choroidal neovascularisation |
| Drusen | Proteinaceous deposits on limiting membrane of retina |
| MPAC | Metal protein attenuated compound |
| PDT | Photodynamic therapy |
| RPE cells | Retinal pigmented epithelial cells |

DETAILED DESCRIPTION OF THE INVENTION

Throughout this specification, unless the context requires otherwise, the word "comprise", or variations such as "comprises" or "comprising", were understood to imply the inclusion of a stated element or integer or group of elements or integers but not the exclusion of any other element or integer or group of elements or integers.

All scientific citations, patents, patent applications and manufacturer's technical specifications referred to hereinafter are incorporated herein by reference in their entirety.

Reference to any prior art in this specification is not, and should not be taken as, an acknowledgment or any form of suggestion that that prior art forms part of the common general knowledge in any country.

It is to be understood that unless otherwise indicated, the subject invention is not limited to specific formulation components, manufacturing methods, biological materials or reagents, dosage regimens and the like, as such may vary. It is also to be understood that the terminology used herein is for the purpose of describing particular embodiments only and is not intended to be limiting.

As used in the subject specification, the singular forms "a", "an" and "the" include plural aspects unless the context clearly dictates otherwise. Thus, for example, reference to "a formulation" includes a single formulation, as well as two or more formulations; reference to "an agent" or "a reagent" includes a single agent or reagent, as well as two or more agents or reagents; and so forth.

The terms "agent", "reagent", "compound", "pharmacologically active agent", "medicament", "therapeutic", "active" and "drug" are used interchangeably herein to refer to a chemical or biological entity which induces or exhibits a desired effect such as ameliorating the symptoms of a retinal degenerative disease. The terms also encompass pharmaceutically acceptable and pharmacologically active ingredients of those active agents specifically mentioned herein. When the terms "agent", "reagent", "compound", "pharmacologically active agent", "medicament", "therapeutic", active" and "drug" are used, then it is to be understood that this includes the active entity per se as well as pharmaceutically acceptable, pharmacologically active salts, esters, amides, pro-drugs, metabolites, analogs, etc.

Reference to an "agent", "chemical agent", "compound", "pharmacologically active agent", "medicament", "therapeutic", "active" and "drug" includes combinations of two or more active agents. A "combination" also includes multi-part such as a two-part composition where the agents are provided separately and given or dispensed separately or admixed together prior to dispenzation. For example, a multi-part pharmaceutical pack may have two or more agents separately maintained. Hence, this aspect of the present invention includes combination therapy. Combination therapy includes the co-administration of a metal chelator and another active such as a chemical compound, cytokine, genetic molecule, anti-microbial or anti-viral agent, an antibiotic and/or an anasthetic.

The terms "effective amount" and "therapeutically effective amount" of an agent as used herein mean a sufficient amount of the agent to provide the desired therapeutic or physiological or effect or outcome. Such an effect or outcome includes altering or reducing availability of metal ions and/or reducing their amount in drusen, reducing amyloid levels reducing or preventing macular degeneration or a related condition and/or treating or preventing vision impairment. Undesirable effects, e.g. side effects, are sometimes manifested along with the desired therapeutic effect; hence, a practitioner balances the potential benefits against the potential risks in determining what is an appropriate "effective amount". The exact amount required will vary from subject to subject, depending on the species, age and general condition of the subject, mode of administration and the like. Thus, it may not be possible to specify an exact "effective amount". However, an appropriate "effective amount" in any individual case may be determined by one of ordinary skill in the art using only routine experimentation.

The effective amount is deemed the amount required to prevent or ameliorate symptoms of the retinal degeneration condition such as AMD. In one embodiment, the amount of MPAC used is the amount required to or which is effective in reducing levels of metal drusen. Examples of metals include zinc and copper. Effective amounts include from 1 ng/ml to 1000 mg/ml such as from about 5 ng/ml to about 500 mg/ml or about 10 ng/ml to about 100 mg/ml or amounts or ranges in between.

The terms "metal" and "metal ion: may be used interchangeably in this context.

By "pharmaceutically acceptable" carrier, excipient or diluent is meant a pharmaceutical vehicle comprised of a material that is not biologically or otherwise undesirable, i.e. the material may be administered to a subject along with the selected active agent without causing any or a substantial adverse reaction. Carriers may include excipients and other additives such as diluents, detergents, coloring agents, wetting or emulsifying agents, pH buffering agents, preservatives, and the like.

Similarly, a "pharmacologically acceptable" salt, ester, amide, prodrug or derivative of a compound as provided herein is a salt, ester, amide, prodrug or derivative that this not biologically or otherwise undesirable.

"Treating" a subject may involve prevention of a retinal degenerative condition or other adverse physiological event in a susceptible individual as well as treatment of a clinically symptomatic individual by ameliorating the symptoms of the condition. In particular, the presence invention contemplates a reduction of amyloid type plaque formation and/or a reduction in metal content in drusen to restore normal metal homeostasis in the retina.

The "subject" as used herein refers to an animal, preferably a mammal and more preferably a primate including a lower primate and even more preferably a human who can benefit from the formulations and methods of the present invention. A subject regardless of whether a human or non-human animal may be referred to as an individual, patient, animal, host or recipient. The compounds and methods of the present invention have applications in human medicine, veterinary medicine as well as in general, domestic or wild animal husbandry. For convenience, an "animal" includes an avian species such as a poultry bird (including ducks, chicken, turkeys and geese), an aviary bird or game bird. The condition in a non-human animal may not be a naturally occurring but induced such as in an animal model.

As indicated above, the preferred animals are humans, non-human primates such as marmosets, baboons, orang-utans, lower primates such as tupia, livestock animals, laboratory test animals, companion animals or captive wild animals. A human is the most preferred target. However, non-human animal models may be used.

Examples of laboratory test animals include mice, rats, rabbits, guinea pigs and hamsters. Rabbits and rodent animals, such as rats and mice, provide a convenient test system or animal model as do primates and lower primates. Livestock animals include sheep, cows, pigs, goats, horses and donkeys. Non-mammalian animals such as avian species, zebrafish, amphibians (including cane toads) and *Drosophila* species such as *Drosophila melanogaster* are also contemplated. Instead of a live animal model, a test system may also comprise a tissue culture system.

A "retinal degenerative condition" is a condition which is characterized by a progressive loss of vision. Conditions within the scope of this term include age-related macular degeneration (AMD), North Carolina macular dystrophy; Sorsby's fudus dystrosphy, Stargardt's disease, pattern dystrophy, Best disease and Malattia leventinese.

A particular condition for which the agents and the methods of the present invention can be effective is AMD. However, the present invention extends to any retinal degenerative disease associated with or characterized by amyloid like aggregates, deposits or plaques.

Hence, one aspect of the present invention contemplates a method for the treatment or prophylaxis of a retinal degenerative condition or disorder in a subject, said method comprising administering to said subject an effective amount of an MPAC or formulation comprising an MPAC for a time and under conditions effective to alter metal levels in retinal drusen or surrounding tissue. In one embodiment, the altered metal levels are reduced metal levels.

In another embodiment, the present invention provides a method for the treatment or prophylaxis of a retinal degenerative condition or disorder in a subject, said method comprising administering to said subject an effective amount of an MPAC or formulation comprising an MPAC for a time and under conditions effective to alter metal levels in retinal drusen or surrounding tissue, irrespective of any effect on a matrix metalloproteinase. In one embodiment, the altered metal levels are reduced metal levels.

Still a further aspect of the present invention is directed to a method for the treatment or prophylaxis of a retinal degenerative condition or disorder in a subject, said method comprising administering to said subject an effective amount of an MPAC or formulation comprising an MPAC for a time and under conditions effective to reduce metal levels in retinal drusen or surrounding tissue wherein the effective amount is a specific dose range to optimally restore metal homeostasis in the retina.

The present invention also provides for the use of an MPAC in the manufacture of a medicament for the treatment of a retinal degenerative disorder in a subject.

The preferred agents of the present invention comprise at least two fused 6-membered rings with at least a nitrogen atom at position 1 and a hydroxy or mercapto group at position 8. The agents of the present invention are collectively referred to as metal protein attenuating compounds or MPACs and have one or more of the following properties: act as ionophores (i.e. capture and transfer metals into cells), is a metal binder, crosses the blood brain barrier (BBB), exhibits reduced cell toxicity, is capable of dissolving or disrupting amyloid type protein deposits, aggregates or plaques and is stable in aqueous environments.] Preferably, the agents have two or more, three or more or four or more or five or more] of the above-listed properties.

Particularly useful compounds, defined further below, include those in Table 8 such as PB-1033, PB-1076, PB-1085, PB-1120, PB-1127, PB-1135, PB-1149, PB-1151, PB-1160 and PB-1168 or a pharmaceutically salt or derivative or functional equivalent thereof. PB-1033 is particularly useful although the present invention is not to be so limited.

In this regard, the present invention further contemplates a method for treating a subject with age-related macular degeneration (AMD) said method comprising administering to said subject an amount of PB-1033 or a pharmaceutically acceptable salt, derivative or functional equivalent thereof effective to reduce metal in retinal drusen to a level which ameliorates symptoms of AMD.

The subject invention also provides a method for reducing levels of a metal from retinal drusen in a subject to thereby ameliorate symptoms of age-related macular degeneration (AMD) said method comprising administering to said subject an effective amount of PB-1033 or a pharmaceutically acceptable salt, derivative or equivalent thereof.

Examples of pharmaceutically acceptable chemical derivatives or functional equivalents of PB-1033 include those in Table 8 such as PB-1076, PB-1085, PB-1120, PB-1127, PB-1135, PB-1149, PB-1151, PB-1160 and PB-1168 or a pharmaceutically salt or derivative or functional equivalent thereof. Examples of metals include zinc and copper.

Hence, certain useful agents of the present invention are encompassed by compounds of Formula I:

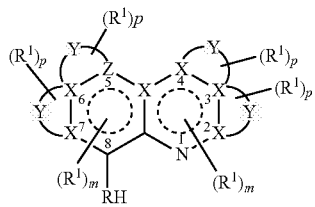

(I)

in which:
R is O or S;
$R^1$ is independently selected from H, optionally substituted alkyl, optionally substituted alkenyl; optionally substituted alkynyl; optionally substituted aryl; optionally substituted heterocyclyl; an antioxidant; a targeting moiety; CN; halo; $CF_3$; $SO_3H$; and $OR^2$, $SR^2$, $SOR^2$, $SO_2R^2$, $(CH_2)_nNR^2R^3$, $HCNOR^2$, $HCNNR^2R^3$, $CONR^2R^3$, $CSNR^2R^3$, $NCOR^2$, $NCSR^2$, $COR^2$, $CO_2R^2$, $CSR^2$ or $SO_2NR^2R^3$ in which $R^2$ and $R^3$ are independently selected from H, optionally substituted alkyl, optionally substituted alkenyl, optionally substituted alkynyl, optionally substituted aryl, optionally substituted heterocyclyl, an antioxidant or a targeting moiety and n is an integer of 1 to 10;
X is independently selected from CH, CO, N and NH;
Z is independently selected from CH, CO, N, NH and O;
Y is independently absent or together with the ring to which it is attached forms a 5- or 6-membered optionally substituted aryl or a 5- or 6-membered optionally substituted heterocyclyl;
m is an integer from 1 to 3; and
p is an integer from 1 to 4,
salts, hydrates, solvates, derivatives, pro-drugs, tautomers and/or isomers thereof to a subject in need thereof,
with the provisos that:
(i) at least one of X and Z is other than CH; and
(ii) phanquinone or tautomers thereof are excluded i.e., when R is O, $R^1$ at position 7 is OH, X is CH and Y is absent, then Z is not

Preferably, R is O.
In addition, $R^1$ is preferably halo, optionally substituted aryl, optionally substituted heterocyclyl, optionally substituted alkyl, $OR^2$, $SR^2$, $(CH_2)_nNR^2R^3$, $CONR^2R^3$ and $NCOR^2$ in which n, $R^2$ and $R^3$ are as defined above. More preferably $R^1$ is fluorine; iodine; chlorine; optionally substituted phenyl such as 4-halophenyl, for example, 4-fluorophenyl or 4-chlorophenyl; an optionally substituted unsaturated 3 to 6-membered heteromonocyclic group containing 1 to 4 nitrogen atoms such as imidazolyl or pyridinyl; an optionally substituted saturated 3 to 6-membered heteromonocyclic group containing 1 to 4 nitrogen atoms such as imidazolidinyl or piperazinyl; an optionally substituted saturated 3 to 6-membered heteromonocyclic group containing 1 to 2 oxygen atoms and 1 to 3 nitrogen atoms such as morpholinyl; optionally substituted $C_{1-4}$ alkyl such as methyl or ethyl; optionally substituted $C_{2-6}$ cycloalkyl such as cyclopropyl; optionally substituted $C_{1-6}$ alkoxy; optionally substituted thio; $CH_2NR^4R^5$ in which $R^4$ and $R^5$ are independently selected from H and $C_{1-4}$ alkyl; or $CONH(CH_2)_2R^6$ in which $R^6$ is optionally substituted heterocyclyl.

Y is preferably an optionally substituted phenyl; an optionally substituted unsaturated 5- or 6-membered heteromonocyclic group containing 1 to 4 nitrogen atoms such as imidazolyl or pyridinyl; or an optionally substituted saturated 5 or 6-membered heteromonocyclic group containing 1 to 2 oxygen atoms and 1 to 3 nitrogen atoms such as morpholinyl.

The preferred halo group is chlorine but other halogen atoms are encompassed by the present invention.

Illustrative classes of compounds of Formula I are as follows:

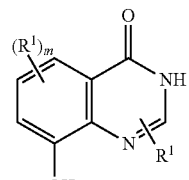 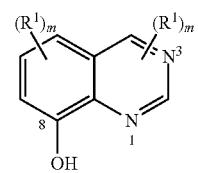

8-hydroxy-4(3H)-quinazolinones    8-hydroxy-quinazoline

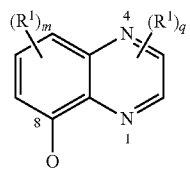 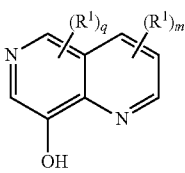

8-hydroxy-quinoxaline    [1,6]naphthyridin-8-ol

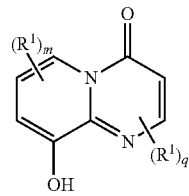 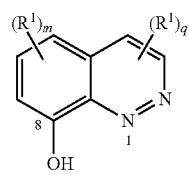

9-hydroxypyrimido[1,6-a]pyrimidin-4-one    8-hydroxy-cinnoline

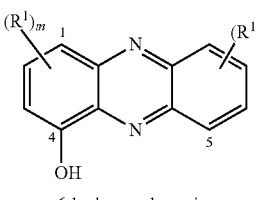 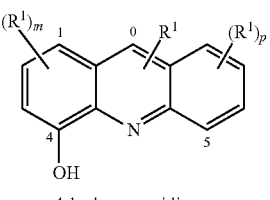

6-hydroxy-phenazine    4-hydroxy-acridine

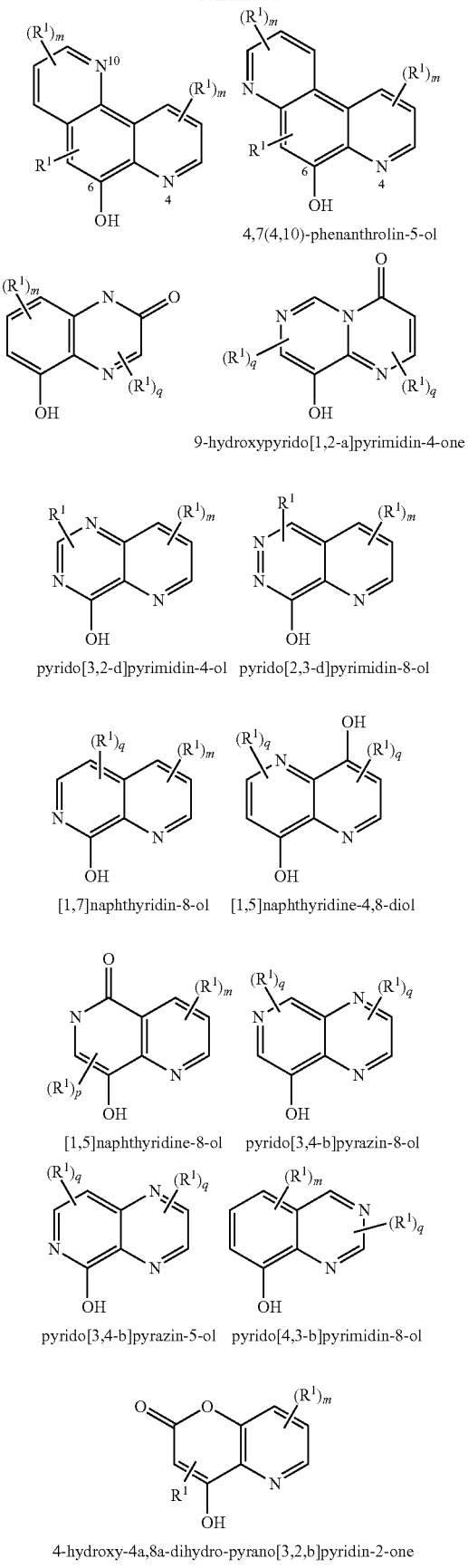

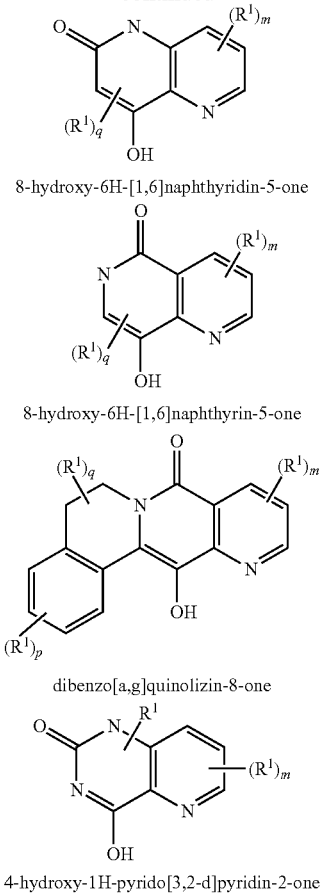

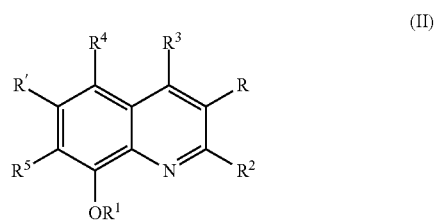

in which $R^1$, m, n and p are as defined above and q is an integer of 1 or 2.

The above compounds also form part of more generic groups of compounds such as those encompassed by Formula II:

(II)

in which $R^1$ is H or halo, optionally substituted alkyl, optionally substituted alkenyl, optionally substituted acyl, optionally substituted aryl, optionally substituted heterocyclyl, an antioxidant or a targeting moiety;

$R^2$ is H; optionally substituted alkyl; optionally substituted alkenyl; optionally substituted aryl; optionally substituted heterocyclyl; optionally substituted alkoxy; an antioxidant; a targeting moiety; $COR^6$ or $CSR^6$ in which $R^6$ is H, optionally substituted alkyl, optionally substituted alkenyl, hydroxy, optionally substituted aryl, optionally substituted heterocyclyl, an antioxidant, a targeting moiety, $OR^7$, $SR^7$ or $NR^7R^8$ in which $R^7$ and $R^8$ are either the same or different and selected from H, optionally substituted alkyl, optionally substituted alkenyl, optionally substituted acyl or optionally substituted heterocyclyl; CN; $(CH_2)_n NR^9 R^{10}$, $HCNOR^9$ or $HCNNR^9 R^{10}$ in which $R^9$ and $R^{10}$ are either the same or different and selected from H, optionally substituted alkyl, optionally substituted alkenyl, optionally substituted aryl or optionally substituted heterocyclyl and n is 1 to 4; $OR^{11}$, $SR^{11}$ or $NR^{11}R^{12}$ in which $R^{11}$ and $R^{12}$ are either the same or different and selected from H, optionally substituted alkyl, optionally substituted alkenyl, optionally substituted aryl or optionally substituted heterocyclyl or together form optionally substituted heterocyclyl; or $SO_2 NR^{13} R^{13} R^{14}$ in which $R^{13}$ and $R^{14}$ are either the same or different and selected from H, optionally substituted alkyl, optionally substituted alkenyl, optionally substituted aryl or optionally substituted heterocyclyl; and $R^3$, $R^4$, $R^5$, R and R' are either the same or different and selected from H, optionally substituted alkyl, optionally substituted alkenyl, optionally substituted alkoxy, optionally substituted acyl, hydroxy, optionally substituted amino, optionally substituted thio, optionally substituted sulphonyl, optionally substituted sulphinyl, optionally substituted sulphonylamino, halo, $SO_3H$, amine, CN, $CF_3$, optionally substituted aryl, optionally substituted heterocyclyl, an antioxidant or a targeting moiety, salts, hydrates, solvates, derivatives, pro-drugs, tautomers and/or isomers thereof with the provisos that:

(a) when $R^1$ to $R^3$, R and R' are H, then $R^4$ is not Cl or I and $R^5$ is not I;

(b) when $R^1$ to $R^3$, R, R' and $R^5$ are H, then $R^4$ is not CHO, $CHOHCCl_3$,

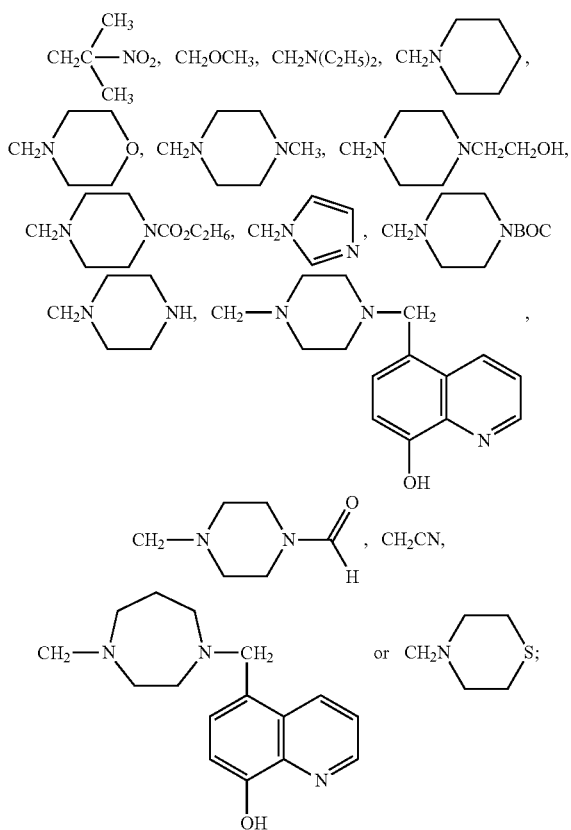

(c) when $R^1$, $R^5$, R' and R are H, $R^2$ is $CO_2H$ and $R^3$ is OH, then $R^4$ is not bromo, methyl, phenyl, hydroxymethyl or trifluoromethyl;

(d) when $R^1$, $R^4$, $R^5$ and R are H, $R^2$ is $CO_2H$ and $R^3$ is OH, then R' is not bromo, iodo, methyl, phenyl, propyl, phenethyl, heptyl, benzylaminomethyl, 3-aminopropyl, 3-hydroxypropyl, 4-methoxyphenyl, 3-methylphenyl, 4-chlorophenyl, 3,4-dichlorophenyl, pyridin-3-yl, furo-2-yl, 4-chlorophenyl, 3,4-dichlorophenyl, 2-chlorophenyl, 3-chlorophenyl, 2-chlorophenyl, 3-chlorophenyl, 2-methoxyphenyl or piperidin-2-yl;

(e) when $R^1$, $R^4$, R and R' are H, $R^2$ is $CO_2H$ and $R^3$ is OH, then $R^5$ is not phenyl, 3-hydroxypropyl, phenethyl, 3-aminoprop-1-yl or hex-1-yl;

(f) when $R^1$, $R^4$, R' and $R^5$ are H, $R^2$ is $CO_2H$ and $R^3$ is OH, then R is not N-morpholinomethyl, bromo or phenyl;

(g) when $R^1$, R and R' are H, $R^2$ is $CO_2H$ and $R^3$ is OH, then $R^4$ and $R^5$ are not chloro;

(h) when $R^1$, $R^4$ and R' are H, $R^2$ is $CO_2H$ and $R^3$ is OH, then R and $R^5$ are not bromo;

(i) when $R^1$, R, R' and $R^5$ are H, $R^2$ is $CO_2Me$ and $R^3$ is OH, then $R^4$ is not hydroxymethyl, phenyl or bromo;

(j) when $R^1$, R, $R^4$ and $R^5$ are H, $R^2$ is $CO_2Me$ and $R^3$ is OH, then R' is not 4-methoxyphenyl, 3-methylphenyl, pyridin-3-yl, benzyl, bromo, 4-chlorophenyl, 3,4-dichlorophenyl, 3-hydroxypropyl or 3-tert-butoxycarbonylaminopropyl;

(k) when $R^1$, R, $R^4$ and R' are H, $R^2$ is $CO_2Me$ and $R^3$ is OH, then $R^5$ is not phenyl or 3-tert-butoxycarbonylaminoprop-1-yl;

(l) when $R^1$, R, $R^4$, R' and $R^5$ are H and $R^2$ is $CO_2Me$, then $R^3$ is not toluene-4-sulphonylamino, piperazin-1-yl, morpholin-1-yl, piperidin-1-yl, 4-methylpiperazin-1-yl, 3-benzoylaminoprop-1-yl, phenethyl, 3-tert-butoxycarbonylaminopropyl, 3-hydroxypropyl, amino or hex-1-yl;

(m) when $R^1$, $R^4$, R' and $R^5$ are H, $R^2$ is $CO_2Na$ and $R^3$ is OH, then R is not phenyl;

(n) when $R^1$, R, $R^4$, R' and $R^5$ are H and $R^2$ is $CO_2H$, then $R^3$ is not phenyl, 4-chlorophenyl, phenethyl, 3-hydroxypropyl, amino, morpholin-1-yl, piperidin-1-yl, 4-methylpiperazin-1-yl, toluene-4-sulphonylamino, 3-benzoylaminoprop-1-yl, aminoprop-1-ynyl, hex-1-yl, 5-hydroxypent-1-yl, piperazin-1-yl or 2-(1-piperazinyl)pyrimidinyl;

(o) when $R^1$, R' and R are H, $R^2$ is $CO_2Me$ and $R^3$ is OH, then $R^4$ and $R^5$ are not chloro;

(p) when $R^1$, $R^4$, R' and $R^5$ are H, $R^2$ is $CO_2Me$ and $R^3$ is OH, then R is not bromo;

(q) when $R^1$, R' and $R^4$ are H, $R^2$ is $CO_2Me$ and $R^3$ is OH, then R and $R^5$ are not bromo;

(r) when $R^1$, R, $R^3$, R' and $R^5$ are H and $R^2$ is $CO_2H$, then $R^4$ is not phenyl, 4-chlorophenyl or phenylethyl;

(s) when $R^1$, $R^5$, R', $R^4$, $R^3$ and R are H, then $R^2$ is not 2H-tetrazol-1-yl;

(t) when $R^1$, $R^5$, $R^4$ and R are H, $R^2$ is $CO_2H$ and $R^3$ is OH, then R' is not 3,5-dichlorophenyl or 4-fluorophenyl; and (u) at least one of $R^1$ to $R^5$, R and R' is other than H.

Useful compounds of Formula II are as follows:

(i) Formula III

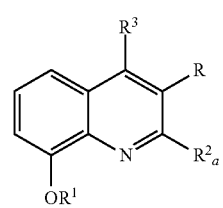

(III)

in which:

R, $R^1$ and $R^3$ are as defined in Formula II above; and $R^2_a$ is H; optionally substituted $C_{1-6}$ alkyl; optionally substituted $C_{1-6}$ alkenyl; optionally substituted aryl; optionally substituted heterocyclyl; an antioxidant; a targeting moiety; $COR^6_a$ or $CSR^6_a$ in which $R^6_a$ is H, optionally substituted $C_{1-6}$ alkyl, optionally substituted $C_{2-6}$ alkenyl, hydroxy, optionally substituted aryl, optionally substituted heterocyclyl or $OR^7{}_a$, $SR^7{}_a$ or $NR^7{}_aR^8{}_a$ in which $R^7{}_a$ and $R^8{}_a$ are either the same or different and selected from H, optionally substituted $C_{1-6}$ alkyl, optionally substituted $C_{2-6}$ alkenyl, optionally substituted aryl or optionally substituted heterocyclyl; CN; $CH_2NR^9{}_aR^{10}{}_a$, $HCNOR^9{}_a$ or $HCNNR^9{}_aR^{10}$ in which $R^9{}_a$ and $R^{10}{}_a$ are either the same or different and selected from H, optionally substituted $C_{1-6}$ alkyl, optionally substituted $C_{2-6}$ alkenyl, optionally substituted aryl or optionally substituted heterocyclyl; $OR^{11}{}_a$, $SR^{11}{}_a$ or $NR^{11}{}_aR^{12}{}_a$ in which $R^{11}{}_a$ and $R^{12}{}_a$ are either the same or different and selected from H, optionally substituted $C_{1-6}$ alkyl, optionally substituted $C_{2-6}$ alkenyl, optionally substituted aryl or optionally substituted heterocyclyl or together form optionally substituted heterocyclyl; or $SO_2NR^{13}{}_aR^{14}{}_a$ in which $R^{13}{}_a$ and $R^{14}{}_a$ are either the same or different and selected from H or optionally substituted $C_{1-6}$ alkyl, optionally substituted $C_{2-6}$ alkenyl, optionally substituted aryl or optionally substituted heterocyclyl.

Preferred compounds of Formula III are as follows:
Formula IV

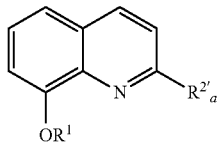

(IV)

in which:
$R^1$ is as defined in Formula II above; and
$R^{2'}{}_a$ is optionally substituted $C_{1-6}$ alkyl, optionally substituted $C_{2-6}$ alkenyl, optionally substituted aryl or optionally substituted heterocyclyl.

Formula IV may represent compounds in which an antioxidant moiety is attached to the C2 position of the 8-hydroxyquinoline in such a way that exposure to a prooxidative environment, that is, hydroxy radicals, will result in a molecule with enhanced metal binding properties.

Representative examples are shown below:

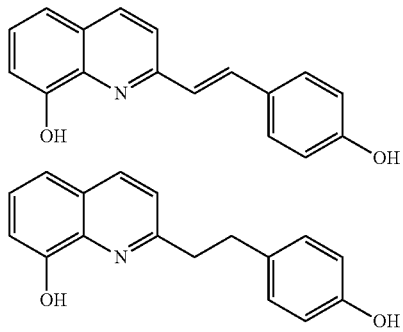

Formula V

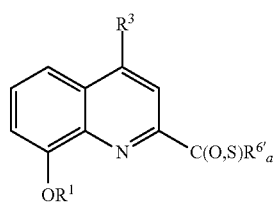

(V)

in which:
$R^1$ and $R^3$ are as defined in Formula II above; and
$R^{6'}{}_a$ is optionally substituted $C_{1-6}$ alkyl, optionally substituted $C_{2-6}$ alkenyl, hydroxy, $SR^{7'}{}_a$, $N_2R^{7'}{}_aR^{8'}{}_a$, or $NR^{7'}{}_aR^{8'}{}_a$ in which $R^{7'}{}_a$ and $R^{8'}{}_a$ are either the same or different and selected from H, optionally substituted $C_{1-6}$ alkyl, optionally substituted aryl or optionally substituted heterocyclyl.

Formula V represents compounds in which a hydrophilic amide moiety is attached to the C2 position of the 8-hydroxyquinoline so as to generally enhance solubility while maintaining membrane permeability.

Representative examples are shown below:

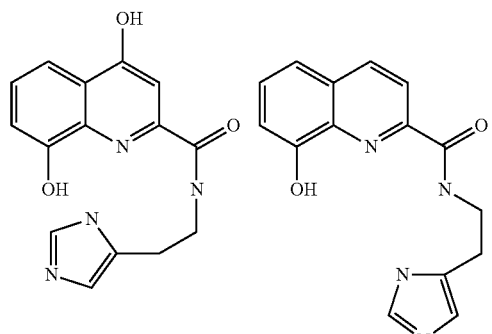

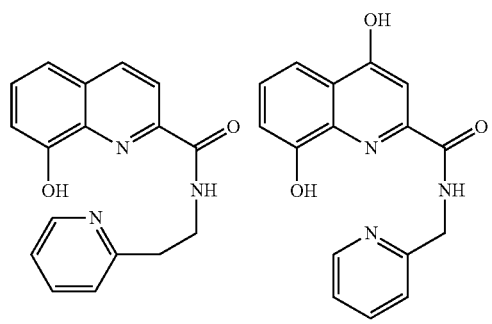

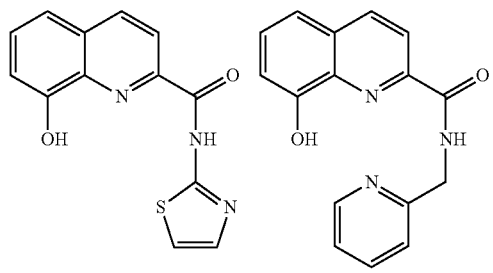

Formula VI

(VI)

in which:
$R^1$ is as defined in Formula II above; and
$R^{2''}{}_a$ is CN; $CH_2NR^{9'}{}_aR^{10'}{}_a$, $HCNOR^{9'}{}_a$ or $HCNNR^{9'}{}_aR^{10'}{}_a$ in which $R^{9'}{}_a$ and $R^{10'}{}_a$ are either the same or different and selected from H, optionally substituted $C_{1-6}$ alkyl, optionally substituted alkenyl, optionally substituted aryl or optionally substituted heterocyclyl.

Representative examples are shown below:

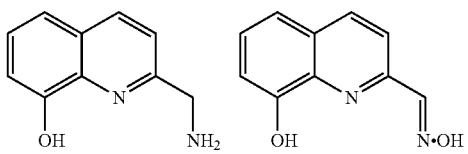

Formula VII

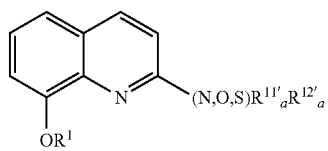

(VII)

in which:
$R^1$ is as defined in Formula II above; and
$R^{11'}_a$ and $R^{12'}_a$ are either the same or different and selected from H, optionally substituted $C_{1-6}$ alkyl, optionally substituted $C_{2-6}$ alkenyl, optionally substituted aryl and optionally substituted heterocyclyl or together form optionally substituted heterocyclyl.

Formula VIII

(VIII)

in which:
$R^1$ is as defined in Formula II above; and
$R^{13'}_a$ and $R^{14'}_a$ are either the same or different and selected from H, optionally substituted $C_{1-6}$ alkyl, optionally substituted $C_{2-6}$ alkenyl, optionally substituted aryl or optionally substituted heterocyclyl.

(ii) Formula IX

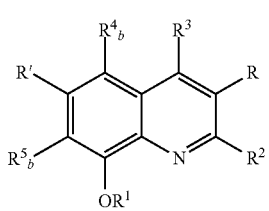

(IX)

in which:
$R^1$, R', R, $R^2$ and $R^3$ are as defined in Formula II above;
$R^4_b$ and $R^5_b$ are either the same or different and selected from H; optionally substituted $C_{1-6}$ alkyl; optionally substituted $C_{2-6}$ alkenyl; halo; CN; $CF_3$; optionally substituted aryl; optionally substituted heterocyclyl; an antioxidant; a targeting moiety; $SO_3H$; $SO_2NR^{13}_a R^{14}_a$ in which $R^{13}_a$ and $R^{14}_a$ are as defined in Formula III above; or $OR^{15}_b$, $SR^{15}_b$, $SO_2R^{15}_b$, $CONR^{15}_b R^{16}_b$ or $NR^{15}_b R^{16}_b$ in which $R^{15}_b$ and $R^{16}_b$ are either the same or different and selected from H, optionally substituted $C_{1-6}$ alkyl, optionally substituted $C_{2-6}$ alkenyl, optionally substituted $C_{1-6}$ acyl, optionally substituted aryl or optionally substituted heterocyclyl,
including provisos (a) to (c), (e), (g), (h), (I), (k), (o), (q), (r), and (u) as defined above.

Useful compounds of Formula IX are as follows:

Formula X

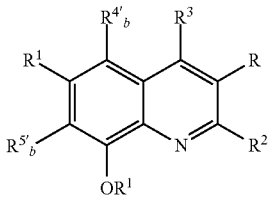

(X)

in which:
$R^1$, R', R, $R^2$ and $R^3$ are as defined in Formula II above; and
$R^{4'}_b$ and $R^{5'}_b$ are as defined in Formula IX above provided that at least one is halo,
including provisos (a), (c), (g), (h), (i), (o), (q) and (u) defined above.

Formula XI

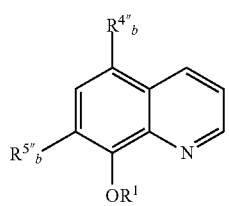

(XI)

in which:
$R^1$ is as defined in Formula II above;
$R^{4''}_b$ is H or halo; and
$R^{5''}_b$ is optionally substituted aryl or optionally substituted heterocyclyl.

A representative example is shown below.

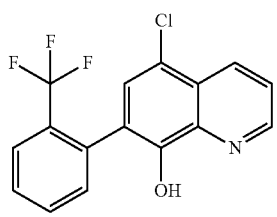 [SMILES: Oc1c(-c2ccccc2C(F)(F)F)cc(Cl)c2cccnc12]

Formula XII

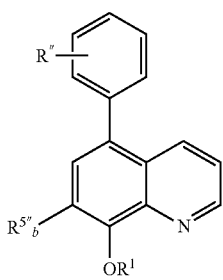

(XII)

in which:
$R^1$ is as defined in Formula II above;
R" is $C_{1-6}$ alkoxy, halo, $C_{1-6}$ alkyl, $C_{2-6}$ alkenyl or $C_{1-6}$ haloalkyl; and
$R^{5''}_b$ is H or halo.

A representative example is shown below.

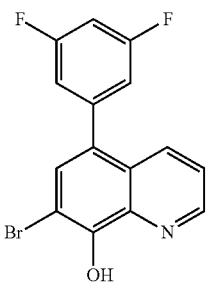 [SMILES: Oc1c(Br)cc(-c2cc(F)cc(F)c2)c2cccnc12]

Formula XIII

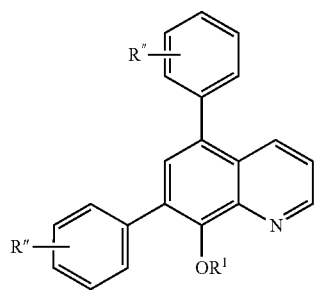

(XIII)

in which
R¹ is as defined in Formula II above; and
R" is as defined in Formula XIII above,
Formula XIV

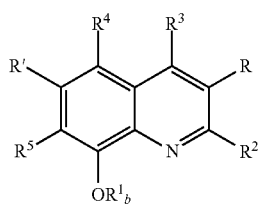

(XIV)

in which:
R² to R⁵, R and R' are as defined in Formula II above; and
$R^1{}_b{}''$ is optionally substituted $C_{1-6}$ alkyl, optionally substituted aryl, optionally substituted aryl acyl, $C_{1-6}$ alkyl acyl or optionally substituted heterocyclyl.

(iii) Formula XV

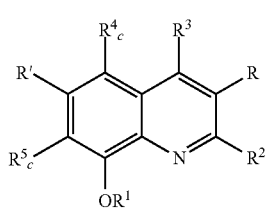

(XV)

in which:
$R^1, R^2, R^3$, R and R' are as defined in Formula II; and
at least one of $R^4{}_c$ and $R^5{}_c$ is halo and the other is selected from H, optionally substituted alkyl, optionally substituted alkenyl, optionally substituted alkoxy, optionally substituted acyl, hydroxy, optionally substituted amino, optionally substituted thio, optionally substituted sulphonyl, optionally substituted sulphinyl, optionally substituted sulphonylamino, $SO_3H$, amine, CN, $CF_3$, optionally substituted aryl, optionally substituted heterocyclyl, an antioxidant and a targeting moiety, salts, hydrates, solvates, derivatives, pro-drugs, tautomers and/or isomers thereof
with the provisos that:
(a) when $R^1$ to $R^3$, R and R' are H, then $R^4{}_c$ is not chloro or iodo and $R^5{}_c$ is not iodo;
(b) when $R^1, R^5{}_c$, R' and R are H, $R^2$ is $CO_2H$ and $R^3$ is OH, then $R^4{}_c$ is not bromo;
(c) when $R^1$, R and R' are H, $R^2$ is $CO_2H$ and $R^3$ is OH, then $R^4{}_c$ and $R^5{}_c$ are not chloro;
(d) when $R^1$, $R^4{}_c$ and R' are H, $R^2$ is $CO_2H$ or $CO_2Me$ and $R^3$ is OH, then R and $R^5{}_c$ are not bromo;
(e) when $R^1$, R, R' and $R^5{}_c$ are H, $R^2$ is $CO_2Me$ and $R^3$ is OH, then $R^4{}_c$ is not bromo; and
(f) when $R^1$, R and R' are H, $R^2$ is $CO_2Me$ and $R^3$ is OH, then $R^4{}_c$ and $R^5{}_c$ are not chloro.

A preferred compound of Formula XV is as follows:
Formula XVI

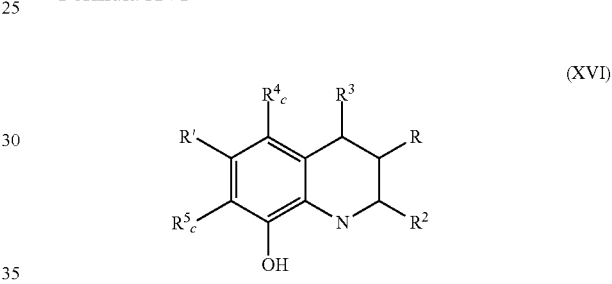

(XVI)

in which:
$R^2$, R, R', $R^4{}_c$ and $R^5{}_c$ are as defined in Formula XVI; and
$R^{3'}$ is H, optionally substituted alkyl, optionally substituted alkenyl, optionally substituted alkoxy, optionally substituted acyl, optionally substituted amino, optionally substituted thio, optionally substituted sulphonyl, optionally substituted sulphinyl, optionally substituted sulphonylamino, halo, $SO_3H$, amine, CN, $CF_3$, optionally substituted aryl, optionally substituted heterocyclyl, an antioxidant or a targeting moiety,
with the proviso that at least one of R, $R^2$ and $R^{3'}$ is other than H.

Representative examples are shown below:

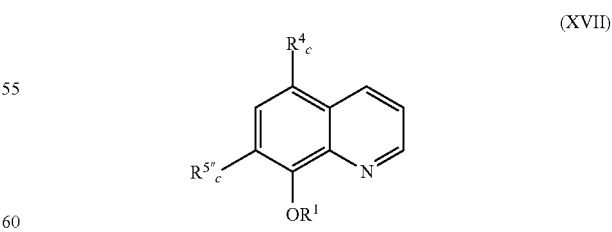

(XVII)

in which:
$R^1$ is as defined in Formula II and $R^4{}_c$ is as defined in Formula XV; and
$R^5{}_c{}''$ is optionally substituted aryl or optionally substituted heterocyclyl;

Formula XVIII

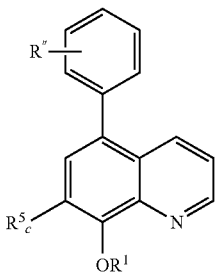

(XVIII)

in which:
R¹ is as defined in Formula II, $R^5{}_c$ is as defined in Formula XV and R" is as defined in Formula XII; and Formula XIX

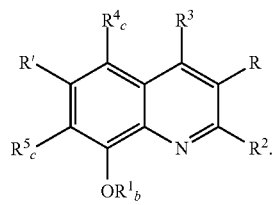

(XIX)

in which:
R², R³, R and R' are as defined in Formula II, $R^4{}_c$ and $R^5{}_c$ are as defined in Formula XV and $R^1{}_b$ is as defined in Formula XII.

Other examples of compounds contemplated herein include:

PBT 1038

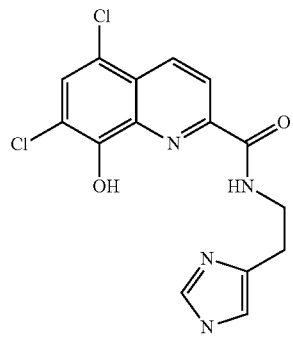

PBT 1050

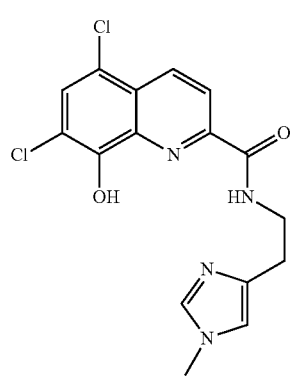

PBT 1052

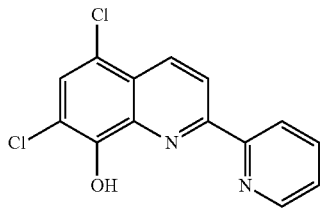

PBT 1033

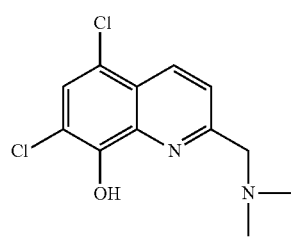

PBT 1056

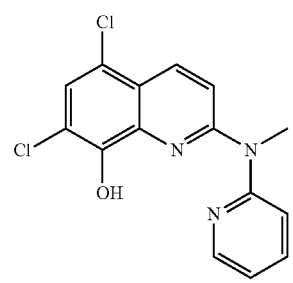

PBT 1051

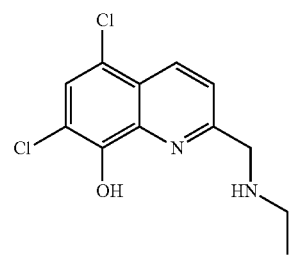

PBT 1058

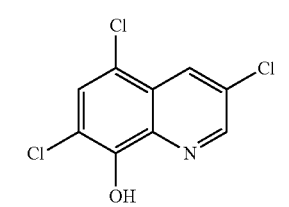

PBT 1060

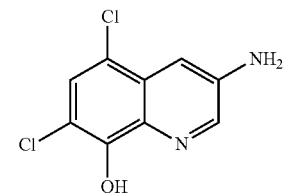

The present invention also provides a compound of Formula XX which is a compound of Formula II with the provisos that:

(a) when $R^1$ and $R^3$ to $R^5$, R and R' are H, then $R^2$ is not H, methyl,

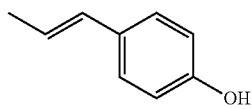

$CO_2H$, CN, $CONCH_2CO_2H$, $COCH_3$, $CH_2NH_2$, CNOH, (pyrid-2-yl), 2-hydroxyphenyl, $CHNNH_2$, NH-(pyrid-2-yl),

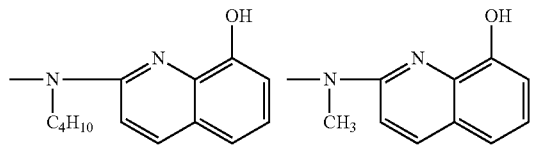

or $SO_3H$;

(b) when $R^1$ and $R^4$ to $R^7$ are H, then $R^3$ is not OH and $R^2$ is not $CO_2H$;

(c) when $R^1$ to $R^3$, $R^6$ and $R^7$ are H, then (i) when $R^5$ is I, $R^4$ is not Cl, $SO_3H$ or I; (ii) when $R^5$ is H, $R^4$ is not $SO_3H$, $NH_2$ or Cl; (iii) $R^4$ and $R^5$ are both not Cl, Br or $CH_3$; and (iv) when $R^2$ to $R^7$ are H, then $R^1$ is not

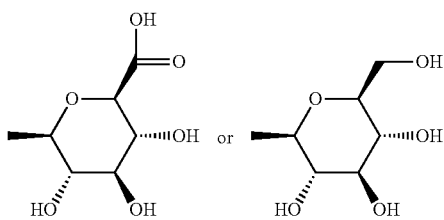

(d) when R1 to $R^3$, R and R' are H, then $R^4$ is not Cl or I and $R^5$ is not I;

(e) when R1 to $R^3$, R, R' and $R^5$ are H, then $R^4$ is not CHO, $CHOHCCl_3$,

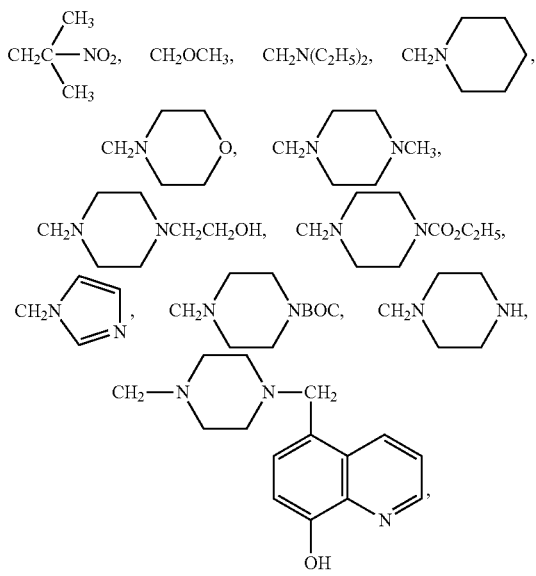

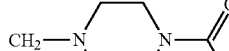, $CH_2CN$,

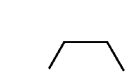

(f) when $R^1$, $R^5$, R' and R are H, $R^2$ is $CO_2H$ and $R^3$ is OH, then $R^4$ is not bromo, methyl, phenyl, hydroxymethyl or trifluoromethyl;

(g) when $R^1$, $R^4$, $R^5$ and R are H, $R^2$ is $CO_2H$ and $R^3$ is OH, then R' is not bromo, iodo, methyl, phenyl, propyl, phenethyl, heptyl, benzylaminomethyl, 3-aminopropyl, 3-hydroxypropyl, 4-methoxyphenyl, 3-methylphenyl, 4-chlorophenyl, 3,4-dichlorophenyl, pyridin-3-yl, furo-2-yl, 4-chlorophenyl, 3,4-dichlorophenyl, 2-chlorophenyl, 3-chlorophenyl, 2-chlorophenyl, 3-chlorophenyl, 2-methoxyphenyl or piperidin-2-yl;

(h) when $R^1$, $R^4$, R and R' are H, $R^2$ is $CO_2H$ and $R^3$ is OH, then $R^5$ is not phenyl, 3-hydroxypropyl, phenethyl, 3-aminoprop-1-yl or hex-1-yl;

(i) when $R^1$, $R^4$, R' and $R^5$ are H, $R^2$ is $CO_2H$ and $R^3$ is OH, then R is not N-morpholinomethyl, bromo or phenyl;

(j) when $R^1$, R and R' are H, $R^2$ is $CO_2H$ and $R^3$ is OH, then $R^4$ and $R^5$ are not chloro;

(k) when $R^1$, $R^4$ and R' are H, $R^2$ is $CO_2H$ and $R^3$ is OH, then R and $R^5$ are not bromo;

(l) when $R^1$, R, R' and $R^5$ are H, $R^2$ is $CO_2Me$ and $R^3$ is OH, then $R^4$ is not hydroxymethyl, phenyl or bromo;

(m) when $R^1$, R, $R^4$ and $R^5$ are H, $R^2$ is $CO_2Me$ and $R^3$ is OH, then R' is not 4-methoxyphenyl, 3-methylphenyl, pyridin-3-yl, benzyl, bromo, 4-chlorophenyl, 3,4-dichlorophenyl, 3-hydroxypropyl or 3-tert-butoxycarbonylaminopropyl;

(n) when $R^1$, R, $R^4$ and R' are H, $R^2$ is $CO_2Me$ and $R^3$ is OH, then $R^5$ is not phenyl or 3-tert-butoxycarbonylaminoprop-1-yl;

(o) when $R^1$, R, $R^4$, R' and $R^5$ are H and $R^2$ is $CO_2Me$, then $R^3$ is not toluene-4-sulphonylamino, piperazin-1-yl, morpholin-1-yl, piperidin-1-yl, 4-methylpiperazin-1-yl, 3-benzoylaminoprop-1-yl, phenethyl, 3-tert-butoxycarbonylaminopropyl, 3-hydroxypropyl, amino or hex-1-yl;

(p) when $R^1$, $R^4$, R' and $R^5$ are H, $R^2$ is $CO_2Na$ and $R^3$ is OH, then R is not phenyl;

(q) when $R^1$, R, $R^4$, R' and $R^5$ are H and $R^2$ is $CO_2H$, then $R^3$ is not phenyl, 4-chlorophenyl, phenethyl, 3-hydroxypropyl, amino, morpholin-1-yl, piperidin-1-yl, 4-methylpiperazin-1-yl, toluene-4-sulphonylamino, 3-benzoylaminoprop-1-yl, aminoprop-1-ynyl, hex-1-yl, 5-hydroxypent-1-yl, piperazin-1-yl or 2-(1-piperazinyl)pyrimidinyl;

(r) when $R^1$, R' and R are H, $R^2$ is $CO_2Me$ and $R^3$ is OH, then $R^4$ and $R^5$ are not chloro;

(s) when $R^1$, $R^4$, R' and $R^5$ are H, $R^2$ is $CO_2Me$ and $R^3$ is OH, then R is not bromo;

(t) when $R^1$, R' and $R^4$ are H, $R^2$ is $CO_2Me$ and $R^3$ is OH, then R and $R^5$ are not bromo;

(u) when $R^1$, R, $R^3$, R' and $R^5$ are H and $R^2$ is $CO_2H$, then $R^4$ is not phenyl, 4-chlorophenyl or phenylethyl;

(v) when $R^1$, $R^5$, R', $R^4$, $R^3$ and R are H, then $R^2$ is not 2H-tetrazol-1-yl;

(w) when $R^1$, $R^5$, $R^4$ and R are H, $R^2$ is $CO_2H$ and $R^3$ is OH, then R' is not 3,5-dichlorophenyl or 4-fluorophenyl; and (x) at least one of $R^1$ to $R^5$, R and R' is other than H;

(y) when $R^1$ to $R^3$, $R^5$, R' and R are H, then $R^4$ is not chloro, $NH_2$ or $SO_3H$; and (z) when $R^1$, $R^3$ to $R^5$, R and R' are H, then $R^2$ is not $CH_3$.

Preferably, the invention provides a compound of Formula Ic, with the additional provisos that:

(g) when $R^1$ to $R^3$, R and R' are H, then $R^4_c$ and $R^5_c$ are both not chloro or bromo; and (h) when $R^1$ to $R^3$, $R^5_c$, R and R' are H, then $R^4_c$ is not chloro.

Particularly preferred compounds include a series of so called "PB" (or PBT) compounds, some of which are referred to above, such as:

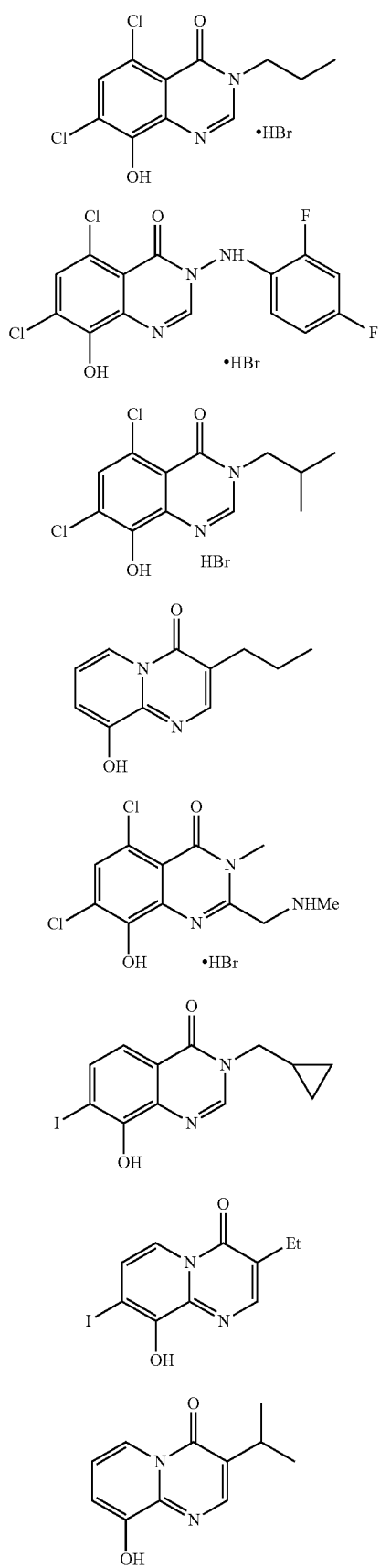
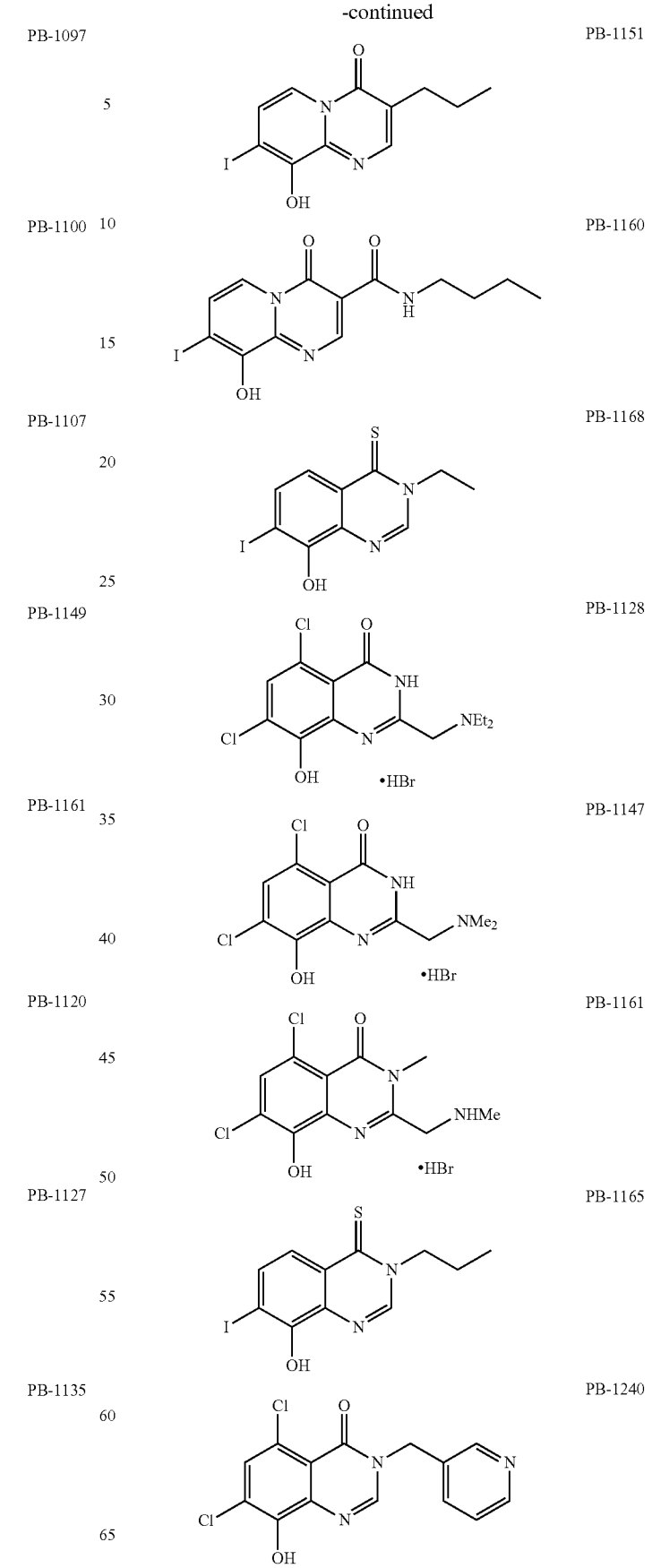

PB-1241
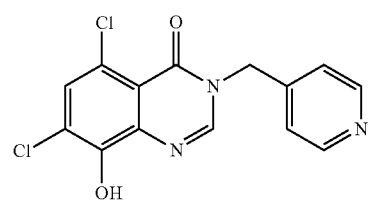

PB-1243
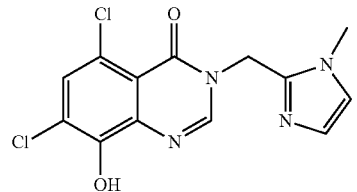

PB-1244
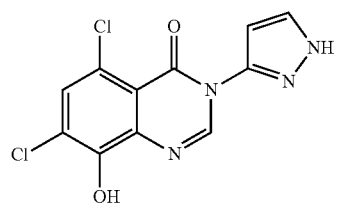

PB-1249
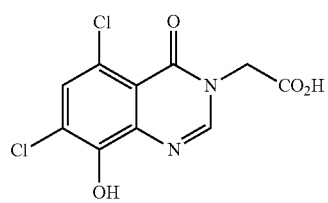

PB-1252
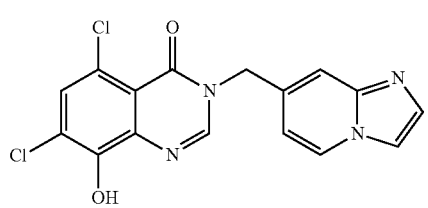

PB-1253
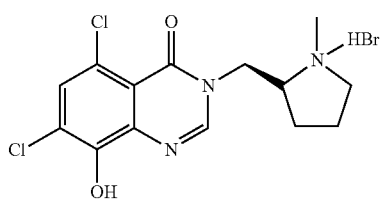

PB-1254
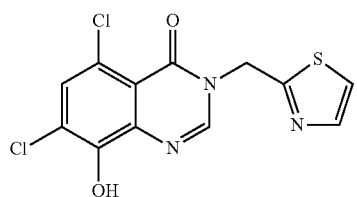

PB-1255
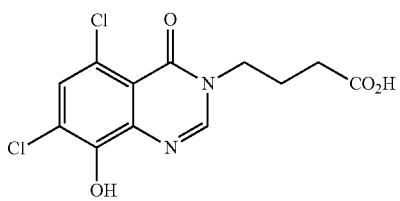

PB-1256
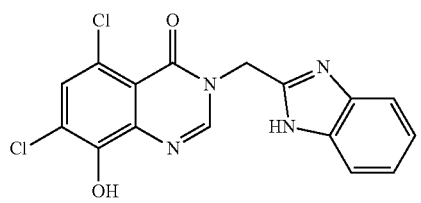

PB-1262
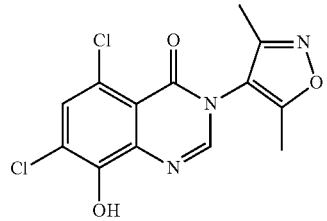

PB-1264
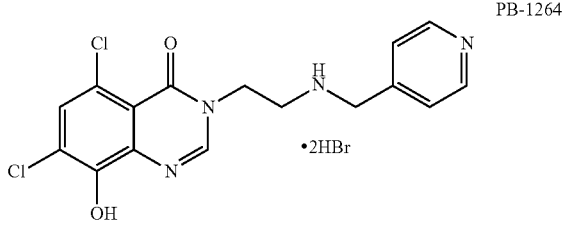

PB-1267
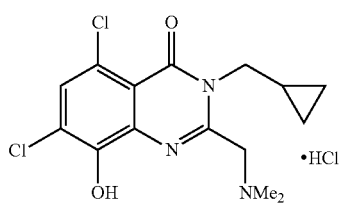

PB-1268
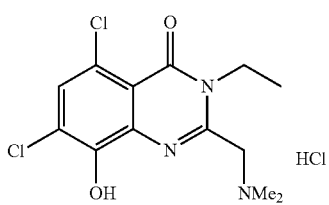

PB-1269
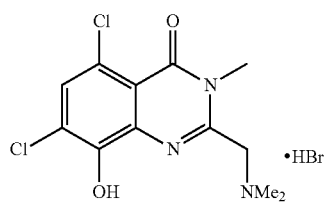

The 8-hydroxyl or 8-mercapto group on the above compounds may be blocked to form a prodrug, in particular an ester prodrug. The 8-hydroxy or 8-mercapto represents a principal site of metabolism for the above compounds: conjugation with glucuronic acid or sulphate gives a hydrophilic species ready to be excreted.

Other useful compounds include a compound of Formula XXI:

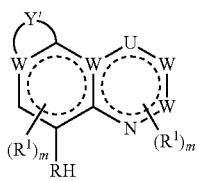

(XXI)

in which:
R, R$^1$ and m are as defined for Formula I;
W is CH, N or NH;
U is CH, CO or N; and
Y', together with the ring to which it is attached forms a 6 membered N-containing optionally substituted heterocyclyl.

Preferred compounds of Formula XXI are as follows:
(i) Formula XXII

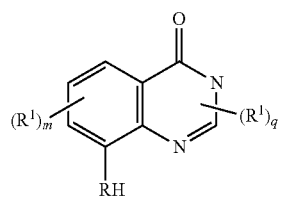

(XXII)

in which R, R$^1$, m and q are as for Formula I.

Preferably R$^1$ is located at positions 2, 3, 5 and/or 7 and is selected from halo, optionally substituted aryl, optionally substituted heterocyclyl, optionally substituted alkyl and (CH$_2$)$_n$NR$^2$R$^3$ in which n, R$^2$ and R$^3$ are as defined above. More preferably R$^1$ is chlorine, optionally substituted phenyl, C$_{2-6}$ cycloalkyl, CH$_2$NR$^4$R$^5$ in which R$^4$ and R$^5$ are independently selected from H and C$_{1-4}$ alkyl or optionally substituted pyridinyl.

Particularly examples are shown below.

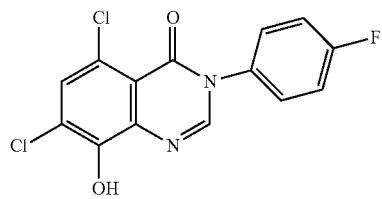

1055

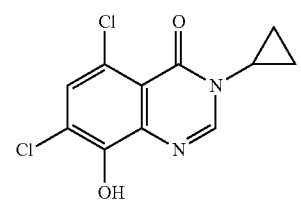

1061

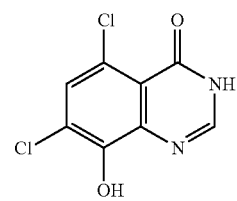

1067

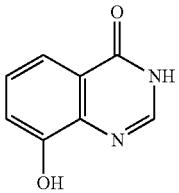

1049

(ii) Formula XXIII

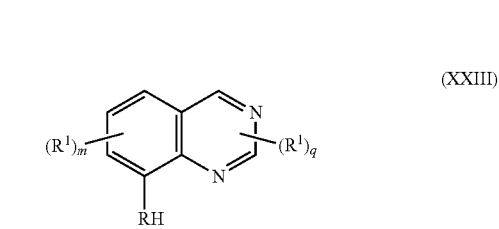

(XXIII)

in which R, R$^1$, m and q are as defined for Formula I.

R$^1$ may be is located at positions 2, 4, 5 and/or 7 and is selected from halo and optionally substituted heterocyclyl. Preferably, R$^1$ is chloro and/or morpholinyl.

Preferred examples are shown below.

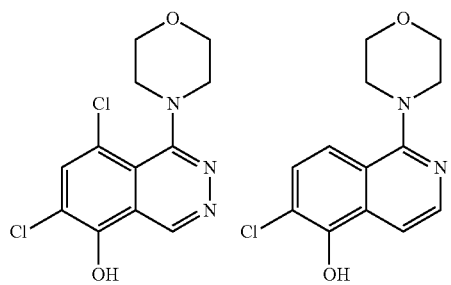

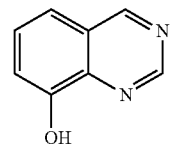 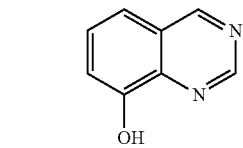

(iii) Formula XXIV

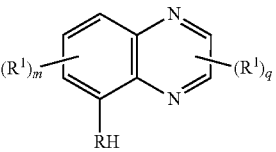

(XXIV)

in which R, R$^1$, m and q are as defined for Formula I.

Preferably R$^1$ is located at positions 2, 5 and/or 7 and is selected from halo and CH$_2$NR$^4$R$^5$ in which R$^4$ and R$^5$ are independently selected from H and C$_{1-4}$ alkyl.

Useful examples are shown below.

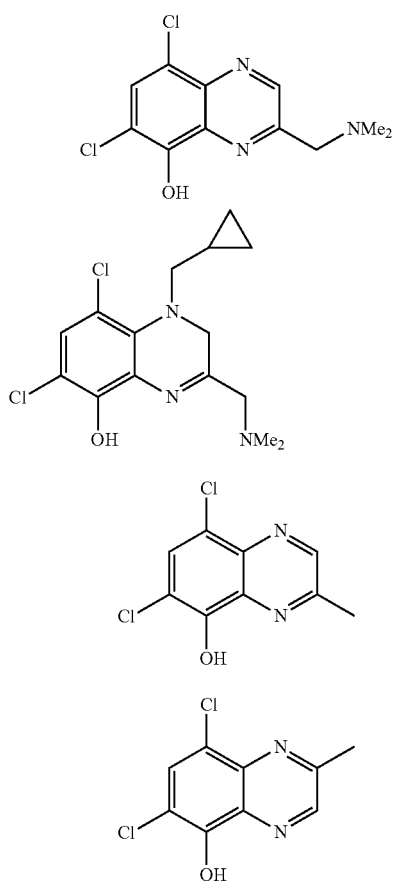

(iv) Formula XXV

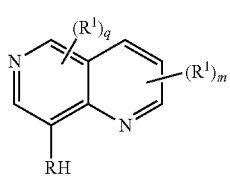

(XXV)

in which R, R$^1$, m and q are as defined for Formula I.

Preferably R$^1$ is located at positions 2 and/or 7 and is selected from optionally substituted heterocyclyl, CO$_2$R$^2$, (CH$_2$)$_n$NR$^2$R$^3$ and CONR$^2$R$^3$ in which n, R$^2$ and R$^3$ are as defined in Formula I.

Preferred examples are shown below.

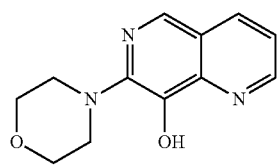

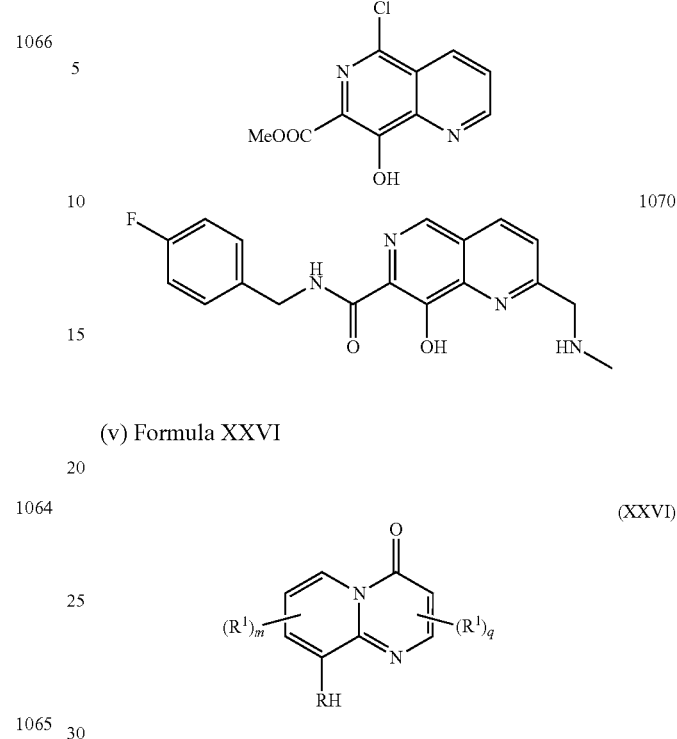

(v) Formula XXVI

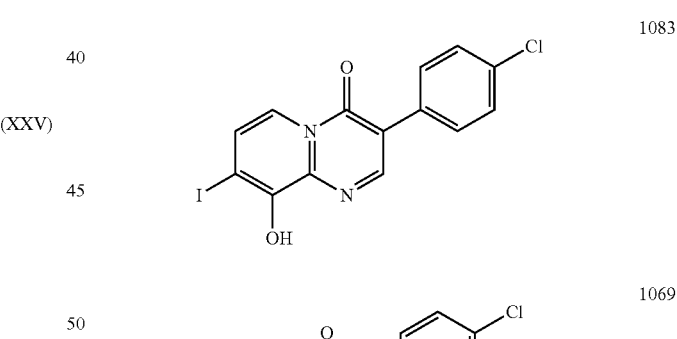

(XXVI)

in which R, R$^1$, m and q are as defined for Formula I.

Preferably R$^1$ is located at positions 2, 3, 6 and/or 7 and is selected from halo, optionally substituted aryl and (CH$_2$)$_n$NR$^2$R$^3$ in which n, R$^2$ and R$^3$ are as defined for Formula I.

Preferred examples are shown below.

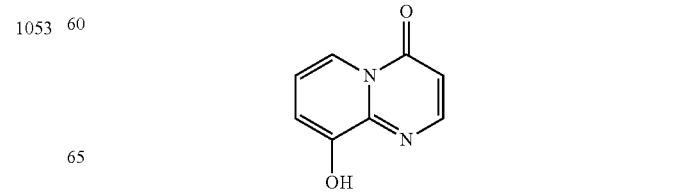

(vi) Formula XXVII

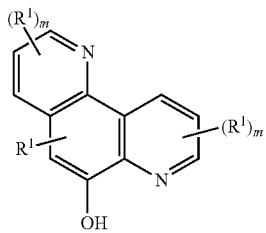

(XXVII)

in which $R^1$ and m are as defined for Formula I.

Preferably $R^1$ is located at positions 2 and/or 7 and is selected from halo and $(CH_2)_nNR^2R^3$ in which n, $R^2$ and $R^3$ are as defined above.

Useful examples are shown below.

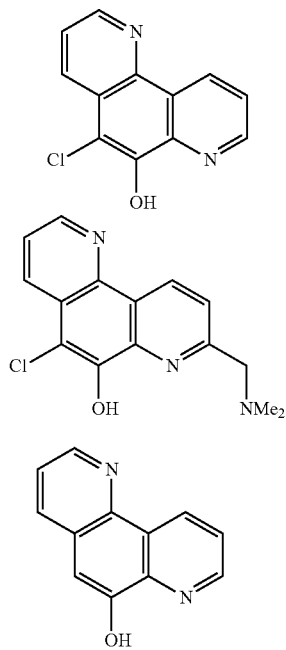

1026

Reference to the above listed compounds includes their pharmaceutically acceptable salts and isomers.

The term "alkyl" used either alone or in compound words such as "optionally substituted alkyl" or "alkylamino" refers to straight chain, branched chain or cyclic hydrocarbon groups having from 1 to 10 carbon atoms, preferably 1 to 6 carbon atoms, more preferably 1 to 4 carbon atoms. Illustrative of such alkyl groups are methyl, ethyl, propyl, isopropyl, butyl, isobutyl, sec-butyl, tert-butyl, pentyl, neopentyl, hexyl, cyclopropyl, cyclobutyl, cyclopentyl or cyclohexyl. Preferred alkyl groups are $C_{1-4}$ alkyl such as methyl or ethyl and $C_{2-6}$ cycloalkyl such as cyclopropyl.

The term "alkenyl" used either alone or in compound words such as "optionally substituted alkenyl", denotes linear, branched or mono- or poly-cyclic radicals having at least one carbon-carbon double bond of 2 to 20 carbon atoms, preferably 2 to 14 carbon atoms, more preferably 2 to 6 carbon atoms. Examples of alkenyl radicals include allyl, ethenyl, propenyl, butenyl, iso-butenyl, 3-methyl-2-butenyl, 1-pentenyl, cyclopentenyl, 1-methyl-cyclopentenyl, 1-hexenyl, 3-hexenyl, cyclohexenyl, 1-heptenyl, 3-heptenyl, 1-octenyl, cyclooctenyl, 1-nonenyl, 2-nonenyl, 3-nonenyl, 1-decenyl, 3-decenyl, 1,3-butadienyl, 1,4-pentadienyl, 1,3-cyclopentadienyl, 1,3-hexadienyl, 1,4-hexadienyl, 1,3-cyclohexadienyl, 1,4-cyclohexadienyl, 1,3-cycloheptadienyl, 1,3,5-cycloheptatrienyl, 1,3,5,7-cyclooctatetraenyl and the like.

The term "alkynyl" used either alone or in compound words such as "optionally substituted alkynyl" refers to straight chain or branched chain radicals having at least one carbon-carbon triple bond of 2 to 20 carbon atoms, preferably 2 to 14 carbon atoms, more preferably 2 to 6 carbon atoms. Examples include ethynyl, 1-propynyl, 1- and 2-butynyl, 2-methyl-2-propynyl, 2-pentynyl, 3-pentynyl, 4-pentynyl, 2-hexynyl, 3-hexynyl, 4-hexynyl, 5-hexynyl, 10-undecynyl, 4-ethyl-1-octyn-3-yl, 7-dodecynyl, 9-dodecynyl, 10-dodecynyl, 3-methyl-1-dodecyn-3-yl, 2-tridecynyl, 11-tridecynyl, 3-tetradecynyl, 7-hexadecynyl, 3-octadecynyl and the like.

The term "heterocyclyl group" used either alone or in compound words such as "optionally substituted heterocyclyl" refers to monocycle or polycyclic heterocyclic groups containing at least one heteroatom atom selected from nitrogen, sulphur and oxygen.

Suitable heterocyclic groups include N-containing heterocyclic groups, such as, unsaturated 3 to 6-membered heteromonocyclic groups containing 1 to 4 nitrogen atoms, for example, pyrrolyl, pyrrolinyl, imidazolyl, pyrazolyl, pyridyl, pyridinyl, pyrimidinyl, pyrazinyl, pyridazinyl, triazolyl or tetrazolyl;

saturated 3 to 6-membered heteromonocyclic groups containing 1 to 4 nitrogen atoms, such as, pyrrolidinyl, imidazolidinyl, piperidino or piperazinyl;

unsaturated condensed heterocyclic groups containing 1 to 5 nitrogen atoms, such as indolyl, isoindolyl, indolizinyl, benzimidazolyl, quinolyl, isoquinolyl, indazolyl, benzotriazolyl or tetrazolopyridazinyl;

unsaturated 3 to 6-membered heteromonocyclic group containing an oxygen atom, such as, pyranyl or furyl;

unsaturated 3 to 6-membered heteromonocyclic group containing 1 to 2 sulphur atoms, such as, thienyl;

unsaturated 3 to 6-membered heteromonocyclic group containing 1 to 2 oxygen atoms and 1 to 3 nitrogen atoms, such as, oxazolyl, isoxazolyl or oxadiazolyl;

saturated 3 to 6-membered heteromonocyclic group containing 1 to 2 oxygen atoms and 1 to 3 nitrogen atoms, such as, morpholinyl;

unsaturated condensed heterocyclic group containing 1 to 2 oxygen atoms and 1 to 3 nitrogen atoms, such as, benzoxazolyl or benzoxadiazolyl;

unsaturated 3 to 6-membered heteromonocyclic group containing 1 to 2 sulphur atoms and 1 to 3 nitrogen atoms, such as, thiazolyl or thiadiazolyl;

saturated 3 to 6-membered heteromonocyclic group containing 1 to 2 sulphur atoms and 1 to 3 nitrogen atoms, such as, thiazolidinyl; and unsaturated condensed heterocyclic group containing 1 to 2 sulphur atoms and 1 to 3 nitrogen atoms, such as, benzothiazolyl or benzothiadiazolyl.

Preferably the heterocyclyl is an unsaturated 5 or 6-membered heteromonocyclic group containing 1 to 3 nitrogen atoms such as imidazolyl or pyridinyl; a saturated 5 or 6-membered heteromonocyclic group containing 1 to 4 nitrogen atoms such as imidazolidinyl or piperazinyl; or a saturated 5 or 6-membered heteromonocyclic group containing 1 to 2 oxygen atoms and 1 to 3 nitrogen atoms such as morpholinyl.

The term "aryl" used either alone or in compound words such as "optionally substituted aryl" denotes a carbocyclic aromatic system containing one, two or three rings wherein such rings may be attached together in a pendent manner or may be fused. The term "aryl" embraces aromatic radicals such as phenyl, naphthyl, tetrahydronaphthyl, indane and biphenyl. Preferably, the aryl is optionally substituted phenyl such as 4-halophenyl, more preferably 4-fluorophenyl or 4-chlorophenyl.

The term "halo" refers to fluorine, chlorine, bromine or iodine, preferably fluorine, iodine or chlorine, most preferably chlorine.

The term "alkoxy" refers to straight chain or branched oxy-containing radicals preferably each having alkyl portions of 1 to about 6 carbon atoms. Examples of alkoxy include methoxy, ethoxy, propoxy, butoxy and tert-butoxy.

The term "optionally substituted thio" refers to optional substituents such as radicals containing a linear or branched alkyl of 1 to 10 carbon atoms, preferably 1 to 6 carbon atoms, more preferably 1 to 4 carbon atoms, attached to a divalent sulphur atom. Examples of alkylthio radicals include methylthio, ethylthio, propylthio, butylthio and hexylthio.

The term "optionally substituted" refers to a group which may or may not be further substituted with one or more groups selected from alkyl, alkenyl, alkynyl, aryl, aldehyde, halo, haloalkyl, haloalkenyl, haloalkynyl, haloaryl, hydroxy, alkoxy, alkenyloxy, aryloxy, benzyloxy, haloalkoxy, haloalkenyloxy, haloaryloxy, nitro, nitroalkyl, nitroalkenyl, nitroalkynyl, nitroaryl, nitroheterocyclyl, amino, alkylamino, dialkylamino, alkenylamino, alkynylamino, arylamino, diarylamino, benzylamino, dibenzylamino, acyl, alkenylacyl, alkynylacyl, arylacyl, acylamino, diacylamino, acyloxy, alkylsulphonyloxy, arylsulphenyloxy, heterocyclyl, heterocycloxy, heterocyclamino, haloheterocyclyl, alkylsulphenyl, arylsulphenyl, carboalkoxy, carboaryloxy, mercapto, alkylthio, benzylthio, acylthio, phosphorus-containing groups and the like. Preferably, the optional substituent is $C_{1-6}$ alkyl, more preferably $C_{1-4}$ alkyl; $CF_3$; fluorine; chlorine; iodine; cyano; $C_{1-6}$ alkoxy, more preferably $C_{1-4}$ alkoxy; aryl; heterocyclyl; amino; or alkylamino.

The term "antioxidant" is used herein in its broadest sense and refers to a group which has the capacity to react with a reactive oxygen species such as a hydroxyl radical in such a way as to generate a non toxic product. Examples include phenols such as 3,4,5-trimethoxyphenyl and 3,5-di-t-butyl-4-hydroxyphenyl, indole amines such as melatonin and flavonoids. Other examples may be found the literature (Wright et al, *J Am Chem Soc* 123:1173-1183, 2001).

The term "targeting moiety" is used herein in its broadest sense and refers to a group which will facilitate the brain delivery of the drug by way of an active transport mechanism. The targeting moiety is recognized by specific transporter enzymes integral to the blood brain barrier and these transporter enzymes then provide a mechanism for the drug to be imported into the brain. Typically such transporters are sodium dependant and their substrates contain carboxylic acids such as ascorbic acid and L-glutamate. Conjugation of the targeting moiety to the drug is enacted so as to retain the acid moiety.

The term "metal chelator" is used herein is distinguished from the previously known concept of "chelation therapy". "Chelation therapy" is a term associated clinically with the removal of bulk metals such as in Wilson's disease, β-thallesemia and haemochromatosis.

The salts of the above compounds are preferably pharmaceutically acceptable, but it will be appreciated that non-pharmaceutically acceptable salts also fall within the scope of the present invention, since these are useful as intermediates in the preparation of pharmaceutically acceptable salts. Examples of pharmaceutically acceptable salts include salts of pharmaceutically acceptable cations such as sodium, potassium, lithium, calcium, magnesium, ammonium and alkylammonium; acid addition salts of pharmaceutically acceptable inorganic acids such as hydrochloric, orthophosphoric, sulphuric, phosphoric, nitric, carbonic, boric, sulfamic and hydrobromic acids; or salts of pharmaceutically acceptable organic acids such as acetic, propionic, butyric, tartaric, maleic, hydroxymaleic, fumaric, citric, lactic, mucic, gluconic, benzoic, succinic, oxalic, phenylacetic, methanesulphonic, trihalomethanesulphonic, toluenesulphonic, benzenesulphonic, salicylic, sulphanilic, aspartic, glutamic, edetic, stearic, palmitic, oleic, lauric, pantothenic, tannic, ascorbic and valeric acids.

In addition, some of the compounds of the present invention may form solvates with water or common organic solvents. Such solvates are encompassed within the scope of the instant invention.

The term "pro-drug" is used herein in its broadest sense to include those compounds which are converted in vivo to the above compounds. Use of the pro-drug strategy optimises the delivery of the drug to its site of action, for example, the retina. In one aspect, the term refers to the presence of a $C_{1-6}$ alkyl or arylester moiety which is designed to resist hydrolysis until the pro-drug has crossed the BBB. In a second aspect, the term refers to the attachment at position 2 of an antioxidant group, in particular the 3,4,-5trimethoxyphenyl moiety or derivatives thereof. Exposure to the prooxidative environment of the retinal may then lead to hydroxylation of the 3,4,5-trimethoxyphenyl group to give a 2-hydroxy-3,4,5-trimethoxyphenyl substituent, the hydroxyl group of which acts to enhance the binding properties of the above compounds.

The term "tautomer" is used herein in its broadest sense to include the above compounds which are capable of existing in a state of equilibrium between two isomeric forms. Such compounds may differ in the bond connecting two atoms or groups and the position of these atoms or groups in the compound.

The term "isomer" is used herein in its broadest sense and includes structural, geometric and stereo isomers. As the above compounds may have one or more chiral centres, it is capable of existing in enantiomeric forms.

The compositions of the present invention comprise at least one of the above compounds together with one or more pharmaceutically acceptable carriers and optionally other therapeutic agents. Each carrier, diluent, adjuvant and/or excipient must be pharmaceutically "acceptable" in the sense of being compatible with the other ingredients of the composition and not injurious to the subject. Compositions include those suitable for oral, rectal, nasal, topical (including buccal and sublingual), vaginal or parenteral (including subcutaneous, intramuscular, intravenous and intradermal) administration. The compositions may conveniently be presented in unit dosage form and may be prepared by methods well known in the art of pharmacy. Such methods include the step of bringing into association the active ingredient with the carrier which constitutes one or more accessory ingredients. In general, the compositions are prepared by uniformly and intimately bringing into association the active ingredient with liquid carriers, diluents, adjuvants and/or excipients or finely divided solid carriers or both, and then if necessary shaping the product.

The above compounds may be administered orally, topically, or parenterally in dosage unit formulations containing conventional non-toxic pharmaceutically acceptable carriers, adjuvants, and vehicles. The term parenteral as used herein includes subcutaneous injections, aerosol for administration to lungs or nasal cavity, intravenous, intramuscular, intrathecal, intracranial, injection or infusion techniques. Intra-ocular administration is particularly useful.

The present invention also provides suitable topical, oral, and parenteral pharmaceutical formulations for use in the novel methods of treatment of the present invention. The compounds of the present invention may be administered orally as tablets, aqueous or oily suspensions, lozenges, troches, powders, granules, emulsions, capsules, syrups or elixirs. The composition for oral use may contain one or more agents selected from the group of sweetening agents, flavoring agents, colouring agents and preserving agents in order to produce pharmaceutically elegant and palatable preparations. Suitable sweeteners include sucrose, lactose, glucose, aspartame or saccharin. Suitable disintegrating agents include corn starch, methylcellulose, polyvinylpyrrolidone, xanthan gum, bentonite, alginic acid or agar. Suitable flavoring agents include peppermint oil, oil of wintergreen, cherry, orange or raspberry flavoring. Suitable preservatives include sodium benzoate, vitamin E, alphatocopherol, ascorbic acid, methyl paraben, propyl paraben or sodium bisulphite. Suitable lubricants include magnesium stearate, stearic acid, sodium oleate, sodium chloride or talc. Suitable time delay agents include glyceryl monostearate or glyceryl distearate. The tablets contain the active ingredient in admixture with non-toxic pharmaceutically acceptable excipients which are suitable for the manufacture of tablets.

These excipients may be, for example, (1) inert diluents, such as calcium carbonate, lactose, calcium phosphate or sodium phosphate; (2) granulating and disintegrating agents, such as corn starch or alginic acid; (3) binding agents, such as starch, gelatin or acacia; and (4) lubricating agents, such as magnesium stearate, stearic acid or talc. These tablets may be uncoated or coated by known techniques to delay disintegration and absorption in the gastrointestinal tract and thereby provide a sustained action over a longer period. For example, a time delay material such as glyceryl monostearate or glyceryl distearate may be employed. Coating may also be performed using techniques described in the U.S. Pat. Nos. 4,256,108; 4,160,452; and 4,265,874 to form osmotic therapeutic tablets for control release.

The above compounds as well as the pharmaceutically-active agent useful in the method of the invention can be administered, for in vivo application, parenterally by injection or by gradual perfusion over time independently or together. Administration may be intraocular, intravenously, intraarterial, intraperitoneally, intramuscularly, subcutaneously, intracavity, transdermally or infusion by, for example, osmotic pump. For in vitro studies the agents may be added or dissolved in an appropriate biologically acceptable buffer and added to a cell or tissue.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's intravenous vehicles include fluid and nutrient replenishers, electrolyte replenishers (such as those based on Ringer's dextrose), and the like. Preservatives and other additives may also be present such as, for example, anti-microbials, anti-oxidants, chelating agents, growth factors and inert gases and the like.

The present invention includes various pharmaceutical compositions useful for ameliorating disease. The pharmaceutical compositions according to one embodiment of the invention are prepared by bringing an above compound, analogs, derivatives or salts thereof, or combinations of the above compounds and one or more pharmaceutically-active agents into a form suitable for administration to a subject using carriers, excipients and additives or auxiliaries. Frequently used carriers or auxiliaries include magnesium carbonate, titanium dioxide, lactose, mannitol and other sugars, talc, milk protein, gelatin, starch, vitamins, cellulose and its derivatives, animal and vegetable oils, polyethylene glycols and solvents, such as sterile water, alcohols, glycerol and polyhydric alcohols. Intravenous vehicles include fluid and nutrient replenishers. Preservatives include antimicrobial, anti-oxidants, chelating agents and inert gases. Other pharmaceutically acceptable carriers include aqueous solutions, non-toxic excipients, including salts, preservatives, buffers and the like, as described, for instance, in Remington's Pharmaceutical Sciences, 20th ed, Williams and Wilkins (2000) and The British National Formulary 43rd ed. (British Medical Association and Royal Pharmaceutical Society of Great Britain, 2002; http://bnf.rhn.net), the contents of which are hereby incorporated by reference. The pH and exact concentration of the various components of the pharmaceutical composition are adjusted according to routine skills in the art. See Goodman and Gilman's The Pharmacological Basis for Therapeutics (7th ed., 1985).

The pharmaceutical compositions are preferably prepared and administered in dose units. Solid dose units may be tablets, capsules and suppositories. For treatment of a subject, depending on activity of the compound, manner of administration, nature and severity of the disorder, age and body weight of the subject, different daily doses can be used. Under certain circumstances, however, higher or lower daily, doses may be appropriate. The administration of the daily dose can be carried out both by single administration in the form of an individual dose unit or else several smaller dose units and also by multiple administration of subdivided doses at specific intervals.

The pharmaceutical compositions according to the invention may be administered locally or systemically in a therapeutically effective dose. Amounts effective for this use will, of course, depend on the severity of the disease and the weight and general state of the subject. Typically, dosages used in vitro may provide useful guidance in the amounts useful for in situ administration of the pharmaceutical composition, and animal models may be used to determine effective dosages for treatment of the cytotoxic side effects. Various considerations are described, e.g., in Langer, Science, 249:1527, (1990). Formulations for oral use may be in the form of hard gelatin capsules wherein the active ingredient is mixed with an inert solid diluent, for example, calcium carbonate, calcium phosphate or kaolin. They may also be in the form of soft gelatin capsules wherein the active ingredient is mixed with water or an oil medium, such as peanut oil, liquid paraffin or olive oil.

Aqueous suspensions normally contain the active materials in admixture with excipients suitable for the manufacture of aqueous suspension. Such excipients may be (1) suspending agent such as sodium carboxymethyl cellulose, methyl cellulose, hydroxypropylmethylcellulose, sodium alginate, polyvinylpyrrolidone, gum tragacanth and gum acacia; (2) dispersing or wetting agents which may be (a) naturally occurring phosphatide such as lecithin; (b) a condensation product of an alkylene oxide with a fatty acid, for example, polyoxyethylene stearate; (c) a condensation product of ethylene oxide With a long chain aliphatic alcohol, for example, heptadecaethylenoxycetanol; (d) a condensation product of ethylene oxide with a partial ester derived from a fatty acid and hexitol such as polyoxyethylene sorbitol monooleate, or (e) a condensation product of ethylene oxide with a partial ester derived from fatty acids and hexitol anhydrides, for example polyoxyethylene sorbitan monooleate.

The pharmaceutical compositions may be in the form of a sterile injectable aqueous or oleagenous suspension. This suspension may be formulated according to known methods using those suitable dispersing or wetting agents and suspending agents which have been mentioned above. The sterile injectable preparation may also a sterile injectable solution or suspension in a non-toxic parenterally-acceptable diluent or solvent, for example, as a solution in 1,3-butanediol. Among the acceptable vehicles and solvents that may be employed are water, Ringer's solution, and isotonic sodium chloride solution. In addition, sterile, fixed oils are conventionally employed as a solvent or suspending medium. For this purpose, any bland fixed oil may be employed including synthetic mono- or diglycerides. In addition, fatty acids such as oleic acid find use in the preparation of injectables.

The above compounds may also be administered in the form of liposome delivery systems, such as small unilamellar vesicles, large unilamellar vesicles, and multilamellar vesicles. Liposomes can be formed from a variety of phospholipids, such as cholesterol, stearylamine, or phosphatidylcholines.

The above compounds may also be presented for use in the form of veterinary compositions, which may be prepared, for example, by methods that are conventional in the art. Examples of such veterinary compositions include those adapted for:
(a) oral administration, external application, for example drenches (e.g. aqueous or non-aqueous solutions or suspensions); tablets or boluses; powders, granules or pellets for admixture with feed stuffs; pastes for application to the tongue;
(b) parenteral administration for example by subcutaneous, intramuscular or intravenous injection, e.g. as a sterile solution or suspension; or (when appropriate) by intramammary injection where a suspension or solution is introduced in the udder via the teat;
(c) topical applications, e.g. as a cream, ointment or spray applied to the skin; or
(d) intravaginally, e.g. as a pessary, cream or foam.

The present invention is further described by the following non-limiting Examples.

Example 1

PB Compound Mediated Dissolution of Aggregated Abeta 1-42

Abeta1-42, is available from the Keck Laboratory, Yale University School of Medicine. PBS (pH 6.6): Sigma Cat# D-8662. Zn(ZnCl2): BDH Cat#100884E. (Dissolved in water in 1 mM concentration) DMSO: Ajax Cat#2225. Thioflavin T: Sigma Cat# T-3516. (Dissolved in water in 1 mM concentration)

By way of example of an amyloid composition, Abeta is dissolved in distilled water and peptide concentration is assessed by measured absorption at 214 nm in UV spectrometer. An aggregation reactive mixture (per one concentration of one testing compound) is set us as follows: Abeta: 25 µM, $ZnCl_2$ 50 µM, ThT 50 µM, PBS to make up to 500 µl. The tube is wrapped with foil and incubated at 37 degrees by rotation for 24 hours. A serial dilution of each test compound is made up in DMSO, for example: 100 µM, 500 µM, 1000 µM, 2500 µM and 5000 µM. The final concentrations are 1, 5, 10, 25 and 50 µM, 5 µl of each of these compounds is placed in a centrifuge tube and 5 µl of DMSO is added to both negative and positive control tubes. 495 µl of aggregates (after 24 hours incubation) is added to the centrifuge tube. The negative control is PBS plus $ZnCl_2$ and ThT and DMSO. The positive control is aggregates plus DMSO. The tubes are incubated at 37 degrees for further 2 hours with rotation. Samples are measured for ThT fluorescence using an LS55 (Perkin Elmer) fluorimeter in a cuvette (500 µl volume). The excitation wavelength is 450 nm and the emission wavelength is 480 nm. Data are analyzed using graph pad prism program. The tested compounds included so called "PB" compounds.

Example 2

Post Mortem Screening

The BAS assay is adopted for post mortem retina. Using a trephine, 6 mm diameter regions of peripheral retina from frozen donor eyes are dissected. Following defrosting, the neuronal retina and the RPE cells are removed by gentle agitation in PBS buffer. Following removal of the RPE cells, strips of the Bruch membrane are cut from the eye.
4 samples are prepared:
1) Control
2) 100 µM TPEN
3) 100 µM PB-1033
4) 250 µM PB-1033

Following a 30 mins incubation samples are washed 3 times with PBS and then 10 µM ZP1 (fluorescence sensor for zinc) application for 10 min.

Samples are then washed 3 times and the labeling visualized using a fluorescence and confocal microscope.

A repeat of this procedure is performed with the exception that samples are incubated for a period of 15 hours before washing to determine differential metal binding over this longer period.

The test results are in the form of fluorescence imaging from a confocal microscope of the 4 samples tested in this Example after 15 hours of sample incubation. The results showed that TPEN inhibited ZP1 labeling indicating the effectiveness of the assay. PB-1033 also inhibited ZP1 labeling. The results clearly show that PB-1033 inhibits and reduces metal ions in retinal drusen. Fluorescence microscopic photographs (which are in colour) are available upon request from the Patentee.

Example 3

Clinical Trial

AMD patients are selected and given a test compound (including a PB compound) at a concentration of 500 mg/day for one month. Readouts are taken at baseline and then at 1 month and include:
1. microperimetry; and
2. multifocal retinography.

If the retinae are relieved of oxidative stress after MPAC treatment, it should be reflected by stabilization of these markers of retinal health.

Example 4

Assessment of Compounds

The following Assays were used in the assessment of the compounds for suitability for use in the methods of the invention.

Assay 1. Fluorometric $H_2O_2$ Assay

A fluorometric assay was used to test the ability of a test compound to inhibit hydrogen peroxide generation by $A\beta$ in the presence of copper based on dichlorofluoroscein diacetate (DCF; Molecular Probes, Eugene Oreg.). The DCF solution (5 mM) in 100% dimethyl sulphoxide (previously purged with argon for 2 hr at 20° C.) was deacetylated in the presence of 0.25M NaOH for 30 min and neutralized at pH 7.4 to a final concentration of 1 mM. Horseradish peroxidase (HRP) stock solution was prepared to 1 µM at pH 7.4. The reactions were carried out in PBS, pH 7.4 in a 96 well plate (total volume=250 µl/well). The reaction solutions contained $A\beta$ 1-42 at concentrations in the range of 50 nM to 1 µM, copperglycine chelate (Cu-Gly), was prepared by adding $CuCl_2$ to glycine in the ratio of 1:6 and added to the $A\beta$ in the proportion 2Cu-Gly:1A$\beta$), reducing agents including dopamine (5 µM) or ascorbic acid, deacetylated DCF 100 µM, and HRP, 0.1 µM. 1-10 µM EDTA or another chelator may also be present as a control for free copper, but was not required for the assay to function. The reaction mixture was incubated at 37 C for 60 min. Catalase (4000 units/ml) and $H_2O_2$ (1-2.5 µM) standards in PBS pH 7.4 may be included as positive controls. Fluorescence was recorded using a plate reader with excitation and emission filters at 485 nM and 530 nM respectively. $H_2O_2$ concentration may be established by comparing fluorescence with the $H_2O_2$ standards, Inhibition of $A\beta$ $H_2O_2$ production was assayed by including a given concentration of test compound(s) in the test wells.

Assay 2. Neurotoxicity Assays

Primary Cortical Neuronal Cultures

Cortical cultures were prepared as previously described (White et al., *J Neuroscience* 18:6207-6217, 1998). Embryonic day 14 BL6Jx129sv mouse cortices were removed, dissected free of meninges and dissociated in 0.025% (wt/vol) trypsin. Dissociated cells were plated in 48 well culture plates at a density of $2 \times 10^6$ cells/mL in MEM with 25% (vol/vol) FCS and 5% (vol/vol) HS and incubated at 37° C., 2 hrs. Media was then replaced with Neurobasal media (Invitrogen Life Technologies) and B27 supplements (Invitrogen Life Technologies). Cultures were maintained at 37° C. in 5% $CO_2$. Prior to experimentation, the culture medium was replaced with Neurobasal media and B27 minus antioxidants (Invitrogen Life Technologies).

Assay 3. MTS Assay for Cell Viability

Cell viability is determined using the MTS assay. Culture medium is replaced with fresh neurobasal medium plus B27 supplements minus antioxidants. 1/10th volume MTS solution (Cell Titre 96 Aqueous One, Promega Corporation) and incubated at 37° C., 2 hrs. 200 microliter aliquots are measured with a spectrophotometer at 560 nm.

Assay 4. Assay for Test Compound Cytoxicity

Neuronal cortical cells were cultured for five days as per Assay 2 in NB media and B27 supplement.

On day six the test compounds were added to the neuronal cell cultures in NB media and B27 supplement minus antioxidants.

Test compounds were dissolved in 100% DMSO to a concentration of 2.5 mM (10 mM if excess compound was weighed out per vial—then diluted to 2.5 mM). 2.5 mM stock solution was serially diluted 1 in 10 to give working solutions of 250 µM, 25 µM, 2.5 µM.

Test compounds were not added directly to cells, instead they were added to a 48 well 'Drug Plate' as comprised below:

Preparation of "Drug Plate":

To a 48 well plate add:

Well 1: 576 µl NB+B27 (no antioxidant)*+24 µl 2.5 M test compound

Well 2: 576 µl NB+B27 (no antioxidant)+24 µl 25 µM test compound

Well 3: 576 µl NB+B27 (no antioxidant)+24 µl 250 µM test compound

Well 4: 576 µl NB+B27 (no antioxidant)+24 µl 2.5 µM test compound

Well 5: 576 µl NB+B27 (no antioxidant)+24 µl 250 µM test compound

Well 6: 576 µl NB+B27 (no antioxidant)+24 µl 250 µM test compound

Well 7: 576 µl NB+B27 (no antioxidant)+24 µl test compound diluent**

Well 8: 600 µl NB+B27 (no antioxidant)

* NB media and B27 (no antioxidants),

** PBT diluent 10% DMSO in NB+B27 (no antioxidants)

The Drug Plate was incubated at 37° C. for 15 mins. 200 µl of each well was added in triplicate to the corresponding cell plate. The cell plate was incubated at 37 C, for 4 days.

On completion of the assay, 1/10 volume MTS was added per well of plate (ie 25 µl/250 µl). The plates were incubated at 37 C for 2 hrs, and then absorbance was read at 560 nm.

Assay 5. Human Brain Amyloid Solubilization Assay

This assay was performed in order to assess the ability of a test compound to mobilise $A\beta$, as an example form of amyloid, from the insoluble to the soluble phase of an extract of tissue from post mortem human AD brain.

Up to 0.5 g of plaque-bearing cortex without meninges was homogenized using a DIAX 900 homogenizer (Hendolph and Co, Kelheim, Germany) or other suitable device for three 30-second periods at full speed in 2 ml of ice-cold phosphate-buffered saline, pH 7.4. To obtain the phosphate-buffered saline-extractable fraction, the homogenate was centrifuged at 100,000×g for 30 min and the supernatant removed. Alternatively, the tissue was freeze dried then pulverized to form a powder which was then weighed out into aliquots for extraction as above. Supernatant, either freeze-dried and resuspended or in unconcentrated form, was dissolved in 200 µl of Tris-Tricine sodium dodecyl sulfate (SDS) sample buffer pH 8.3 containing 8% SDS, 10% 2-mercaptoethanol. Aliquots (10 µl) were then boiled for 10 minutes before SDS-polyacrylamide gel electrophoresis. The insoluble fraction of the cortical samples was obtained by resuspending the initial pelleted sample in 1 ml of phosphate-buffered saline, A 50-µl aliquot of this suspension was then boiled in 200 ml of sample buffer as above.

Tris-Tricine polyacrylamide gel electrophoresis was performed by loading appropriately diluted samples on to 10% to 20% gradient gels (Novex, San Diego, Calif.) followed by transfer on to 0.2-µm nitrocellulose membrane (Bio-Rad, Hercules, Calif.). $A\beta$ was detected by using monoclonal antibody W02, which detects residues 5 through 8, 17 (or another suitable antibody) in conjunction with horseradish peroxidase-conjugated rabbit anti-mouse IgG (Dako, Denmark), and visualized by using enhanced chemiluminescence (eg ECL; Amersham Life Science, Buckinghamshire, UK). Each gel included three lanes containing 0.5, 1, and 2 ng of synthetic $A\beta_{40}$ (Keck Laboratory, Yale University, New Haven, Conn.) as reference standards.

Blot films were scanned by using a suitable imaging system such as the UVP gel documentation system, and densitometry performed using suitable software, eg UVP Labworks. The dynamic range of the film/scanner was determined by using a step tablet (No. 911ST600, Kodak, Rochester N.Y.), a calibrated film exposed by the manufacturer to provided steps of known increasing intensity. The quantifiable range of signal intensity for densitometric analysis of the mono- and dimeric $A\beta$ bands was based on the comparison with a curve obtained by scanning and densitometry of the step tablet. Samples in which the signal intensity is low after preliminary assay may be re-assayed by using synthetic standards of lower or higher concentration.

All samples were analyzed at least twice, and gel loadings and dilutions were adjusted to fit within the quantifiable region of the standard curve. The proportion of 'soluble' to 'insoluble' Aβ may be used to determine the efficiency of extraction of a test compound compared with the efficiency of a known compound. The insoluble Aβ being comprised of the pelletable fraction derived from the insoluble amyloid plaque from the above cortical samples and the soluble fraction comprising monomeric and/or oligomeric soluble Aβ.

Assay 6. Effect of Administration of Test Compounds on Aβ Deposits in Transgenic Animals Transgenic mouse models are available for a number of neurological disorders, including Alzheimer's disease; Parkinson's disease; familial amyotrophic lateral sclerosis (ALS); Huntington's disease; and Creutzfeld-Jakob disease (CJD). It was found that one of the transgenic models for Alzheimer's disease, the APP2576 transgenic mouse also has a high incidence of cataract. These animal models were suitable for testing the methods of the invention.

Transgenic mice of the strain APP2576 were used. Eight to nine month old female mice were selected and divided into groups for treatment.

Mice were sacrificed at intervals, and their brains examined to determine whether the treatment with test compounds decreased brain amyloid formation, and the identification of the most effective administration protocol.

Other mice in each group were tested over a period of up to eight months for cognitive performance, using a Morris water maze according to standard methods. The general health and well-being of the animals was also measured every day by a blinded operator, using a five point integer scale which subjectively rates a combination of features, including motor activity, alertness and general health signs.

Assay 7. Solubility Assay

Stock solutions of compounds of formula I or II (1 mM) were prepared in dimethyl sulfoxide. Compounds which did not dissolve were classed as not soluble (N). The DMSO stock solutions were diluted 1 in 100 into PBS pH 7.4. Compounds which gave a clear solution were classed as soluble (Y), while those compounds which gave a translucent suspension after dissolution in DMSO were classed as "crashed out" (C).

Assay 8. Physiochemical Properties

Polar Surface Area Calculations (PSA)

Polar surface area values were calculated using the web-based program available through "Molinspiration", a package for calculation of molecular properties.

Turbidimetric Solubility Measurements

The solubility estimate was measured at both pH 2.0 and pH 6.5. This is within the pH range that can be anticipated along the proximal gastrointestinal tract in humans.

The compounds were dissolved in DMSO to appropriate concentrations and then spiked into either 0.01M HCl (approx, pH=2.0) or pH 6.5 isotonic phosphate buffer, the final DMSO concentration being 1%. Samples were then analyzed via Nephelometry to determine a solubility range (Bevan and Lloyd, *Anal. Chem.* 72:1781-1787, 2000).

cLog P Values

Theoretical Log P values were determined using the ACD Log P software. The values quoted have been calculated from an untrained database and refer to the unionized species.

E Log D

Effective Log D values were measured using a chromatographic method employing a SUPELCOSIL LC-ABZ column using an octanol saturated mobile phase at pH 7.4.

See F. Lombardo et al, *J. Med. Chem.* 2000, 43, 2922-2928.

Example 5

Properties of PBT Compounds

Table 8 provides the properties and structures of particularly preferred PBT compounds which fall within the scope of the present invention.

Results on AMD Compounds

| | In vitro Efficacy Profile | | | Physico-chemical properties | | In vivo Efficacy and Safety Profile | | | |
|---|---|---|---|---|---|---|---|---|---|
| | $H_2O_2$ $IC_{50}$ $(\mu M)^a$ | Cytotox (% viable at 1 and 10 $\mu M)^b$ | CuTy[c] BAS[d] | Disaggre- gation[e] | Parent MW/ PSA | ClogP ElogD (E) or ClogD (C) | Toxicity[f] at 30 mg/kg | Mice plasma concen- tration[g] | Tg Mice[h] |
| PB 31 | | | | 4.9, 50.5 | 887.69 | | | | |

-continued

| | In vitro Efficacy Profile | | | Physico-chemical properties | | In vivo Efficacy and Safety Profile | | |
|---|---|---|---|---|---|---|---|---|
| | $H_2O_2$ $IC_{50}$ ($\mu M$)[a] | Cytotox (% viable at 1 and 10 $\mu M$)[b] | CuTy[c] BAS[d] | Disaggregation[e] | Parent MW/ PSA | ClogP ElogD (E) or ClogD (C) | Toxicity[f] at 30 mg/kg | Mice plasma concentration[g] | Tg Mice[h] |

| PB 32 | >5.0 | | | 5, 50 | 883.69 | | | | |
| PB 42 | 0.70 | Neuronal cells: 93, 36 | BAS: 227% (1 μM- 100 μM) | Inactive | 145.16 | 2.08 | | | |
| PB 44 | >10 | Neuronal cells: 108, 71 | BAS: 191% (1 μM- 10 μM) | | 233.10 | 1.53 | | | |

| | | In vitro Efficacy Profile | | | | Physico-chemical properties | | In vivo Efficacy and Safety Profile | | |
|---|---|---|---|---|---|---|---|---|---|---|
| | | H$_2$O$_2$ IC$_{50}$ (µM)$^a$ | Cytotox (% viable at 1 and 10 µM)$^b$ | CuTy$^c$ BAS$^d$ | Disaggregation$^e$ | Parent MW/ PSA | ClogP ElogD (E) or ClogD (C) | Toxicity$^f$ at 30 mg/kg | Mice plasma concentration$^g$ | Tg Mice$^h$ |
| PB 45 | [5,7-dichloro-8-hydroxyquinoline] | 0.40 | Neuronal cells: 98, 75 | BAS: 387% (1 pM-10 nM) | 8.5, 36.1 | 214.05 | 3.34 | | | |
| PB 46 | [5,7-diiodo-8-hydroxyquinoline] | 0.40 | Neuronal cells: 91, 95 | | 4.1, 58.7 | 396.96 | 4.14 | | | |
| PB 47 | [5,7-dibromo-8-hydroxyquinoline] | 0.50 | Neuronal cells: 100, 94 | BAS: 412% (1 µM-100 µ) | 5, 50 | 302.95 | 3.69 | | | |

-continued

| | In vitro Efficacy Profile | | | | Physico-chemical properties | | In vivo Efficacy and Safety Profile | | | |
|---|---|---|---|---|---|---|---|---|---|---|
| | $H_2O_2$ $IC_{50}$ (μM)[a] | Cytotox (% viable at 1 and 10 μM)[b] | CuTy[c] BAS[d] | Disaggre- gation[e] | Parent MW/ PSA | ClogP ElogD (E) or ClogD (C) | Toxicity[f] at 30 mg/kg | Mice plasma concen- tration[g] | Tg Mice[h] |
| PB 56 | 0.25 | Neuronal cells: 80, 25 | BAS: 311% (1 μM- 100 μM) | | 317.35 | 4.69 | | | |
| PB 59 | 0.70 | Neuronal cells: 86, 85 | BAS: 293% (1 nM- 10 μM) | | 173.22 | 3.03 | | | |

-continued

| | In vitro Efficacy Profile | | | Physico-chemical properties | | In vivo Efficacy and Safety Profile | | |
|---|---|---|---|---|---|---|---|---|
| | H₂O₂ IC₅₀ (μM)[a] | Cytotox (% viable at 1 and 10 μM)[b] | CuTy[c] BAS[d] | Disaggre-gation[e] | Parent MW/ PSA | ClogP ElogD (E) or ClogD (C) | Toxicity[f] at 30 mg/kg | Mice plasma concen-tration[g] | Tg Mice[h] |
| PB 68 | >10 | | | 8.5, 44 | 756.51 | | | | |
| PB 72 | 10 | | | >20, 24 | 784.57 | | | | |
| PB 89 | 2.5 | Neuronal cells: 100, 75 | BAS: 233% (1 μM-10 μM) | | 263.30 | 3.70 | | | |

-continued
| | In vitro Efficacy Profile | | | | Physico-chemical properties | | In vivo Efficacy and Safety Profile | | |
|---|---|---|---|---|---|---|---|---|---|
| | $H_2O_2$ $IC_{50}$ (μM)[a] | Cytotox (% viable at 1 and 10 μM)[b] | CuTy[c] BAS[d] | Disaggregation[e] | Parent MW/ PSA | ClogP ElogD (E) or ClogD (C) | Toxicity[f] at 30 mg/kg | Mice plasma concentration[g] | Tg Mice[h] |
| PB 116 | 0.5 | Neuronal cells: 81, 60 | BAS: 220% (10 nM-10 μM) | | 328.39 | 3.75 | | | |
| PB 233 | >10 | | BAS: 330% (1 nM-10 μM) | | 281.24 | 5.53 | | | |
| PB 470 | >10 | | BAS: 193% (0.1 μM-5 μM) | | 357.80 | 4.18 | | | |
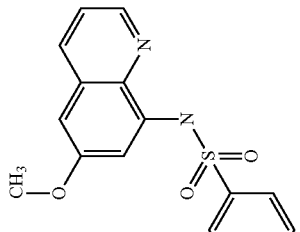
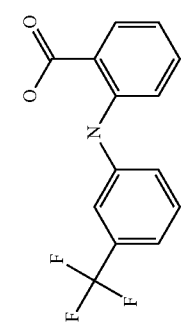
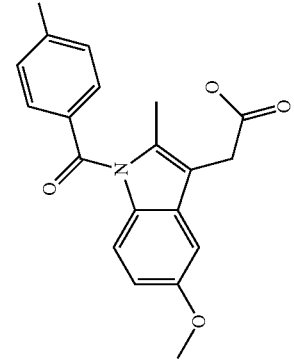

| | In vitro Efficacy Profile | | | | Physico-chemical properties | | In vivo Efficacy and Safety Profile | | |
|---|---|---|---|---|---|---|---|---|---|
| | $H_2O_2$ $IC_{50}$ $(\mu M)^a$ | Cytotox (% viable at 1 and 10 $\mu M)^b$ | CuTy[c] BAS[d] | Disaggre- gation[e] | Parent MW/ PSA | ClogP ElogD (E) or ClogD (C) | Toxicity[f] at 30 mg/kg | Mice plasma concen- tration[g] | Tg Mice[h] |
| PB 806 | <0.9 | Neuronal cells: 100, 97 | BAS: 311% (1 nM- 100 μM) | | 300.16 | 4.67 | | | |
| PB 809 | <1.8 | Neuronal cells: 97, 26 | BAS: 146% (1 μM- 100 μM) | | 297.36 | 5.35 | | | |
| PB 810 | <0.7 | Neuronal cells: 83, 71 | BAS: 184% (1- 10 pM, 1 nM) | | 285.73 | 4.23 | | | |
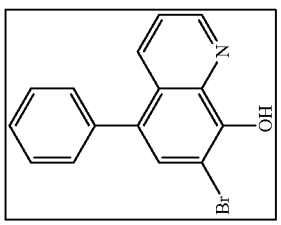
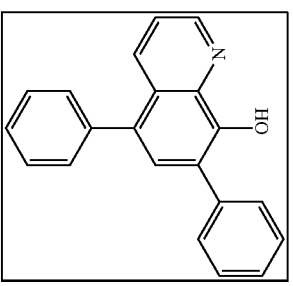
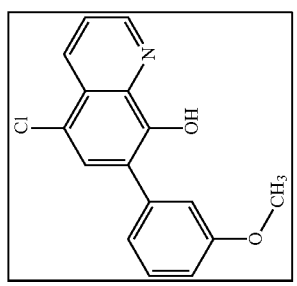

| | | In vitro Efficacy Profile | | | Physico-chemical properties | | In vivo Efficacy and Safety Profile | | |
|---|---|---|---|---|---|---|---|---|---|
| | | Cytotox (% viable at 1 and 10 µM)[b] | CuTy[c] / BAS[d] | Disaggre- gation[e] | Parent MW/ PSA | ClogP ElogD (E) or ClogD (C) | Toxicity[f] at 30 mg/kg | Mice plasma concen- tration[g] | Tg Mice[h] |
| | H₂O₂ IC₅₀ (µM)[a] | | | | | | | | |
| PB 814 | 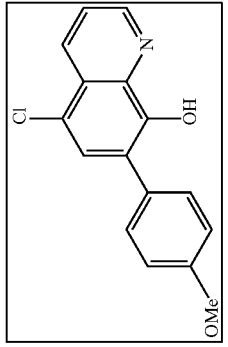 | <1.1 | Neuronal cells: 97, 31 | BAS: 209% (1 nM- 100 µM) | | 285.73 | 4.23 | | | |
| PB 847 | 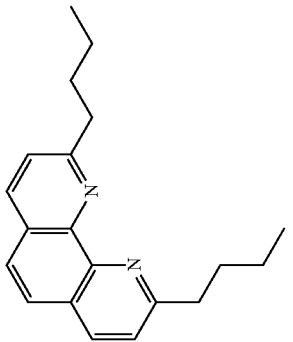 | <2.5 | | BAS: 271% (1 µM- 100 µM) | | 292.43 | 6.22 | | | |
| PB 851 | 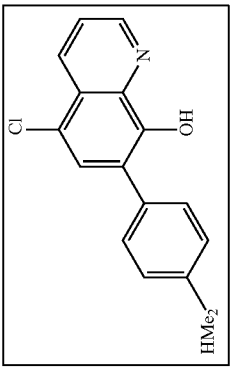 | <0.7 | Neuronal cells: 94, 85 | BAS: 362% (100 µM) | | 298.77 | 4.50 | | | |

| | In vitro Efficacy Profile | | | | Physico-chemical properties | | In vivo Efficacy and Safety Profile | | |
|---|---|---|---|---|---|---|---|---|---|
| | $H_2O_2$ $IC_{50}$ $(\mu M)^a$ | Cytotox (% viable at 1 and 10 μM)[b] | CuTy[c] BAS[d] | Disaggre-gation[e] | Parent MW/ PSA | ClogP ElogD (E) or ClogD (C) | Toxicity[f] at 30 mg/kg | Mice plasma concen-tration[g] | Tg Mice[h] |
| PB 852 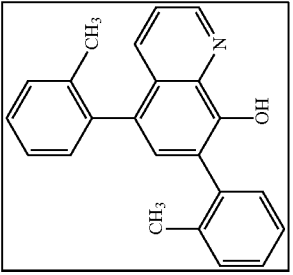 | 2.1 | Neuronal cells: 93, 34 | BAS: 220% (1 μM- 100 μM) | | 325.41 | 5.75 | | | |
| PB 853 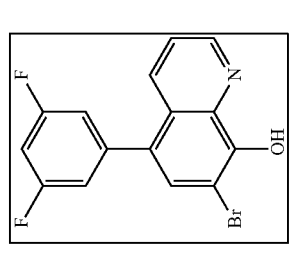 | 0.77 | Neuronal cells: 95, 95 | BAS: 221% (1 nM, 100 nM- 10 μM) | | 336.14 | 4.97 | | | |
| PB 854 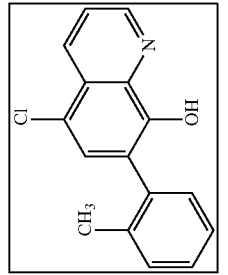 | 0.78 | Neuronal cells: 100, 100 | BAS: 520% (1 nM- 100 μM) | | 269.73 | 4.50 | | | |

| | In vitro Efficacy Profile | | | | Physico-chemical properties | | In vivo Efficacy and Safety Profile | | |
|---|---|---|---|---|---|---|---|---|---|
| | H$_2$O$_2$ IC$_{50}$ (μM)[a] | Cytotox (% viable at 1 and 10 μM)[b] | CuTy[c] BAS[d] | Disaggre- gation[e] | Parent MW/ PSA | ClogP ElogD (E) or ClogD (C) | Toxicity[f] at 30 mg/kg | Mice plasma concen- tration[g] | Tg Mice[h] |
| PB 859 | <0.67 | Neuronal cells: 98, 73 | BAS: 266% (1 nM- 10 μM) | | 269.73 | 4.80 | | | |
| PB 860 | 0.79 | Neuronal cells: 91, 90 | BAS: 160% (1 μM- 100 μM) | | 415.16 | 5.76 | | | |
| PB 861 | <0.91 | Neuronal cells: 99, 38 | BAS: 439% (1 μM- 100 μM) | 20, 31.4 | 361.18 | 5.06 | | | |
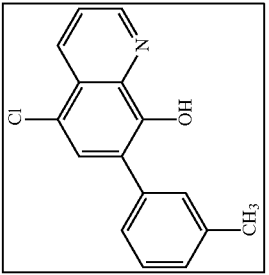
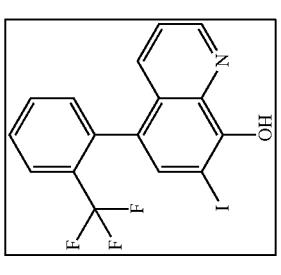
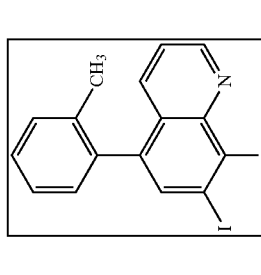

| | In vitro Efficacy Profile | | | | Physico-chemical properties | | In vivo Efficacy and Safety Profile | | |
|---|---|---|---|---|---|---|---|---|---|
| | $H_2O_2$ $IC_{50}$ $(\mu M)^a$ | Cytotox (% viable at 1 and 10 $\mu M)^b$ | CuTy$^c$ / BAS$^d$ | Disaggre- gation$^e$ | Parent MW/ PSA | ClogP ElogD (E) or ClogD (C) | Toxicity$^f$ at 30 mg/kg | Mice plasma concen- tration$^g$ | Tg Mice$^h$ |
| PB 862 | <0.77 | Neuronal cells: 100, 52 | BAS: 256% (1 µM- 100 µM) | | 357.41 | 4.09 | | | |
| PB 863 | <0.73 | Neuronal cells: 91, 35 | BAS: 386% (1 µM- 100 µM) | | 377.18 | 4.23 | | | |
| PB 864 | 0.77 | Neuronal cells: 96, 93 | BAS: 208% (10 µM- 100 µM) | | 323.70 | 5.20 | | | |

-continued

| | | In vitro Efficacy Profile | | | | Physico-chemical properties | | In vivo Efficacy and Safety Profile | | |
|---|---|---|---|---|---|---|---|---|---|---|
| | | H$_2$O$_2$ IC$_{50}$ (μM)$^a$ | Cytotox (% viable at 1 and 10 μM)$^b$ | CuTy$^c$ BAS$^d$ | Disaggregation$^e$ | Parent MW/ PSA | ClogP ElogD (E) or ClogD (C) | Toxicity$^f$ at 30 mg/kg | Mice plasma concentration$^g$ | Tg Mice$^h$ |
| PB 896 | 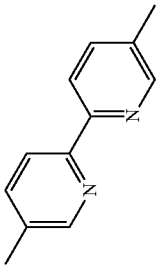 | 0.15 | Neuronal cells: 86% (at 10 uM) | BAS: 358% (1 pM-10 nM) | | 184.24 | 2.56 | | | |
| PB 898 | 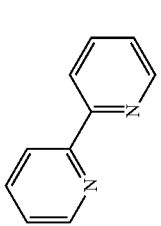 | 0.23 | | | >20, 32 | 156.2 | 1.56 | | | |
| PB 913 | 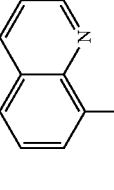 | 0.99 | Neuronal cells: 100, 95 | BAS: 450% (1 μM-100 μM) | | 243.25 | 4.01 | | | |
| PB 915 | 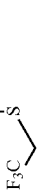 | 1.9 | | BAS: 202% (1 μM-100 μM) | | 307.38 | 3.18 | | | |

-continued

| | In vitro Efficacy Profile | | | | Physico-chemical properties | | In vivo Efficacy and Safety Profile | | |
|---|---|---|---|---|---|---|---|---|---|
| | $H_2O_2$ $IC_{50}$ (μM)[a] | Cytotox (% viable at 1 and 10 μM)[b] | CuTy[c] BAS[d] | Disaggregation[e] | Parent MW/ PSA | ClogP ElogD (E) or ClogD (C) | Toxicity[f] at 30 mg/kg | Mice plasma concentration[g] | Tg Mice[h] |
| PB 933 | 0.11 | Neuronal cells: 127% (at 10 μM) | BAS: 279% (1-100 nM, 100 μM) | | 256.44 | −0.58 | | | |
| PB 934 | 0.11 | Neuronal cells: 114% (at 10 μM) | BAS: 293% (1 nM-10 μM) | | 200.33 | −1.85 | | | |
| PB 942 | <0.1 | | BAS: 220% (1 nM-10 μ) | | 308.08 | −0.36 | | | |
| PB 947 | 1.14 | Neuronal cells: 100, 70 | BAS: 244% (1 pM-10 nM) | | 271.71 | 3.14 | | | |

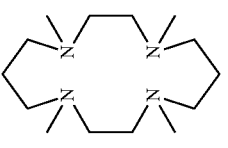

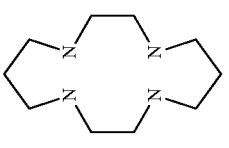

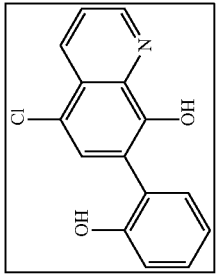

| | In vitro Efficacy Profile | | | | Physico-chemical properties | | In vivo Efficacy and Safety Profile | | |
|---|---|---|---|---|---|---|---|---|---|
| | H$_2$O$_2$ IC$_{50}$ (μM)$^a$ | Cytotox (% viable at 1 and 10 μM)$^b$ | CuTy$^c$ BAS$^d$ | Disaggregation$^e$ | Parent MW/ PSA | ClogP ElogD (E) or ClogD (C) | Toxicity$^f$ at 30 mg/kg | Mice plasma concentration$^g$ | Tg Mice$^h$ |
| PB 948 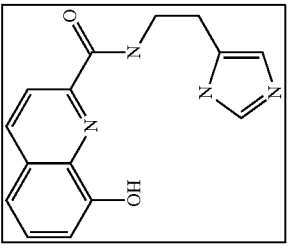 | 0.15 | 100, 100 | BAS: 576% (1 μM-10 μM) | | 282.30 | 1.61 | | | |
| PB 949 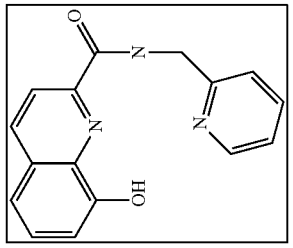 | 0.43 | Neuronal cells: 96, 85 | BAS: 201% (1 μM-100 μM) | | 279.30 | 2.38 | | | |
| PB 950 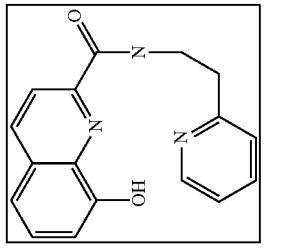 | 0.15 | Neuronal cells: 95, 93 | BAS: 741% (1 μM-100 μM) | | 293.33 | 2.51 | | | |

-continued

| | In vitro Efficacy Profile | | | | Physico-chemical properties | | In vivo Efficacy and Safety Profile | | |
|---|---|---|---|---|---|---|---|---|---|
| | $H_2O_2$ $IC_{50}$ (μM)[a] | Cytotox (% viable at 1 and 10 μM)[b] | CuTy[c] BAS[d] | Disaggre- gation[e] | Parent MW/ PSA | ClogP ElogD (E) or ClogD (C) | Toxicity[f] at 30 mg/kg | Mice plasma concen- tration[g] | Tg Mice[h] |
| PB 952 | 0.27 | Neuronal cells: 100, 100 | BAS: 268% (1 nM- 100 μM) | | 271.30 | 2.47 | | | |
| PB 953 | <0.42 | Neuronal cells: 94, 68 | BAS: 325% (1 μM- 100 μM) | | 285.33 | 2.93 | | | |
| PB 954 | 0.12 | Neuronal cells: 100, 100 | BAS: 134% (1 μM) | | 298.30 | 1.70 | | | |

-continued

| | | In vitro Efficacy Profile | | | Physico-chemical properties | | In vivo Efficacy and Safety Profile | | |
|---|---|---|---|---|---|---|---|---|---|
| | $H_2O_2$ $IC_{50}$ (μM)[a] | Cytotox (% viable at 1 and 10 μM)[b] | CuTy[c] BAS[d] | Disaggre-gation[e] | Parent MW/ PSA | ClogP ElogD (E) or ClogD (C) | Toxicity[f] at 30 mg/kg | Mice plasma concen-tration[g] | Tg Mice[h] |
| PB 957 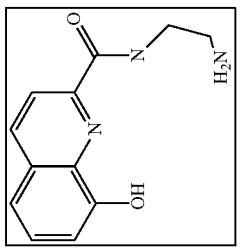 | >10 | Neuronal cells: 106, 96 | BAS: 190% (1 μM, 100 μM) | | 231.26 | 1.43 | | | |
| PB 968 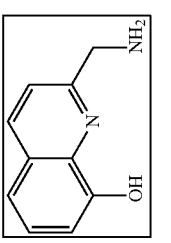 | 0.26 | Neuronal cells: 101, 97 | BAS: 390% (1 nM-100 μM) | 16.3, 31.6 | 174.20 | 1.03 | | | |
| PB 969 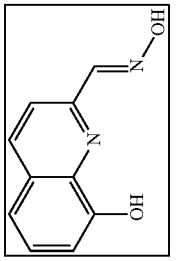 | 0.54 | Neuronal cells: 100, 95 | BAS: 385% (1 μM-10 μM) | | 188.19 | 2.83 | | | |
| PB 977 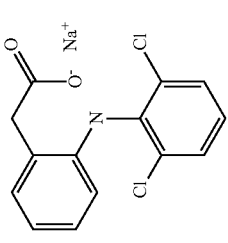 | | | BAS: 385% (1-10 nM, 1-10 μM) | | 318.14 | 4.73 | | | |

| | In vitro Efficacy Profile | | | | Physico-chemical properties | | In vivo Efficacy and Safety Profile | | |
|---|---|---|---|---|---|---|---|---|---|
| | $H_2O_2$ $IC_{50}$ $(\mu M)^a$ | Cytotox (% viable at 1 and 10 μM)[b] | CuTy[c] BAS[d] | Disaggre- gation[e] | Parent MW/ PSA | ClogP ElogD (E) or ClogD (C) | Toxicity[f] at 30 mg/kg | Mice plasma concen- tration[g] | Tg Mice[h] |
| PB 981 | | | BAS: 580% (1 nM- 10 μM) | | 350.44 | 5.39 | | | |
| PB 982 | | | BAS: 188% (1 nM- 10 μM) | | 283.42 | −0.4 | | | |
| PB 983 | | | BAS: 278% (1 nM- 10 μM) | | 268.38 | 4.96 | | | |
| PB 985 | | | BAS: 265% (1 nM- 10 μM) | | 280.39 | 4.54 | | | |

-continued
| | In vitro Efficacy Profile | | | Physico-chemical properties | | In vivo Efficacy and Safety Profile | | |
|---|---|---|---|---|---|---|---|---|
| | H$_2$O$_2$ IC$_{50}$ (μM)$^a$ | Cytotox (% viable at 1 and 10 μM)$^b$ | CuTy$^c$ BAS$^d$ | Disaggregation$^e$ | Parent MW/ PSA | ClogP ElogD (E) or ClogD (C) | Toxicity$^f$ at 30 mg/kg | Mice plasma concentration$^g$ | Tg Mice$^h$ |
| PB 986 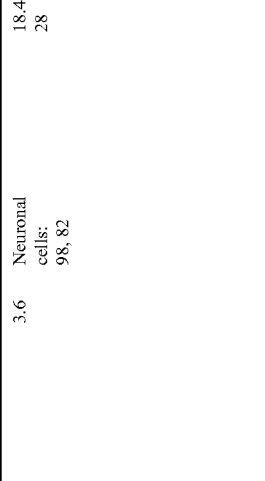 | 3.6 | Neuronal cells: 98, 82 | | 18.4, 28 | 295.30 | 2.80 | | | |
| PB 987 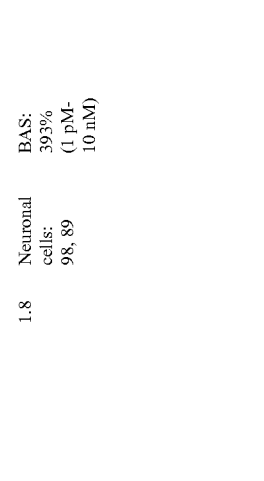 | 1.8 | Neuronal cells: 98, 89 | BAS: 393% (1 pM- 10 nM) | | 355.36 | 1.08 | | | |

-continued

| | In vitro Efficacy Profile | | | | Physico-chemical properties | | In vivo Efficacy and Safety Profile | | |
|---|---|---|---|---|---|---|---|---|---|
| | $H_2O_2$ $IC_{50}$ $(\mu M)^a$ | Cytotox (% viable at 1 and 10 μM)$^b$ | CuTy$^c$ BAS$^d$ | Disaggre- gation$^e$ | Parent MW/ PSA | ClogP ElogD (E) or ClogD (C) | Toxicity$^f$ at 30 mg/kg | Mice plasma concen- tration$^g$ | Tg Mice$^h$ |
| PB 988 | >10 | Neuronal cells: 93, 93 | BAS: 137% (1 μM- 100 μM) | | 352.35 | 1.76 | | | |
| PB 990 | 0.40 | Neuronal cells: 97, 57 | BAS: 183% (1 μM- 100 μM) | | 293.37 | 2.51 | | | |

| | In vitro Efficacy Profile | | | | Physico-chemical properties | | In vivo Efficacy and Safety Profile | | |
|---|---|---|---|---|---|---|---|---|---|
| | H$_2$O$_2$ IC$_{50}$ (μM)$^a$ | Cytotox (% viable at 1 and 10 μM)$^b$ | CuTy$^c$ BAS$^d$ | Disaggregation$^e$ | Parent MW/ PSA | ClogP ElogD (E) or ClogD (C) | Toxicity$^f$ at 30 mg/kg | Mice plasma concentration$^g$ | Tg Mice$^h$ |
| PB 991 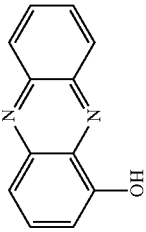 | 0.47 | Neuronal cells: 96, 67 | BAS: 222% (1 nM-1 μM) | | 265.32 | 1.11 | | | |
| PB 1006 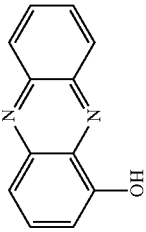 | 0.53 | Neuronal cells: 107, 75 | BAS: 463% (1 pM-10 nM) | 5.27, 49.5 | 222.25 | 3.00 | | | |
| PB 1026 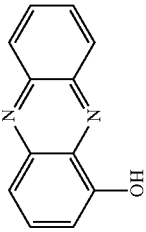 | 0.23 | | BAS: 186% (1 nM-10 μM) | | 196.21 | 2.35 | | | |
| PB 1027 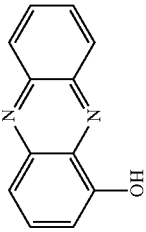 | | | BAS: 306% (1 nM-10 μM) | | 196.21 | 3.17 | | | |

-continued

| | In vitro Efficacy Profile | | | Physico-chemical properties | | In vivo Efficacy and Safety Profile | | | |
|---|---|---|---|---|---|---|---|---|---|
| | $H_2O_2$ $IC_{50}$ $(\mu M)^a$ | Cytotox (% viable at 1 and 10 $\mu M)^b$ | CuTy$^c$ BAS$^d$ | Disaggre- gation$^e$ | Parent MW/ PSA | ClogP ElogD (E) or ClogD (C) | Toxicity$^f$ at 30 mg/kg | Mice plasma concen- tration$^g$ | Tg Mice$^h$ |
| PB 1033 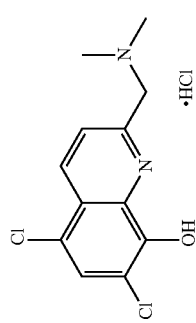 | 0.35 | Neuronal cells: 84, 72 M17 cells: 94, 54.3 | CuTy: 100% inhibition BAS: 470% (1 nM- 10 µM) | 18.6, 33.2 | 271.1 | 3.51 (C) 1.07 | 10 days, none | Up to 500 ng/ml | −29% insoluble, −37% soluble, −42% plaque |
| PB 1038 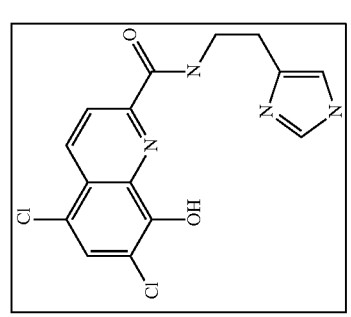 | 0.26 | Neuronal cells: 91, 84 | BAS: 627% (1 nM- 10 µM) | 4.85, 51.3 | 351.19 | 2.79 ELogD7 A=2.92 | | Up to 2694 ng/ mL | Decrease insol, Increase sol, Decrease plaque |
| PB 1041 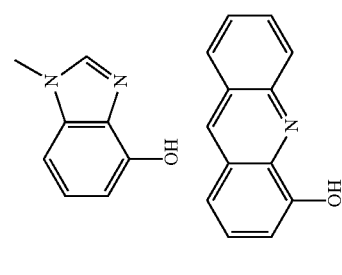 | | | BAS: 319% (1 nM- 10 µM) | | 180.25 | 1.65 | | | |
| PB 1043 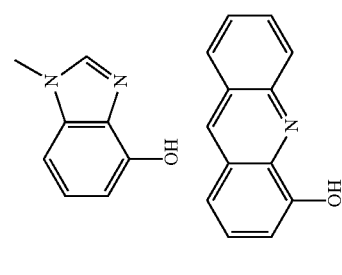 | | | BAS: 175% (100 nM- 10 µM) | | 195.22 | 3.46 | | | |

| | In vitro Efficacy Profile | | | Physico-chemical properties | | In vivo Efficacy and Safety Profile | | |
|---|---|---|---|---|---|---|---|---|
| | H$_2$O$_2$ IC$_{50}$ (μM)$^a$ | Cytotox (% viable at 1 and 10 μM)$^b$ | CuTy$^c$ BAS$^d$ | Disaggregation$^e$ | Parent MW/ PSA | ClogP ElogD (E) or ClogD (C) | Toxicity$^f$ at 30 mg/kg | Mice plasma concentration$^g$ | Tg Mice$^h$ |

| | | | | | |
|---|---|---|---|---|---|
| PB 1044 | | | BAS: 212% (1 nm- 10 μM) | | 149.15 | −2.28 |
| PB 1045 | | | BAS: 166% (1 nm- 10 μM) | | 238.63 | 2.21 |
| PB 1046 | | | BAS: 244% (1 nm- 10 μM) | | 220.19 | 2.02 |
| PB 1048 | | | BAS: 257% (1 nm- 10 μM) | | 162.15 | −0.19 |

-continued

| | | In vitro Efficacy Profile | | | | Physico-chemical properties | | In vivo Efficacy and Safety Profile | | |
|---|---|---|---|---|---|---|---|---|---|---|
| | | $H_2O_2$ $IC_{50}$ (μM)[a] | Cytotox (% viable at 1 and 10 μM)[b] | CuTy[c] BAS[d] | Disaggre-gation[e] | Parent MW/ PSA | ClogP ElogD (E) or ClogD (C) | Toxicity[f] at 30 mg/kg | Mice plasma concen-tration[g] | Tg Mice[h] |
| PB 1049 | [structure: quinazolinone with OH] | | | BAS: 237% (1-100 nm, 10 μM) | | 162.15 | 0.49 | | | |
| PB 1051 | [structure: dichloro-hydroxyquinoline with CH2NHEt·HCl] | 0.38 | Neuronal cells: 87, 56 M17 cells: 78.3, 44 | BAS: 270% (1 nM-10 μM) | >20, 22.3 | 307.6 44.6 | 3.58 | 10 days, none | Up to 403 ng/mL | −21% insol, slight increase in sol, −39% plaque |
| PB 1052 | [structure: 2-(2-pyridyl)-5,7-dichloro-8-hydroxyquinoline, boxed] | 0.64 | Neuronal cells: 55, 31 | BAS: 212% (1nM-10 μM) | 3.3, 62.8 | 291.14 | 4.21 | | | Decrease insol, Decrease sol, Decrease plaque |

| | In vitro Efficacy Profile | | | | Physico-chemical properties | | In vivo Efficacy and Safety Profile | | |
|---|---|---|---|---|---|---|---|---|---|
| | $H_2O_2$ $IC_{50}$ ($\mu M$)[f] | Cytotox (% viable at 1 and 10 $\mu M$)[b] | CuTy[c] BAS[d] | Disaggregation[e] | Parent MW/ PSA | ClogP ElogD (E) or ClogD (C) | Toxicity[f] at 30 mg/kg | Mice plasma concentration[g] | Tg Mice[h] |
| PB 1063 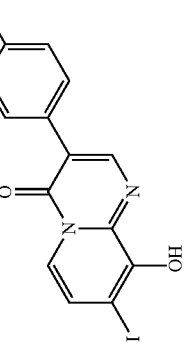 | 0.62 | Neuronal cells: 41, 33 | | 19.7, 40.5 | 398.6 52.9 | 3.41 | 10 days, mild toxic signs | Up to 450 ng/ mL in mice | |
| PB 1066 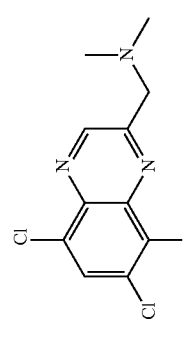 | >10 | Neuronal cells: 92, 95 | | >50, 35 | 272.1 49.3 | 2.57 (C) 0.37 | | Up to 1000 ng/mL in mice | |
| PB 1069 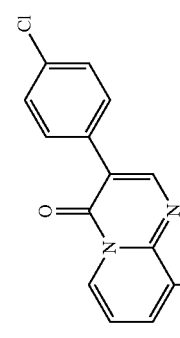 | 0.48 | Neuronal cells: 97, 42 M17 cells: 41.2, 25.8 | | 11.3, 34.8 | 272.7 | 2.62 | | | |
| PB 1073 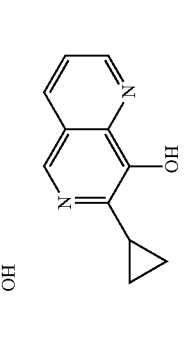 | 0.52 | Neuronal cells: 100, 98 | | 4.7, 50 | 186.1 46.0 | 2.22 | 6 days, none | Up to 350 ng/ mL in mice | |

| | In vitro Efficacy Profile | | | | Physico-chemical properties | | In vivo Efficacy and Safety Profile | | |
|---|---|---|---|---|---|---|---|---|---|
| | $H_2O_2$ $IC_{50}$ (μM)[a] | Cytotox (% viable at 1 and 10 μM)[b] | CuTy[c] BAS[d] | Disaggregation[e] | Parent MW/ PSA | ClogP ElogD (E) or ClogD (C) | Toxicity[f] at 30 mg/kg | Mice plasma concentration[g] | Tg Mice[h] |
| PB-1075 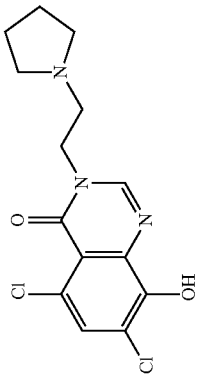 | 0.73 | Neuronal cells: 104, 91 M17 cells: 103.6, 101.3 | | Inactive >20, 0 | 328.2 58.4 | 2.58 | 14 days, 1 of 4 death | Up to 520 ng/ mL in mice | Increase insol, decrease sol, −23% plaque |
| PB-1076 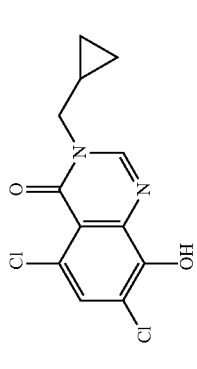 | 0.45 | Neuronal cells: 116, 105 M17 cells: 96.2, 76.8 | 100% inhibit | >20, 15.1 | 285.1 52.9 | 2.74 | 11 days, none | Up to 2698 ng/ mL in mice | −26% insol, −37% sol, −29% plaque |
| PB-1077 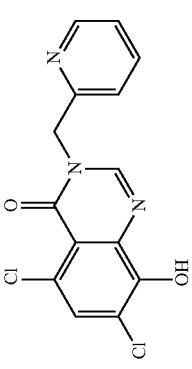 | 0.48 | Neuronal cells: 99, 98 M17 cells: 97.7, 91 | CuTy: 50% inhibition | >20, 24 | 322.2 65.79 | 2.03 | 10 days, none | Up to 984 ng/ mL in mice | No change in insol, No change in sol, −30% plaque |
| PB-1084 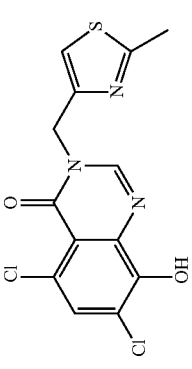 | 0.36 | Neuronal cells: 100, 93 M17 cells: 97, 95.7 | CuTy: 75% inhibition | 40.7, 23.4 | 342.2 94.03 | 2.37 | 10 days, none | Up to 2439 ng/ mL | No change in insol, −29% sol, decrease plaque |

-continued

| | In vitro Efficacy Profile | | | | Physico-chemical properties | | In vivo Efficacy and Safety Profile | | | |
|---|---|---|---|---|---|---|---|---|---|---|
| | H$_2$O$_2$ IC$_{50}$ (μM)[a] | Cytotox (% viable at 1 and 10 μM)[b] | CuTy[c] BAS[d] | Disaggre-gation[e] | Parent MW/ PSA | ClogP ElogD (E) or ClogD (C) | Toxicity[f] at 30 mg/kg | Mice plasma concen-tration[g] | Tg Mice[h] |
| PB-1085 | 0.37 | Neuronal cells: 99, 72 M17 cells: 104.9, 76.2 | CuTy: 90% inhibition | >20, 25 | 340.2 78.9 | 1.95 | 10 days, none | Up to 3644 ng/ mL | −34% insol, increase sol, −43% plaque |
| PB 1088 | 0.84 | Neuronal cells: 102, 94 | | >20, 16.4 | 325.2 | 1.94 | 10 days, none | Up to 3896 ng/ mL | |
| PB 1089 | 0.78 | Neuronal cells: 96, 83 | | >20, 16.4 | 322.2 | 2.31 | 10 days, none | Up to 39 ng/ mL | |
| PB 1091 | 0.46 | Neuronal cells: 100, 92 | | >20, 23.4 | 336.2 | 2.36 | 10 days, none | Up to 59 ng/ mL | |

| | Structure | In vitro Efficacy Profile | | | | Physico-chemical properties | | In vivo Efficacy and Safety Profile | | |
|---|---|---|---|---|---|---|---|---|---|---|
| | | H$_2$O$_2$ IC$_{50}$ (μM)[a] | Cytotox (% viable at 1 and 10 μM)[b] | CuTy[c] BAS[d] | Disaggregation[e] | Parent MW/PSA | ClogP ElogD (E) or ClogD (C) | Toxicity[f] at 30 mg/kg | Mice plasma concentration[g] | Tg Mice[h] |
| PB-1093 | | 0.39 | Neuronal cells: 122, 93 | | >20, 16 | 338.2 | 2.58 | 10 days, none | Up to 80 ng/mL | |
| PB-1100 | | 0.42 | Neuronal cells: 100, 92 M17 cells: 108.1, 80.5 | CuTy: 10% inhibition | 17, 42 | 358.1 | 3.13 | 10 days, none | Up to 1,130.6 ng/mL | |
| PB-1101 | | 4.1 | Neuronal cells: 89, 67 M17 cells: 94.9, 26.8 | 10% inhibition | 11.7, 45 | 565.2 | 3.42 | 10 days, none | | |
| PB-1104 | | 0.35 | Neuronal cells: 86, 78 | | >20, 19.1 | 257.12 | 2.71 | | | |

-continued

| | | In vitro Efficacy Profile | | | Physico-chemical properties | | In vivo Efficacy and Safety Profile | | |
|---|---|---|---|---|---|---|---|---|---|
| | $H_2O_2$ $IC_{50}$ $(\mu M)^a$ | Cytotox (% viable at 1 and 10 $\mu M)^b$ | CuTy[c] BAS[d] | Disaggregation[e] | Parent MW/ PSA | ClogP ElogD (E) or ClogD (C) | Toxicity[f] at 30 mg/kg | Mice plasma concentration[g] | Tg Mice[h] |
| PB 1106 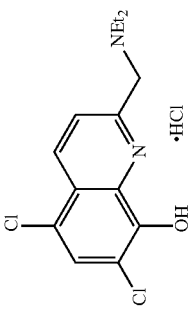 | 0.40 | Neuronal cells: 74, 70 | | 14.2, 17.9 | 299.2 | 4.23 | | | |
| PB 1108 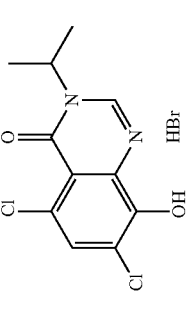 | 0.25 | Neuronal cells: 104, 71 M17 cells: 94.3, 74.5 | | >20, 46.5 | 273.1 | 2.60 | 10 days, none | Up to 383 ng/ mL | |
| PB 1112 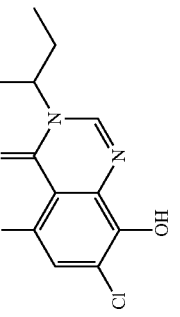 | 0.33 | Neuronal cells: 94, 67 M17 cells: 99.2, 68.6 | CuTy: 125% inhibition | >20, 46.4 | 287.1 | 3.13 | 10 days, none | Up to 2949 ng/ mL | |
| PB 1113 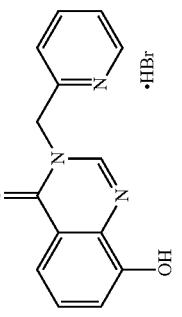 | 3.2 | Neuronal cells: 97, 90 | | >20, 25.5 | 269.3 | 1.76 | | | |

| | In vitro Efficacy Profile | | | | Physico-chemical properties | | In vivo Efficacy and Safety Profile | | |
|---|---|---|---|---|---|---|---|---|---|
| | $H_2O_2$ $IC_{50}$ $(\mu M)^a$ | Cytotox (% viable at 1 and 10 $\mu M)^b$ | CuTy$^c$ BAS$^d$ | Disaggre- gation$^e$ | Parent MW/ PSA | ClogP ElogD (E) or ClogD (C) | Toxicity$^f$ at 30 mg/kg | Mice plasma concen- tration$^g$ | Tg Mice$^h$ |
| PB 1114 | 0.58 | Nueronal cells: 101, 73 | | >20, 19.2 | 366.0 | 3.35 | | | |
| PB 1115 | 0.95 | Neuronal cells: 93, 58 M17 cells: 104.3, 95.9 | | >20, 17 | 259.1 | 2.29 | | | |
| PB 1116 | 1.63 | Neuronal cells: 103, 92 | | >20, 16.8 | 246.3 | 3.02 | | | |
| PB 1117 | 0.72 | M17 cells: 109.2, 96 | | <0.4, 57.3 | 253.3 | 0.87 | | | |

| | In vitro Efficacy Profile | | | Physico-chemical properties | | In vivo Efficacy and Safety Profile | | | |
|---|---|---|---|---|---|---|---|---|---|
| | $H_2O_2$ $IC_{50}$ $(\mu M)^a$ | Cytotox (% viable at 1 and 10 μM)$^b$ | CuTy$^c$ BAS$^d$ | Disaggregation$^e$ | Parent MW/ PSA | ClogP ElogD (E) or ClogD (C) | Toxicity$^f$ at 30 mg/kg | Mice plasma concentration$^g$ | Tg Mice$^h$ |
| PB 1118 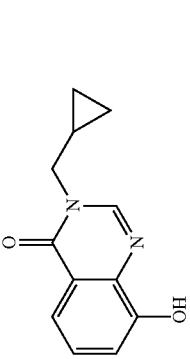 | 1.44 | M17 cells: 106.8, 88.6 | | <0.4, 58 | 216.2 | 1.58 | | | |
| PB 1119 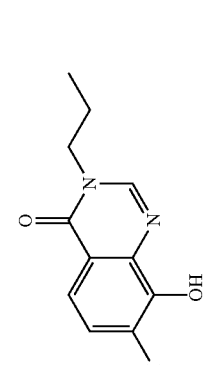 | 0.28 | | | 2.72, 51.5 | 330.1 | 2.48 | 10 days, none | Up to 1096 ng/ mL | |
| PB 1120 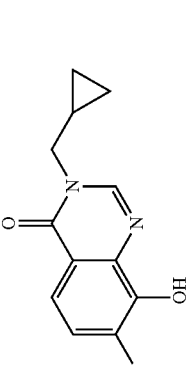 | 0.28 | M17 cells: 106.9, 62 | CuTy: 25% inhibition | 5.6, 47.5 | 342.1 52.9 | 2.40 | 10 days, none | Up to 2508 ng/ mL | No change in insol, sol Decrease in plaque |
| PB 1122 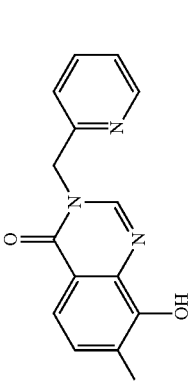 | 0.52 | M17 cells: 97.5, 79.5 | | 0.66, 62.4 | 379.2 | 1.69 | 10 days, none | Up to 1538 ng/ mL | |

-continued

| | | In vitro Efficacy Profile | | | Physico-chemical properties | | In vivo Efficacy and Safety Profile | | |
|---|---|---|---|---|---|---|---|---|---|
| | $H_2O_2$ $IC_{50}$ (μM)[a] | Cytotox (% viable at 1 and 10 μM)[b] | CuTy[c] BAS[d] | Disaggregation[e] | Parent MW/ PSA | ClogP ElogD (E) or ClogD (C) | Toxicity[f] at 30 mg/kg | Mice plasma concentration[g] | Tg Mice[h] |
| PB 1123 | 0.29 | | | 0.91, 25 | 316.1 | 1.95 | 10 days, none | | |
| PB 1124 | 0.40 | M17 cells: 96.1, 27.1 | | >20, 8.4 | 190.2 | 0.84 | | | |
| PB 1126 | 0.37 | | | 3.7, 69 | 285.1 | 3.07 | | | |
| PB 1127 | 0.28 | M17 cells: 82.5, 23.3 | 25% inhibit | 4.5, 55 | 316.1 | 1.63 | At 10 mg/kg 10 days, none | At 10 mg/kg: Up to 7082 ng/ mL | At 10 mg/kg No effect |

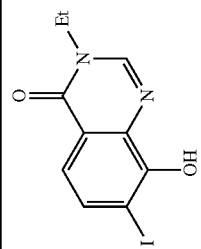
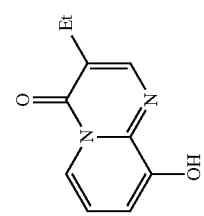
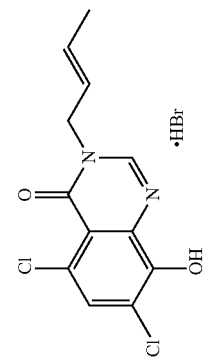
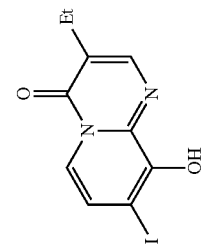

| | In vitro Efficacy Profile | | | | Physico-chemical properties | | In vivo Efficacy and Safety Profile | | |
|---|---|---|---|---|---|---|---|---|---|
| | $H_2O_2$ $IC_{50}$ (μM)[a] | Cytotox (% viable at 1 and 10 μM)[b] | CuTy[c] BAS[d] | Disaggre-gation[e] | Parent MW/ PSA | ClogP ElogD (E) or ClogD (C) | Toxicity[f] at 30 mg/kg | Mice plasma concen-tration[g] | Tg Mice[h] |
| PB 1128 | 0.34 | M17 cells: 106.5, 99.1 Neuro cells 100.6, 93.7 | CuTy: 100% inhibition | 13.2, 41 | 316.2 | 2.55 | 10 days, none | Up to 2289 ng/ mL | |
| PB 1132 | 0.47 | M17 cells: 86.3, 57.6 | | 15.2, 16 | 250.7 | 2.34 | | | |
| PB 1133 | 0.79 | | | >20, 22 | 287.7 | 1.63 | | | |
| PB 1135 | 0.27 | M17 cells: 99.7, 45.6 | CuTy: 90% inhibition | >20, 31 | 204.2 | 1.24 | 10 days, none | Up to 409 ng/ml | |

| | In vitro Efficacy Profile | | | | Physico-chemical properties | | In vivo Efficacy and Safety Profile | | |
|---|---|---|---|---|---|---|---|---|---|
| | $H_2O_2$ $IC_{50}$ ($\mu M$)[a] | Cytotox (% viable at 1 and 10 $\mu M$)[b] | CuTy[c] BAS[d] | Disaggregation[e] | Parent MW/ PSA | ClogP ElogD (E) or ClogD (C) | Toxicity[f] at 30 mg/kg | Mice plasma concentration[g] | Tg Mice[h] |
| PB 1138 | 0.30 | M17 cells: 99.7, 68.2 | | 4.7, 53 | 350.5 | 2.68 | 10 days, 2/4 deaths | Up to 1802 ng/mL | |
| PB 1140 | 0.36 | M17 cells: 92.4, 98.2 | | 3.5, 64 | 376.6 | 3.13 | At 10 mg/kg 10 days, none | At 10 mg/kg: Up to 2315 ng/ml | |
| PB 1141 | 0.48 | M17 cells: 102.8, 137 | | 19.5, 26 | 413.6 | 2.42 | | | |
| PB 1142 | 0.37 | M17 cells: 96.7, 44.2 | | 7.1, 42 | 330.12 | 2.03 | 10 days, 1/4 death | | |

| | In vitro Efficacy Profile | | | Physico-chemical properties | | In vivo Efficacy and Safety Profile | | |
|---|---|---|---|---|---|---|---|---|
| | $H_2O_2$ $IC_{50}$ (μM)[a] | Cytotox (% viable at 1 and 10 μM)[b] | CuTy[c] BAS[d] | Disaggregation[e] | Parent MW/ PSA | ClogP ElogD (E) or ClogD (C) | Toxicity[f] at 30 mg/kg | Mice plasma concentration[g] | Tg Mice[h] |

| PB 1143 | 0.48 | M17 cells: 93.3, 73.7 | | 4.1, 62 | 206.27 | 1.66 | | | |
| PB 1144 | 0.32 | M17 cells: 73.6, 37 | | 9.1, 15.5 | 218.25 | 1.90 | 10 days, none | | |
| PB 1145 | 0.66 | M17 cells: 101.7, 58.7 | | 7.2, 28 | 344.15 | 2.69 | 10 days, 2/4 death | | |
| PB 1147 | 0.26 | M17 cells: 94.7, 100.3 | CuTy: 100% inhibition | >20, 12.5 | 288.13 | 1.50 | 10 days, none | Up tp 642.6 ng/ mL | |

| | In vitro Efficacy Profile | | | | Physico-chemical properties | | In vivo Efficacy and Safety Profile | | | |
|---|---|---|---|---|---|---|---|---|---|---|
| | $H_2O_2$ $IC_{50}$ (μM)[a] | Cytotox (% viable at 1 and 10 μM)[b] | CuTy[c] BAS[d] | Disaggre- gation[e] | Parent MW/ PSA | ClogP ElogD (E) or ClogD (C) | Toxicity[f] at 30 mg/kg | Mice plasma concen- tration[g] | Tg Mice[h] |

| PB 1148 | 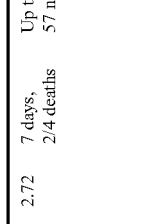 | 0.41 | | | 1.55, 70 | 234.32 | 2.72 | 7 days, 2/4 deaths | Up to 57 ng/ml | |
| PB 1149 | 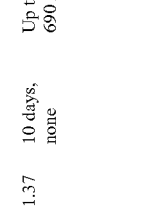 | 0.30 | M17 cells: 79.1, 45.2 Neuro cells 86.2, 12.4 | CuTy: 95% inhibition | 5, 49 | 204.23 | 1.37 | 10 days, none | Up to 690 ng/ml | No change in insol, sol, −45% plaque |
| PB 1151 |  | 0.33 | M17 cells: 80.8, 47.6 | | 5.6, 57 | 330.12 52.9 | 2.16 | | Up to 11742 ng/ ml | At 3 mg/kg: Insol (−24%) Ex- outlier No change sol, or in plaque |
| PB 1152 | 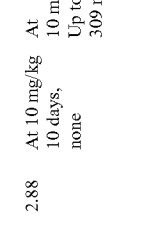 | 0.31 | M17 cells: 95.7, 71.2 | | >20, 56 | 344.15 | 2.88 | At 10 mg/kg 10 days, none | At 10 mg/kg: Up to 309 ng/ml | |

| | In vitro Efficacy Profile | | | | Physico-chemical properties | | In vivo Efficacy and Safety Profile | | |
|---|---|---|---|---|---|---|---|---|---|
| | H$_2$O$_2$ IC$_{50}$ (μM)[a] | Cytotox (% viable at 1 and 10 μM)[b] | CuTy[c] BAS[d] | Disaggre- gation[e] | Parent MW/ PSA | ClogP ElogD (E) or ClogD (C) | Toxicity[f] at 30 mg/kg | Mice plasma concen- tration[g] | Tg Mice[h] |
| PB 1153 | 0.32 | | | 4.7, 53 | 330.12 | 2.26 | 10 days, 1/4 deaths | Up to 277 ng/ml | |
| PB 1154 | 0.64 | M17 cells: 76.7, 54.2 | | >20, 31 | 313.28 | 1.31 | | | |
| PB 1155 | 0.31 | | | 3.9, 59 | 679.21 | 2.74 | | | |
| PB 1156 | 0.96 | M17 cells: 92.7, 67.5 | | >20, 22 | 256.23 | 2.19 | | | |
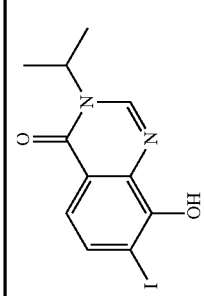
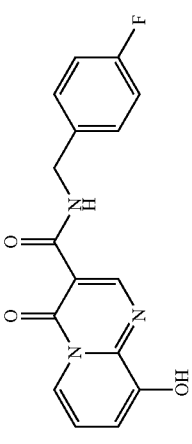
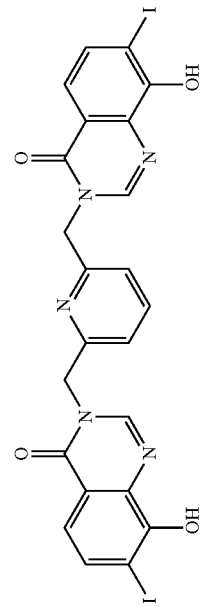
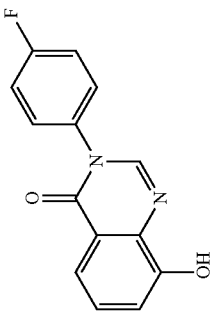

-continued

| | In vitro Efficacy Profile | | | | Physico-chemical properties | | In vivo Efficacy and Safety Profile | | |
|---|---|---|---|---|---|---|---|---|---|
| | $H_2O_2$ $IC_{50}$ (μM)[a] | Cytotox (% viable at 1 and 10 μM)[b] | CuTy[c] BAS[d] | Disaggregation[e] | Parent MW/ PSA | ClogP ElogD (E) or ClogD (C) | Toxicity[f] at 30 mg/kg | Mice plasma concentration[g] | Tg Mice[h] |

| PB 1157 | ![structure] | 0.38 | M17 cells: 90.3, 80.3 | | 8.1, 45 | 400.12 | 3.15 | 6 days, 2/4 deaths | | |
| PB 1158 | ![structure] | 0.99 | M17 cells: 104.7, 56 | | >20, 10 | 439.18 | 2.09 | 7 days, 4/4 deaths | | |
| PB 1159 | ![structure] | 0.68 | M17 cells: 115, 41.1 | | 5.06, 49.9 | 261.28 | 0.78 | | | |
| PB 1160 | ![structure] | 0.75 | M17 cells: 85.3, 63.4 | CuTy: 95% inhibition | 4.05, 56.8 | 387.17 | 1.56 | 10 days, none | Up to 27,598 ng/mL | No change in insol, −25% (sol), decrease plaque |

-continued

| | In vitro Efficacy Profile | | | | Physico-chemical properties | | In vivo Efficacy and Safety Profile | | |
|---|---|---|---|---|---|---|---|---|---|
| | $H_2O_2$ $IC_{50}$ ($\mu M$)[a] | Cytotox (% viable at 1 and 10 $\mu M$)[b] | CuTy[c] BAS[d] | Disaggregation[e] | Parent MW/ PSA | ClogP ElogD (E) or ClogD (C) | Toxicity[f] at 30 mg/kg | Mice plasma concentration[g] | Tg Mice[h] |
| PB 1161 | 0.14 | M17 cells: 101.4, 112.5 Neuro cells 105.4, 103.9 | 100% inhib | >20, 27 | 288.13 | 1.13 | 10 days, none | Up to 510.4 ng/mL | No change in insol, sol, −64% plaque |
| PB 1162 | 3.2 | M17 cells: 93.9, 36.5 | | 4.7, 52 | 382.13 | 2.99 | | | |
| PB 1163 | 0.29 | M17 cells: 106.5, 41.4 | | 11, 43.3 | 387.22 | 2.90 | | | |
| PB 1164 | 0.24 | M17 cells: 112, 111 | | >20, 26 | 399.57 | 2.20 | | | |

PB 1161: 5,7-dichloro-8-hydroxy-3-methyl-2-(methylaminomethyl)quinazolin-4(3H)-one · HBr PB 1162: 3-(4-fluorophenyl)-8-hydroxy-7-iodoquinazolin-4(3H)-one PB 1163: 3-(2-(diethylamino)ethyl)-8-hydroxy-7-iodoquinazolin-4(3H)-one PB 1164: 5-chloro-8-hydroxy-7-iodo-3-(pyridin-3-yl)quinazolin-4(3H)-one

| | In vitro Efficacy Profile | | | | Physico-chemical properties | | In vivo Efficacy and Safety Profile | | | |
|---|---|---|---|---|---|---|---|---|---|---|
| | H$_2$O$_2$ IC$_{50}$ (μM)$^a$ | Cytotox (% viable at 1 and 10 μM)$^b$ | CuTy$^c$ BAS$^d$ | Disaggregation$^e$ | Parent MW/ PSA | ClogP ElogD (E) or ClogD (C) | Toxicity$^f$ at 30 mg/kg | Mice plasma concentration$^g$ | Tg Mice$^h$ | |
| PB 1165 | 0.89 | M17 cells: 96.7, 107.1 | | 4.7, 52 | 346.19 | 3.65 | 10 days, none | Up tp 1593 ng/ml | No change in insol, sol, Decrease plaque | [structure] |
| PB 1166 | 0.43 | M17 cells: 105, 115.8 | | >20, 21.7 | 387.17 | 1.81 | | | | [structure] |
| PB 1167 | 0.39 | M17 cells: 92.2, 98.7 | | 7.4, 39.3 | 401.2 | 2.24 | | | | [structure] |
| PB 1168 | 0.4 | M17 cells: 85.7, 43 | | 1.11, 70 | 332.2 | 3.12 | 10 days, none, 1/4 mild signs | Up to 400 ng/ml | | [structure] |

| | In vitro Efficacy Profile | | | Physico-chemical properties | | In vivo Efficacy and Safety Profile | | |
|---|---|---|---|---|---|---|---|---|
| | $H_2O_2$ $IC_{50}$ (μM)[a] | Cytotox (% viable at 1 and 10 μM)[b] CuTy[c] BAS[d] | Disaggregation[e] | Parent MW/ PSA | ClogP ElogD (E) or ClogD (C) | Toxicity[f] at 30 mg/kg | Mice plasma concentration[g] | Tg Mice[h] |
| PB 1169 | 0.31 | | 1.44, 64 | 442.0 | 3.09 | | | |
| PB 1170 | 0.72 | M17 cells: 127.4, 104.8 | 4.28, 53 | 461.2 | 2.76 | | | |
| PB 1173 | >20 | | >20, 10 | 210.24 | 2.33 | | | |
| PB 1174 | 0.96 | M17 cells: 60.1, 34.2 | 14.7, 22 | 356.34 | 1.45 | | | |

| | In vitro Efficacy Profile | | | Physico-chemical properties | | In vivo Efficacy and Safety Profile | | |
|---|---|---|---|---|---|---|---|---|
| | H$_2$O$_2$ IC$_{50}$ (μM)$^a$ | Cytotox (% viable at 1 and 10 μM)$^b$ | CuTy$^c$ BAS$^d$ Disaggregation$^e$ | Parent MW/ PSA | ClogP ElogD (E) or ClogD (C) | Toxicity$^f$ at 30 mg/kg | Mice plasma concentration$^g$ | Tg Mice$^h$ |
| PB 1176 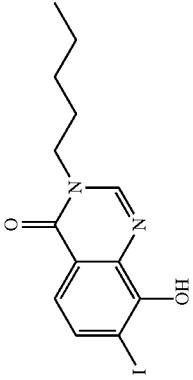 | 0.3 | M17 cells: 86.3, 38.5 | 6.9, 45 | 358.18 | 3.53 | | | |
| PB 1177 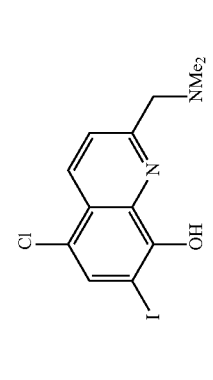 | 0.29 | M17 cells: 97.9, 24.4 | 2.4, 79 | 362.60 | 3.56 | 1 day, 3/4 deaths | | |
| PB 1182 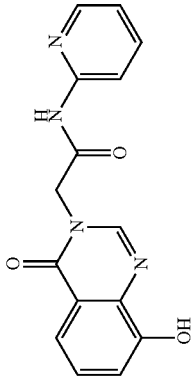 | 0.59 | M17 cells: 110.1, 98.2 | >20, 24 | 269.28 | 1.12 | | | |
| PB 1184 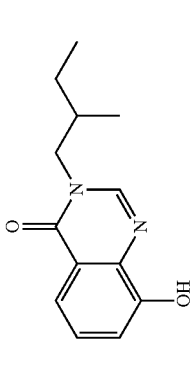 | 0.54 | M17 cells: 102.7, 47.2 | 5.27, 49 | 232.28 | 2.59 | | | |

| | In vitro Efficacy Profile | | | Physico-chemical properties | | In vivo Efficacy and Safety Profile | | |
|---|---|---|---|---|---|---|---|---|
| | $H_2O_2$ IC$_{50}$ (μM)[a] | Cytotox (% viable at 1 and 10 μM)[b] | CuTy[c] BAS[d] | Disaggre- gation[e] | Parent MW/ PSA | ClogP ElogD (E) or ClogD (C) | Toxicity[f] at 30 mg/kg | Mice plasma concen- tration[g] | Tg Mice[h] |

| | | | | | | | |
|---|---|---|---|---|---|---|---|
| PB 1185 | 0.6 | M17 cells: 103.9, 106.5 | | 9.5, 35 | 335.31 | 1.94 | | |
| PB 1191 | >10 | | | 6.89, 10 | 241.31 | 4.25 | | |
| PB 1194 | >10 | | | >20, 21.5 | 264.33 | 3.08 | | |

−continued

| | In vitro Efficacy Profile | | | Physico-chemical properties | | In vivo Efficacy and Safety Profile | | |
|---|---|---|---|---|---|---|---|---|
| | H$_2$O$_2$ IC$_{50}$ (μM)[a] | Cytotox (% viable at 1 and 10 μM)[b] | CuTy[c] BAS[d] | Disaggregation[e] | Parent MW/ PSA | ClogP ElogD (E) or ClogD (C) | Toxicity[f] at 30 mg/kg | Mice plasma concentration[g] | Tg Mice[h] |
| PB 1195 | >10 | | | >20, 19.9 | 252.29 | 3.42 | | | |
| PB 1196 | >10 | | | 16.57, 33.7 | 360.20 | 4.40 | | | |
| PB 1199 | 1.64 | M17 cells: 115.2, 102.7 | | >20, 20.4 | 304.34 | 0.66 | | | |
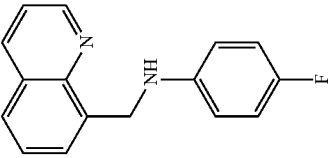
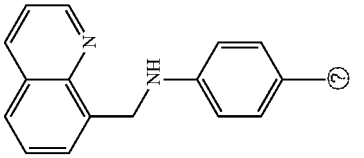
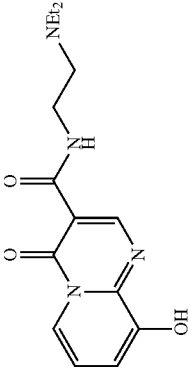

| | In vitro Efficacy Profile | | | | Physico-chemical properties | | In vivo Efficacy and Safety Profile | | |
|---|---|---|---|---|---|---|---|---|---|
| | $H_2O_2$ $IC_{50}$ ($\mu M$)[a] | Cytotox (% viable at 1 and 10 $\mu M$)[b] | CuTy[c] BAS[d] | Disaggre- gation[e] | Parent MW/ PSA | ClogP ElogD (E) or ClogD (C) | Toxicity[f] at 30 mg/kg | Mice plasma concen- tration[g] | Tg Mice[h] |
| PB 1239 | 0.48 | M17 cells: 109.2, 98.2 | CuTy: 50% inhibition | | 361.18 | 2.60 | 10 days, none | Up to 98.3 ng/ mL | |
| PB 1240 | 0.32 | M17 cells: 106.4, 100.2 | CuTy: 60% inhibition | | 322.15 | 2.03 | 10 days, none | Up to 4023.4 ng/mL | |
| PB 1241 | 0.44 | M17 cells: 105.4, 90.4 Neuro cells 98.4, 90.9 | CuTy: 80% inhibition | | 322.15 | 2.03 | 10 days, none | Up to 2181.1 ng/mL | |
| PB 1242 | 0.28 | M17 cells: 102.7, 102.6 | CuTy: 50% inhibition | | 308.12 | 1.81 | 10 days, none | Up to 144.2 ng/ mL | |

-continued

| | In vitro Efficacy Profile | | | | Physico-chemical properties | | In vivo Efficacy and Safety Profile | | |
|---|---|---|---|---|---|---|---|---|---|
| | H$_2$O$_2$ IC$_{50}$ (μM)[a] | Cytotox (% viable at 1 and 10 μM)[b] | CuTy[c] BAS[d] | Disaggregation[e] | Parent MW/ PSA | ClogP ElogD (E) or ClogD (C) | Toxicity[f] at 30 mg/kg | Mice plasma concentration[g] | Tg Mice[h] |
| PB 1243 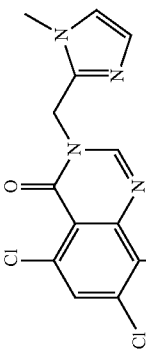 | 0.38 | M17 cells: 112, 122.3 | CuTy: 60% inhibition | | 325.15 | 1.34 | 10 days, none | Up to 13214.8 ng/mL | |
| PB 1244 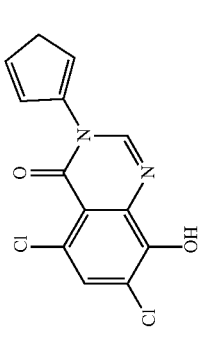 | 1.32 | M17 125.7, 114.8 | CuTy: 10% inhibition | | 297.10 | 1.69 | 10 days, none | Up to 1477.4 ng/mL | |
| PB 1246 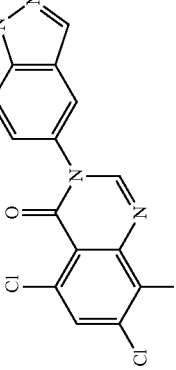 | 0.31 | M17 cells: 104.3, 73.5 | CuTy: 120% inhibition | | 347.16 | 2.78 | 10 days, none | Up to 126 ng/ mL | |
| PB 1247 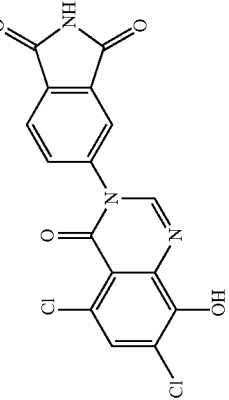 | 0.56 | M17 cells: 101.2, 110.8 | CuTy: 150% inhibition | | 376.15 | 2.297 | 10 days, none | | |

-continued

| | In vitro Efficacy Profile | | | | Physico-chemical properties | | In vivo Efficacy and Safety Profile | | |
|---|---|---|---|---|---|---|---|---|---|
| | H$_2$O$_2$ IC$_{50}$ (μM)[a] | Cytotox (% viable at 1 and 10 μM)[b] | CuTy[c] BAS[d] | Disaggre-gation[e] | Parent MW/ PSA | ClogP ElogD (E) or ClogD (C) | Toxicity[f] at 30 mg/kg | Mice plasma concen-tration[g] | Tg Mice[h] |
| PB 1249 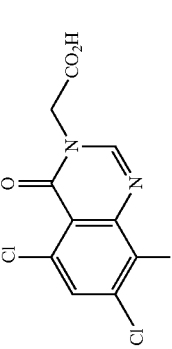 | 0.49 | M17 cells: 105, 100.7 | CuTy: 100% inhibition | | 289.08 | 1.63 | 10 days, none | Up to 4830.2 ng/ml | |
| PB 1250 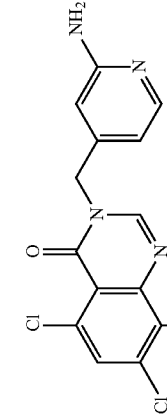 | 0.48 | M17 cells: 114.8, 100.7 | CuTy: 80% inhibition | | 337.17 | 1.71 | 10 days, 1/4 deaths | | |
| PB 1252 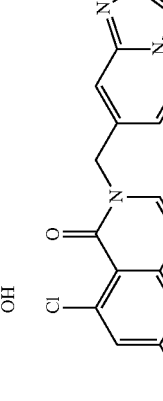 | 0.72 | M17 cells: 105.4, 105.1 Neuro cells 94.6, 103.1 | CuTy: 50% inhibition | | 361.18 | 2.60 | 10 days, none | Up to 1465.4 ng/mL | |
| PB 1253 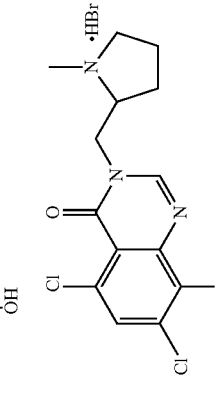 | 0.43 | M17 cells: 106.6, 93.9 | CuTy: 70% inhibition | | 328.20 | 2.57 | 10 days, none | Up to 382.5 ng/ mL | |

-continued

| | In vitro Efficacy Profile | | | | Physico-chemical properties | | In vivo Efficacy and Safety Profile | | |
|---|---|---|---|---|---|---|---|---|---|
| | H$_2$O$_2$ IC$_{50}$ (μM)[a] | Cytotox (% viable at 1 and 10 μM)[b] | CuTy[c] BAS[d] | Disaggre-gation[e] | Parent MW/ PSA | ClogP ElogD (E) or ClogD (C) | Toxicity[f] at 30 mg/kg | Mice plasma concen-tration[g] | Tg Mice[h] |
| PB 1254 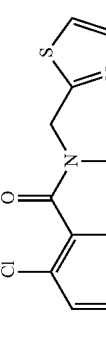 | 0.25 | M17 cells: 106.6, 106 | CuTy: 90% inhibition | | 328.17 | 1.88 | 10 days, none | Up to 441.4 ng/mL | |
| PB 1255 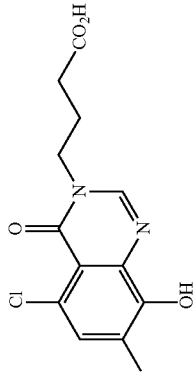 | 0.93 | M17 cells: 109.7, 102.9 Neuro cells 97.9, 98.0 | CuTy: 125% inhibition | | 317.12 | 1.92 | 10 days, none | Up to 17008 ng/mL | |
| PB 1256 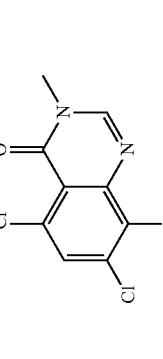 | 0.68 | M17: 101.5, 100.4 98.9, 103.9 | CuTy 30% inhibition | | 361.18 | 2.95 | 10 days, none | Up to 2796 ng/mL | |
| PB 1257 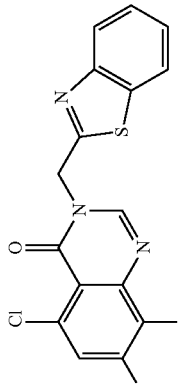 | 0.69 | M17 cells: 111.1, 80.9 | CuTy: 60% inhibition | | 378.23 | 3.47 | 10 days, none | Up to 166.1 ng/mL | |

| | In vitro Efficacy Profile | | | | Physico-chemical properties | | In vivo Efficacy and Safety Profile | | |
|---|---|---|---|---|---|---|---|---|---|
| | H$_2$O$_2$ IC$_{50}$ (μM)[a] | Cytotox (% viable at 1 and 10 μM)[b] | CuTy[c] BAS[d] | Disaggre- gation[e] | Parent MW/ PSA | ClogP ElogD (E) or ClogD (C) | Toxicity[f] at 30 mg/kg | Mice plasma concen- tration[g] | Tg Mice[h] |
| PB 1262 | 0.94 | M17 106.5, 94.2 104.6, 83.7 | CuTy No effect | | 326.14 | 1.84 | 10 days, none (16/11/05) | Up to 7107 ng/ mL | |
| PB 1264 | 0.45 | M17 cells: 103, 104.8 | CuTy: 100% inhibition | | 365.21 | 2.02 | 10 days, none | Up to 1639.8 ng/mL | |
| PB 1267 | 0.37 | M17 cells: 94.4, 74.5 | CuTy: 110% inhibition | | 342.22 | 2.57 | 10 days, none | Up to 1166.6 ng/ml | |
| PB 1268 | 0.36 | M17 cells 99.2, 102.1 | CuTy: 110% inhibition | | 316.18 | 2.13 | 10 days, none | Up to 975.9 ng/ml | |

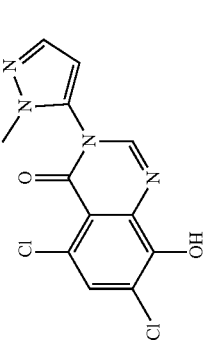
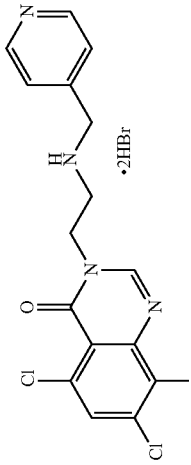
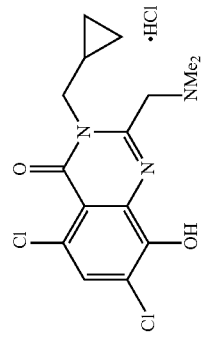
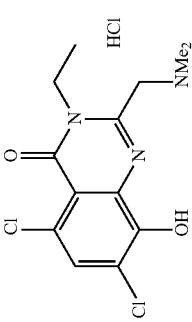

-continued

| | | In vitro Efficacy Profile | | | | Physico-chemical properties | | In vivo Efficacy and Safety Profile | | |
|---|---|---|---|---|---|---|---|---|---|---|
| | | $H_2O_2$ $IC_{50}$ ($\mu M$)[a] | Cytotox (% viable at 1 and 10 $\mu M$)[b] | CuTy[c] BAS[d] | Disaggregation[e] | Parent MW/ PSA | ClogP ElogD (E) or ClogD (C) | Toxicity[f] at 30 mg/kg | Mice plasma concentration[g] | Tg Mice[h] |
| PB 1269 | ![structure: 5,6-dichloro-8-hydroxy-3-methyl-2-((dimethylamino)methyl)quinazolin-4(3H)-one · HBr] | 0.28 | M17 cells 109.3, 114.7 | CuTy: 110% inhibition | | 302.156 | 1.60 | 10 days, 1/4 mild signs | Up to 492.1 ng/ml | |
| PB 1270 | ![structure: 1,2-diethyl-3-hydroxy-pyridinone · HCl] | >10 | M17 cells 102.8, 108.3 | CuTy: 80% inhibition | | 167.21 | 0.15 | 10 days, none | Up to 493.7 ng/ml At 120 mg/kg, up tp 4455 ng/ml | |
| PB 1271 | ![structure: 5,6-dichloro-8-hydroxy-3-isobutyl-2-((dimethylamino)methyl)quinazolin-4(3H)-one · HCl] | 0.17 | M17 cells 104.4, 61.5 | CuTy: 50% inhibition | | 344.34 | | | | |

[a] concentration in μM of test compound required to inhibit 50% of $A_{beta}$ $H_2O_2$ production
[b] viability of primary cortical neuronal cultured cells (Neuronal cells) or M17 human neuroblastoma cells (M17 cells) in the presence of test compound at concentrations of 1 and 10 μM.
[c] % inhibition of dityrosine oligomerization as referenced to in-house standard (set as 100% inhibition)
[d] extent by which test compound mobilizes $A_{beta}$ from the insoluble to the soluble phase of an extract of tissue from a post-mortem human AD brain. Results are referenced to baseline PBS and are quoted as the max effect achieved across the concentration range followed by the concentration or concentration range at which an effect is observed
[e] Disaggregation of $A_{beta}$:Zn (25:50 μM) Synthetic Aggregations; 1st value =EC50 (μM), 2nd value =% Aggregate reduction at 5 μM
[f] Visual observations during acute tox in mice or Tg mice experiment or PK studies in rats
[g] Confirmation of presence of compound in plasma at one or two time points (between 30 min and 4 h) after single or repeat oral dose of 30 mg/kg (unless otherwise specified)
[h] % difference from control in insoluble/soluble brain amyloid burden and % difference from control in Amyloid plaque abundance following daily oral gavage at 30 mg/kg (unless otherwise specified) over 9 weeks in 13-14 months old transgenic mice.
Only statistically significant results (p <0.05) are quoted as percentage values, trends are indicated without numbers.

Those skilled in the art will appreciate that the invention described herein is susceptible to variations and modifications other than those specifically described. It is to be understood that the invention includes all such variations and modifications. The invention also includes all of the steps, features, compositions and compounds referred to or indicated in this specification, individually or collectively, and any and all combinations of any two or more of said steps or features.

BIBLIOGRAPHY

*Arch. Ophthalmol.* 117:1329-1345, 1999

Bevan and Lloyd, *Anal. Chem.* 72:1781-1787, 2000

Goodman and Gilman's, The Pharmacological Basis for Therapeutics 7th ed, 1985

Langer, *Science,* 249:1527, 1990

Remington's Pharmaceutical Sciences, 20th ed, Williams and Wilkins, 2000

The British National Formulary 43rd ed, British Medical Association and Royal Pharmaceutical Society of Great Britain, 2002

WO 02/055081

White et al., *J Neuroscience* 18:6207-6217, 1998

Wright et al, *J Am Chem Soc* 123:1173-1183, 2001

The invention claimed is:

1. A compound selected from the following:

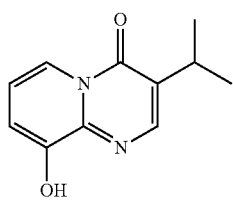
PB 1135

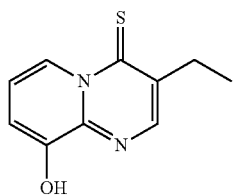
PB 1143

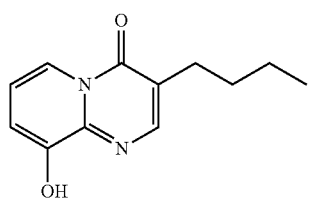 [SMILES: CCCCc1cnc2c(O)cccn2c1=O]
PB 1144

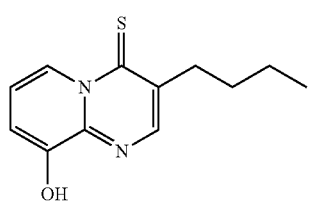 [SMILES: CCCCc1cnc2c(O)cccn2c1=S]
PB 1148

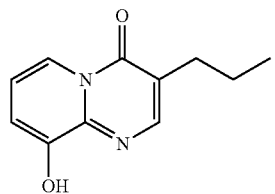
PB 1149

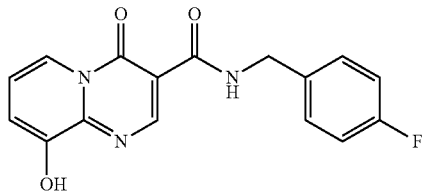 [SMILES: O=C(NCc1ccc(F)cc1)c1cnc2c(O)cccn2c1=O]
PB 1154

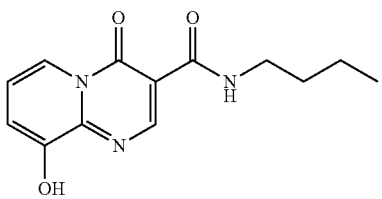 [SMILES: CCCCNC(=O)c1cnc2c(O)cccn2c1=O]
PB 1159

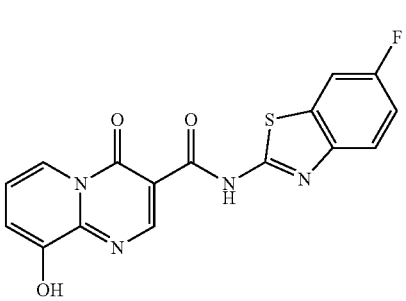 [SMILES: O=C(Nc1nc2ccc(F)cc2s1)c1cnc2c(O)cccn2c1=O]
PB 1174 and

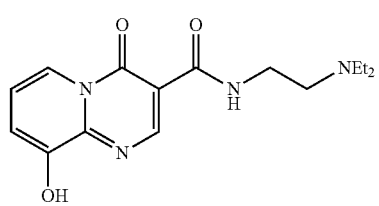
PB 1197 or a pharmaceutically acceptable salt thereof.

2. The compound of claim 1 which is

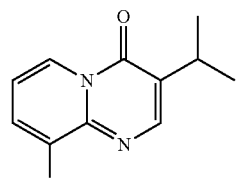

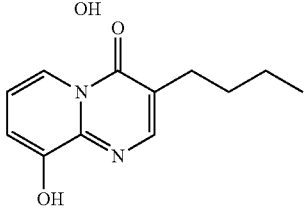

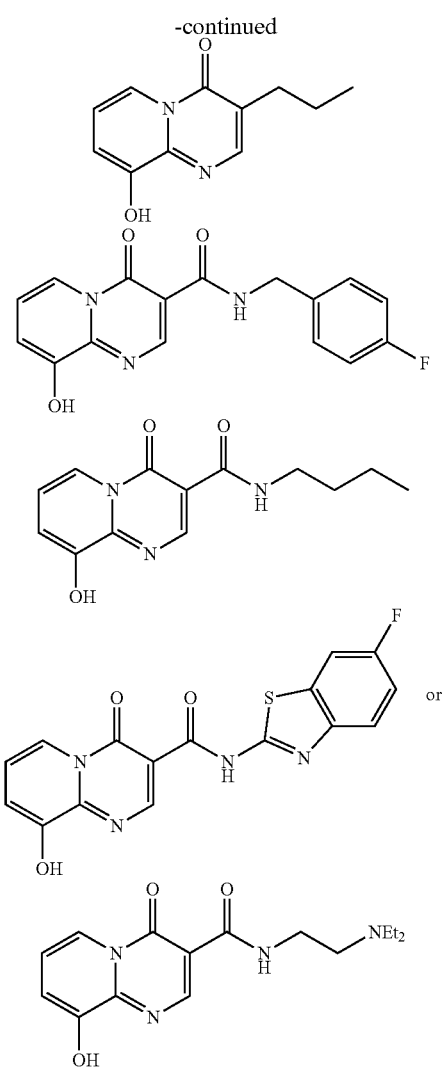

or a pharmaceutically acceptable salt thereof.
3. The compound of claim 2 which is

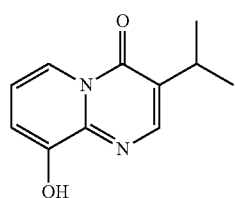

or a pharmaceutically acceptable salt thereof.
4. The compound of claim 1 which is

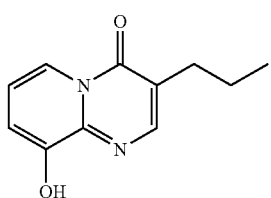

or a pharmaceutically acceptable salt thereof.

5. A pharmaceutical composition comprising a compound of claim 1 or a pharmaceutically acceptable salt thereof and a pharmaceutically acceptable carrier thereof.

6. The pharmaceutical composition according to claim 5 where the compound is

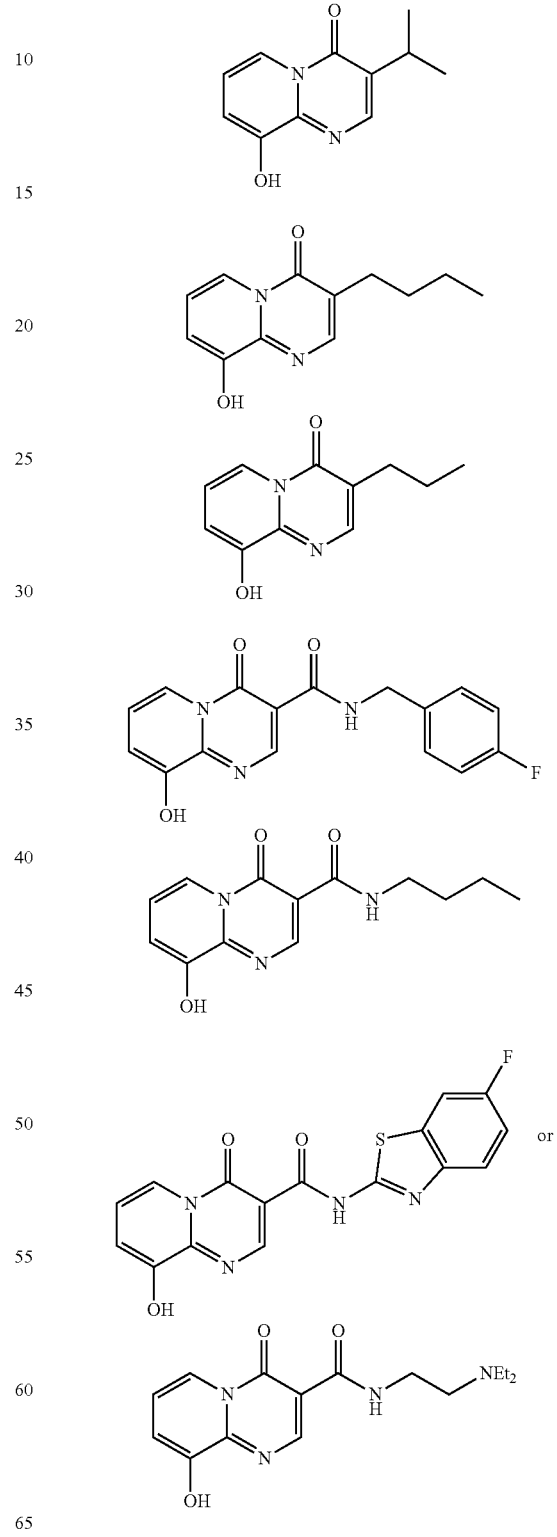

or a pharmaceutically acceptable salt thereof.

7. The pharmaceutical composition of claim 5 where the compound is
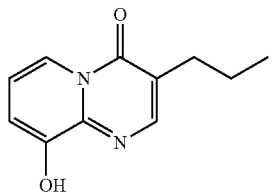
or a pharmaceutically acceptable salt thereof and a pharmaceutically acceptable carrier thereof.
* * * * *